US008940293B2

(12) United States Patent
Li et al.

(10) Patent No.: US 8,940,293 B2
(45) Date of Patent: *Jan. 27, 2015

(54) TRANSPLANTATION OF BONE MARROW STROMAL CELLS FOR TREATMENT OF NEURODEGENERATIVE DISEASES

(75) Inventors: Yi Li, Troy, MI (US); Michael Chopp, Southfield, MI (US)

(73) Assignee: Henry Ford Health System, Detroit, MI (US)

( * ) Notice: Subject to any disclaimer, the term of this patent is extended or adjusted under 35 U.S.C. 154(b) by 63 days.

This patent is subject to a terminal disclaimer.

(21) Appl. No.: 13/091,028

(22) Filed: Apr. 20, 2011

(65) Prior Publication Data

US 2012/0076759 A1 Mar. 29, 2012

Related U.S. Application Data

(63) Continuation of application No. 11/431,290, filed on May 9, 2006, now Pat. No. 8,017,112, which is a continuation-in-part of application No. 11/027,881, filed on Dec. 30, 2004, which is a continuation-in-part of application No. 09/980,614, filed as application No. PCT/US00/12875 on May 11, 2000, now abandoned.

(60) Provisional application No. 60/134,344, filed on May 14, 1999.

(51) Int. Cl.
 *A61K 35/28* (2006.01)
 *A61P 25/00* (2006.01)
 *A61P 25/28* (2006.01)
 *A61K 38/18* (2006.01)
 *A61K 35/30* (2006.01)

(52) U.S. Cl.
 CPC ............... *A61K 35/30* (2013.01); *A61K 38/18* (2013.01)
 USPC ..................... 424/93.7; 435/368; 514/17.7

(58) Field of Classification Search
 None
 See application file for complete search history.

(56) References Cited

U.S. PATENT DOCUMENTS

| | | | |
|---|---|---|---|
| 4,666,828 A | 5/1987 | Gusella | |
| 4,678,470 A | 7/1987 | Nashef | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,284,761 A | 2/1994 | Aebischer et al. | |
| 5,571,083 A | 11/1996 | Lemelson | |
| 5,690,927 A | 11/1997 | Major et al. | |
| 5,750,376 A | 5/1998 | Weiss et al. | |
| 5,817,773 A | 10/1998 | Wilson et al. | |
| 5,851,832 A | 12/1998 | Weiss et al. | |
| 6,342,479 B1 | 1/2002 | Culler | |
| 6,528,245 B2 | 3/2003 | Sanchez-Ramos et al. | |
| 6,653,134 B2 | 11/2003 | Prockop et al. | |
| 2002/0146821 A1* | 10/2002 | Sanchez-Ramos et al. | .. 435/368 |
| 2003/0039639 A1* | 2/2003 | Prockop et al. | ............ 424/93.21 |
| 2005/0169896 A1 | 8/2005 | Li et al. | |
| 2006/0275272 A1 | 12/2006 | Li et al. | |
| 2007/0264712 A1 | 11/2007 | Savant-Bhonsale | |
| 2009/0162327 A1 | 6/2009 | Li et al. | |

FOREIGN PATENT DOCUMENTS

| | | |
|---|---|---|
| WO | WO 99/43286 A2 | 9/1999 |
| WO | WO 99/56759 A1 | 11/1999 |
| WO | WO 00/50568 A2 | 8/2000 |
| WO | WO 00/69448 A1 | 11/2000 |
| WO | WO 2007/106200 A2 | 9/2007 |

OTHER PUBLICATIONS

Hurwitz et al., Human Gene Therapy, 8:137-156, Jan. 1997.*
Bonn D. The Lancet, 352:119, Jul. 1998.*
Akiyama et al., "Remyelination of the rat spinal cord by transplantation of identified bone marrow stromal cells", *J. Neurosci.*, 22(15):6623-30 (2002).
Aloe et al., "Nerve Growth Factor e Sclerosi Multiple: Studi su Modelli Animali e Nell'Uomo", *Ann. l' Super Sanita*, 40:89-99 (2004). (In Italian).
Aloe et al., "The Expanding Role of Nerve Growth Factor: From Neurotrophic Activity to Immunologic Diseases", *Allergy*, 52:883-894 (1997).
Ausubel et al, *Current Protocols in Molecular Biology*, John Wiley and Sons, Baltimore, Maryland (1989).
Azizi et al., "Engraftment and Migration of Human Bone Marrow Stromal Cells Implanted in the Brains of Albino Rats—Similarities to Astrocyte Grafts", *Proc. Natl. Acad. Sci USA*. 95:3908-3913 (1998).
Bartholomew et al., "Baboon mesenchymal stem cells can be genetically modified to secrete human erythropoietin in vivo", *Hum. Gene Ther.*, 12(12):1527-41 (2001).
Bectold et al., "Axonal Protection Using Flecainide in Experimental Autoimmune Encephalomyelitis", *Ann. Neurol.*, 55:607-616 (2004).
Bennett et al., "Adipocytic Cells Cultured From Marrow Have Osteogenic Potential", *J. Cell. Sci.*, 99:131-139 (1991).
Beresford et al, "Evidence for an Inverse Relationship Between the Differentiation of Adipocytic and Osteogenic Cells in Rat Marrow Stromal Cell Cultures", *J. Cell Sci.*, 102:341-351 (1992).
Birren et al, (eds) *Genome Analysis: A Laboratory Manual Series*, vols. 1-4 Cold Spring Harbor Laboratory Press, New York (1998).
Bjartmar et al., "Axonal Degeneration and Progressive Neurologic Disability in Multiple Sclerosis", *Neurotox. Res.*, 5:157-164 (2003).
Bjartmar et al., "Axonal Loss in the Pathology of MS: Consequences for Understanding the Progressive Phase of the Disease", *J. Neurol. Sci.*, 206:165-171 (2003).

(Continued)

*Primary Examiner* — Jeffrey Stucker
*Assistant Examiner* — Stacey N Macfarlane
(74) *Attorney, Agent, or Firm* — DLA Piper LLP (US)

(57) ABSTRACT

The present invention relates to a treatment of an autoimmune demyelinating disease/disorder. Also included in the present invention is the use of bone marrow stromal cells for the treatment of multiple sclerosis (MS).

17 Claims, 22 Drawing Sheets

(56) References Cited

OTHER PUBLICATIONS

Bjorklund, "Neural Grafting in the Mammalian CNS", *Elsevier Science Publishers B.V. (Biomedical Division)*, Amsterdam, pp. 169-178, 1985.
Bonifer et al., "Developmental Changes in the Differentiation Capacity of Haematopoietic Stem Cells", *Immunol. Today*, 19:236-241, *Journal of Neuroimmunology*, 1998.
Bonini et al., "Nerve Growth Factor: Neurotrophin or Cytokine?", *Int. Arch. Allergy Immunol.*, 131:80-84 (2003).
Bracci-Laudiero et al., "Endogenous NGF Regulates CGRP Expression in Human Monocytes, and Affects HLA-DR and CD86 Expression and IL-10 Production", *Blood*, 106:3507-3514 (2005).
Bracci-Laudiero et al., "NGF Modulates CGRP Synthesis in Human B-Lymphocytes: A Possible anti-Inflammatory Action of NGF?", *Journal of Neuroimmunology*, 123:58-65 (2002).
Burke and Olson, "Preparation of clone libraries in yeast artificial-chromosome vectors in Methods in Enzymology", vol. 194, *Guide to yeast genetics and molecular biology*, eds. C. Guthrie and G. Fink, Academic Press, Inc., Chap. 17, pp. 251-270 (1991).
Burt et al., "Collection of hematopoietic stem cells from patients with autoimmune diseases", *Bone Marrow Transplantation*, 28:1-12 (2001).
Capecchi, "Altering the genome by homologous recombination", *Science*, 244:1288-1292 (1989).
Caplan et al, "Mesenchymal Stem Cells and Gene Therapy", *Clinical Orthopedics and Related Research*, 379:67-570 (2000).
Castro-Malaspina et al., "Characterization of Human Bone Marrow Fibroblast Colony-Forming Cells (CFU-F) and Their Progeny", *Blood*, 56:289-301 (1980).
Chitnis et al, "Therapeutic Strategies to Prevent Neurodegeneration and Promote Regeneration in Multiple Sclerosis" *Curr. Drug Targets Immune Endocr. Metabol. Disord.*, 5:11-26 (2005).
Chopp et al., "Spinal Cord Injury in Rat: Treatment With Bone Marrow Stromal Cell Transplantation", *Neuroreport II*, 11(13):3001-3005 (2000).
Clark et al., "Biology of Bone Marrow Stroma", *Ann. NY Acad. Sci.*, 770:70-78 (1995).
Cohen et al., "Nerve Growth Factor and Neurotrophin-3 Differentially Regulate the Proliferation and Survival of Developing Rat brain Oligodendrocytes", *The Journal of Neuroscience*, 16:6433-6442 (1996).
Colter et al., "Rapid Expansion of Recycling Stem Cells in Cultures of Plastic-Adherent Cells From Human Bone Marrow", *Proc. Natl. Acad Sci USA*, 97:3213-3218 (2000).
Cregg et al, "Recent advances in the expression of foreign genes in *Pichia pastoris*", *Bio/Technology*, 1:905-910 (1993).
Davies et al, "Targeted alterations in yeast artificial chromosomes for inter-species gene transfer", *Nucleic Acids Research*, 20(11):2693-2698 (1992).
Deng et al., "In Vitro Differentiation of Human Marrow Stromal Cells into Early Progenitors of Neural Cells by Conditions That Increase Intracellular Cyclic AMP", *Biochemical Biophysical Research Communication*, 282:148-152 (2001).
Dickinson et al, "High frequency gene targeting using insertional vectors", *Human Molecular Genetics*, 2(8):1299-1302 (1993).
Dixon et al, "A Controlled cortical Impact Model of Traumatic Brain Injury in the Rat", *Journal of Neuroscience Methods*, 39:253-262 (1991).
Duff and Lincoln, "Insertion of a pathogenic mutation into a yeast artificial chromosome containing the human APP gene and expression in ES cells", *Research Advances in Alzheimer's Disease and Related Disorders* (1995).
Eglitis et al., "Hematopoietic Cells Differentiate into Both Microglia and Macroglia in the Brains of Adult Mice", *Proc. Natl. Acad. Sci. USA*, 94:4080-4085 (1997).
Fainzilber et al., "From Neurotrophins to Immunotrophins", *EMBO—European Molecular Biology Organization*, 3(11):1029-1034 (2002).

Ferguson et al., "Axonal Damage in Acute Multiple Sclerosis Lesions", *Brain*, 120(Pt. 3):393-399 (1997).
Flax et al., "Engraftable human neural stem cells respond to developmental cues, replace neurons, and express foreign genes", *Nat. Biotechnol.*, 16(11):1033-9 (1998).
Flugel et al., "Anti-Inflammatory Activity of Nerve Growth Factor in Experimental Autoimmune Encephalomyelitis: Inhibition of Monocyte Transendothelial Migration", *Eur. J. Immuol.*, 31:11-22 (2001).
Friedenstein et al., "The Development of Fibroblast Colonies in Monolayer Cultures of Guinea-Pig Bone Marrow and Spleen Cells", *Cell Tissue Kinet.*, 3:393-403 (1970).
Furlan et al., "Intrathecal Delivery of IFN-y Protects C57BL/6 Mice from Chronic-Progressive Experimental Autoimmune Encephalomyelitis by Increasing Apoptosis of Central Nervous System—Infiltrating Lymphocytes", *Immuol.*, 167:1821-1829 (2001).
Gage, "Discussion Point: Stem Cells of the Central Nervous System", *Curr. Opin. Neurobiol.*, 8:671-676 (1998).
Gilboa et al, "Transfer and expression of cloned genes using retroviral vectors", *BioTechniques*, 4(6):504-512 (1986).
Goto et al., "GABA Receptor Agonist Promotes Reformation of the Striatonigral Pathway by Transplant Derived from Fetal Striatal Primordia in the Lesioned Striatum", *Experiments in Neurology*, 147:503-509 (1997).
Grill et al, :Robust Growth of Chronically Injured Spinal Cord Axons Induced by Grafts of enetically Modified NGF-Secreting Cells, *Experimental Neurology*, 148:444-452 (1997).
Hemmer et al., "New Concepts in the Immunopathogenesis of Multiple sclerosis", *Nature Reviews/Neuroscience*, 3:291-301 (2002).
Ho, Siu-Hong et al, "Induction of NG108-15 cells differentiation by human bone marrow stromal cells", *NeuroReport*, 9:1365-1369 (1998).
Horwitz et al., "Transplantability and Therapeutic Effects of Bone Marrow-Derived Mesenchymal Cells in Children With Osteogenesis Imperfecta", *Nature Medicine*, 5(3):309-313 (1999).
Huston et al, "Protein engineering of single-chain Fv analogs and fusion proteins in Methods in Enzymology", JJ Langone, ed.; *Academic Press*, New York, NY, 203:46-88 (1991).
Huxley et al, "The human HPRT gene on a yeast artificial chromosome is functional when transferred to mouse cells by cell fusion", *Genomics*, 9:742-750 (1991).
Jackowski et al., "Neural Injury Repair: Hope for the Future as Barriers to Effective CNS Regeneration Become Clearer", *British J. Neurosurgery*, 9:303-317 (1995).
Jakobovits et al, "Germ-line transmission and expression of a human-derived yeast artificial chromosome", *Nature*, 362:255-261 (1993).
Johnson and Bird, "Construction of single-chain Fvb derivatives of monoclonal antibodies and their production in *Escherichia coli* in Methods in Enzymology", (JJ Langone, ed.; *Academic Press*, New York, NY) 203:88-99 (1991).
Jones et al, "Axonal Regeneration Through Regions of Chondroitin Sulfate Proteoglycan Deposition After Spinal Cord Injury: A Balance of Permissiveness and Inhibition", *The Journal of Neuroscience*, 23(28):9276-9288 (2003).
Karnezis et al., "The Neurite Outgrowth Inhibitor Nogo A is Involved in Autoimmune-Mediated Demyelination", *Nature Neuroscience*, 7(7):736-744 (2004).
Kempermann et al., "Closer to Neurogenesis in Adult Humans", *Nature Medicine*, 4(5):555-557 (1988).
Kohyama et al., "Brain from Bone: Efficient "Meta Differentiation" of Marrow Stromal-Derived Mature Osteoblasts to Neurons with Noggin or a demethylating agent", *Differentiation*, Oct. 2001, 68(4-5):235-44; Abstract only.
Kopen et al., "Marrow Stromal Cells Migrate Throughout Forebrain and Cerebellum, and They Differentiate Into Astrocytes After Injection Into Neonatal Mouse Brains", *Proc. Natl. Acad. Sci.*, 96:10711-10716 (1999).
Lamb et al, "Introduction and expression of the 400 kilobase precursor amyloid protein gene in transgenic mice", *Nature Genetics*, 5:22-29 (1993).
Laywell et al., "Identification of a multipotent astrocytic stem cell in the immature and adult mouse brain", *Proc. Natl. Acad. Sci. USA*, 97(25):13883-8 (2000).

(56) References Cited

OTHER PUBLICATIONS

Lennon et al., "A Chemically Defined Medium Supports In Vitro Proliferation and Maintains the Osteochondral Potential of Rat Marrow-Derived Mesenchymal Stem Cells", *Exp. Cell Res.*, 219:211-222 (1995).
Li and Chopp, "Marrow stromal cell transplantation in stroke and traumatic brain injury", *Neurosci. Lett.*, 456(3):120-123 (2009).
Liesveld et al, "Adhesive Interactions of Normal and Leukemic Human CD34+ Myeloid Progenitors: Role of Marrow Stromal, Fibroblast, and Cytomatrix Components", *Experimental Hematology*, 19(1):63-70 (1991).
Liesveld et al., "Characterization of Human Marrow Stromal Cells: Role in Progenitor Cell Binding and Granulopoiesis", *Blood*, 73:1794-1800 (1989).
Lozano et al, "A convenient in vitro assay for the inhibition of neurite outgrowth by adult mammalian CNS myelin using immortalized neuronal cells", *Journal of Neuroscience Methods*, 63:23-28 (1995).
Lucchinetti et al, "Heterogeneity of Multiple Sclerosis Lesions: Implications for the Pathogenesis of Demyelination", *Ann. Neurol.*, 47:707-717 (2000).
Mahmood et al., "Long-term recovery after bone marrow stromal cell treatment of traumatic brain injury in rats", *J. Neurosurg.*, 104:272-277 (2006).
Medana et al., "Axonal Damage: A Key Predictor of Outcome in Human CNS Diseases", *Brain*, 126:515-530 (2003).
Mernaugh and Marnaugh, "An overview of phage-displayed recombinant antibodies", in *Molecular Methods in Plant Pathology* (RP Singh and US Singh, eds.; CRC Press Inc., Boca Raton, FL) pp. 359-365 (1995).
Micera et al., "Nerve Growth Factor Antibody Exacerbates Neuropathological Signs of Experimental Allergic Encephalomyelitis in Adult Lewis Rats", *J. Neuroimmunology*, 104:116-123 (2000).
Mishell and Shiigi (eds), "Selected Methods in Cellular Immunology", *W.H. Freeman and Co.*, New York (1980).
Papadaki et al., "Normal bone marrow hematopoietic stem cell reserves and normal stromal cell function support the use of autologous stem cell transplantation in patients with multiple sclerosis", *Bone Marrow Transplantation*, 36:1053-1063 (2005).
PCR Protocols: A Guide to Methods and Applications, *Academic Press*, San Diego, CA (1990).
Pearson and Choi, "Expression of the human b-amyloid precursor protein gene from a yeast artificial chromosome in transgenic mice", *Proc. Natl. Acad. Sci. USA*, 90:10578-82 (1993).
Pereira et al., "Marrow stromal cells as a source of progenitor cells for nonhematopoietic tissues in transgenic mice with a phenotype of osteogenesis imperfecta", *Proc. Natl. Acad. Sci. USA.*, 95(3)1142-7 (1998).
Peterson et al., "Transected Neurites, Apoptotic Neurons, and Reduced Inflammation in Cortical Multiple Sclerosis Lesions", *Ann. Neurol.*, 50(3):389-400 (2001).
Piersma et al., "Characterization of Fibroblastic Stromal Cells from Murine Bone Marrow", *Experimental Hematology*, 13(4):237-243 (1985).
Pluchino et al., "Injection of Adult Neurospheres Induces Recovery in a Chronic Model of Multiple sclerosis", *Nature*, 422:688-694 (2003).
Prockop, "Marrow Stromal Cells as Stem Cells for Nonhematopoietic Tissues", *Science*, 276:71-74 (1997).
Rothstein, "Targeting, disruption, replacement, and allele resuce: integrative DNA transformation in yeast", in Methods in Enzymology, vol. 194, "*Guide to Yeast Genetics and Molecular Biology*," eds. C. Guthrie and G. Fink, Academic Press, Inc., Chap. 19, pp. 281-301 (1991).
Sambrook et al, *Molecular Cloning: A Laboratory Manual*, Cold Spring Harbor Laboratory Press, New York (1989).
Sanchez-Ramos et al., "Adult Bone Marrow Stromal Cells Differentiate Into Neural Cells In Vitro", *Experimental Neurology*, 164:247-256 (2000).
Schedl et al, "A yeast artificial chromosome covering the tyrosinase gene confers copy number-dependent expression in transgenic mice", *Nature*, 362:258-261 (1993).
Schreiner et al., "Modeling multiple sclerosis in laboratory animals", *Semin. Immunopathol.*, 31(4):479-95 (2009).
Schwarz et al., "Multipotential Marrow Stromal Cells Transduced to Produce DOPA: Engraftment in a Rat Model of Parkinson Disease", *Human Gene Therapy*, 10(15):2539-2549 (1999).
Simmons et al., "Identification of Stromal Cell Precursors in Human Bone Marrow bya Novel Monoclonal Antibody, STRO-1", *Blood*, 78(1):55-62 (1991).
Simmons et al., "Dual growth factor delivery and controlled scaffold degradation enhance in vivo bone formation by transplanted bone marrow stromal cells", *Bone*, 35(2):562-9 (2004).
Snyder et al., "Potential of Neural "Stem-Like" Cells for Gene Therapy and Repair of the Degenerating Central Nervous System", *Adv. Neurology*, 72:121-132 (1997).
Stampachiacchiere et al., "Differential Modulatory Effect of NGF on MHC Class I and Class II Expression in Spinal Cord Cells of EAE Rats", *J. Neuroimmunology*, 169:20-30 (2005).
Stites et al, (eds) *Basic and Clinical Immunology* (8 th Edition), Appleton & Lange, Norwalk, CT (1994).
Strauss et al, "Germ line transmission of a yeast artificial chromosome spanning the murine a (1) collagen locus", *Science*, 259:1904-1907 (1993).
Testoni et al., "A new method of "in-cell reverse transcriptase-polymerase chain reaction" for the detection of BCR/ABL transcript in chronic myeloid leukemia patients", *Blood*, 87(9):3822-3827 (1996).
Trapp et al., "Axonal Transection in the Lesions of Multiple Sclerosis", *N. Engl. J. Med.*, 338:278-285 (1998).
Villoslada et al., "Human Nerve Growth Factor Protects Common Marmosets Against Autoimmune Encephalomyelitis by Switching the Balance of T Helper Cell Type 1 and 2 Cytokines Within the Central Nervous System", *J. Exp. Med.*, 191:1799-1806 (2002).
Wakitani et al., "Myogenic Cells Derived From Rat Bone Marrow Mesenchymal Stem Cells Exposed to 5-Azacytidine", *Muscle & Nerve*, 18:1417-1426 (1995).
Walkley et al, Bone marrow transplantation corrects the enzyme defect in neurons of the central nervous system in a lysosomal storage disease, *Proc. Natl. Acad. Sci. USA*, 91:2970-2974, Apr. 1994.
Walsh et al., "Enhanced Neurotrophin-Induced Axon Growth in Myelinated Portions of the CNS in Mice Lacking the p75 Neurotrophin Receptor", *The Journal of Neuroscience*, 19(10):4155-4168 (1999).
Woodbury et al., "Adult Rat and Human Bone Marrow Stromal Cells Differentiate Into Neurons", *Journal of Neuroscience Research*, 61:364-370 (2000).
Wujek et al., "Axon Loss in the spinal Cord Determines Permanent Neurological Disability in an Animal Model of Multiple Sclerosis", *Journal of Neuropathology and Experimental Neurology*, 61(1):23-32 (2002).
Yamaguchi et al., "The effects of neuronal induction on gene expression profile in bone marrow stromal cells (BMSC)—a preliminary study using microarray analysis", *Brain Research*, 1087:15-27 (2006).
Youssef et al., "The HMB-CoA Reductase Inhibitor, Atorvastatin, Promotes a Th2 Bias and Reverses Paralysis in Central Nervous System Autoimmune Disease", *Nature*, 420:78-84 (2002).
Zhang et al., "Human Bone Marrow Stromal Cell Treatment Improves Neurological Functional Recovery in EAE Mice", *Exp. Neurol.*, 195:16-26 (2005).
Zhou et al, "NGF-Induced Axon Growth is Mediated by Localized Inactivation of GSK-3p and Functions of the Microtubule Plus End binding Protein APC", *Neuron*, 42:897-912 (2004).
Simone et al., "Nerve Growth Factor: A Survey of Activity on Immune and Hematopoietic Cells", *Hemet. Onco.* 17:1-10, 1999.

* cited by examiner

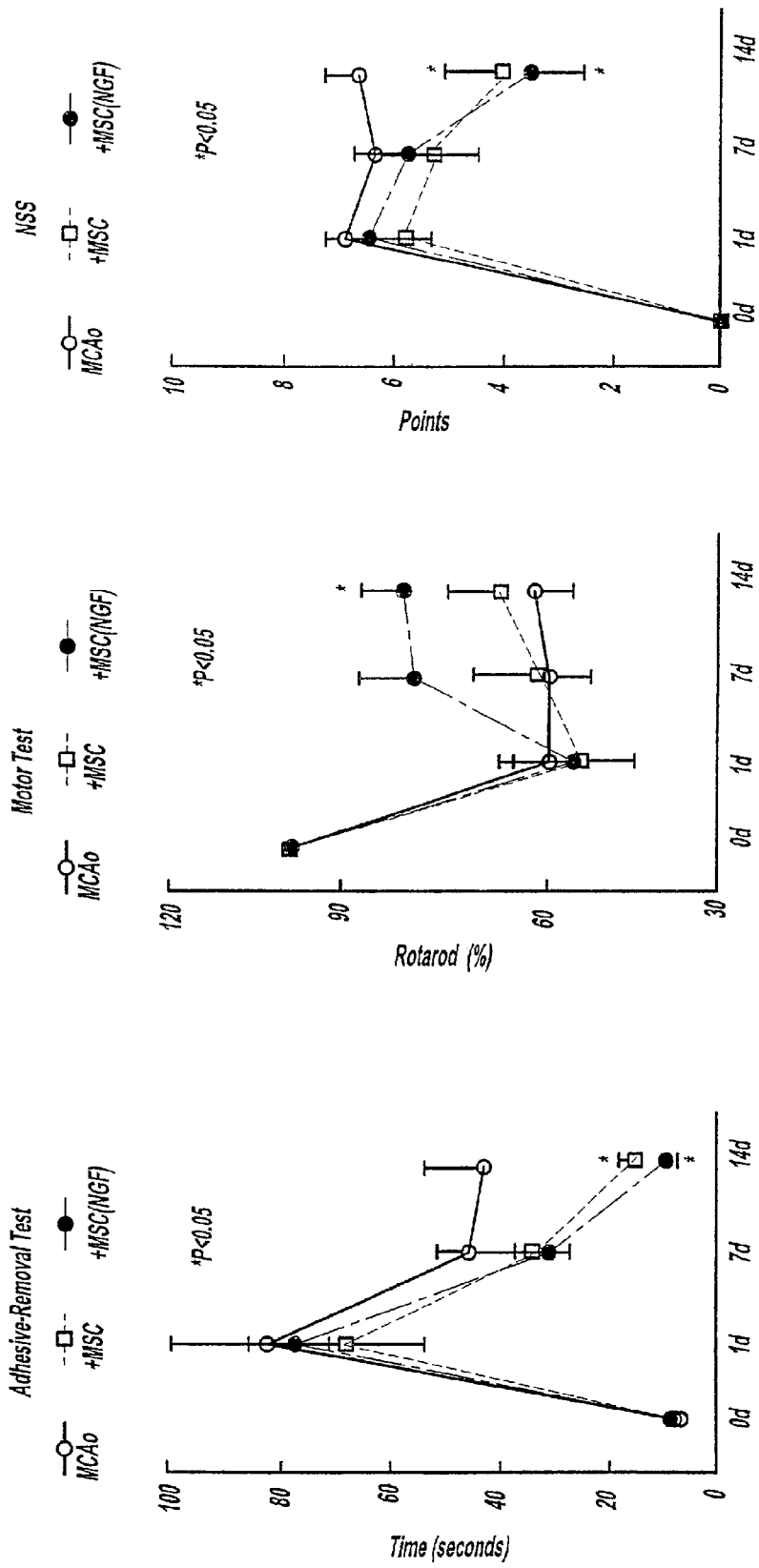

TRANSPLANTATION OF BONE MARROW STROMAL CELLS FOR TREATMENT OF NEURODEGENERATIVE DISEASES

CROSS-REFERENCE TO RELATED APPLICATIONS

The present application is a continuation of U.S. patent application Ser. No. 11/431,290, filed May 9, 2006, which is a continuation-in-part of U.S. patent application Ser. No. 11/027,881, filed Dec. 30, 2004, which is a continuation-in-part of U.S. patent application Ser. No. 09/980,614, filed Apr. 17, 2002, now abandoned, which is a national phase application filed under 35 U.S.C. §371, claiming the benefit of priority of International Application No. PCT/US00/12875, filed May 11, 2000, which claims the benefit under 35 U.S.C. §119(e) of U.S. Provisional Application No. 60/134,344, filed May 14, 1999, all of which are herein incorporated by reference in their entirety.

BACKGROUND OF THE INVENTION

Most central nervous system (CNS) injuries include stroke, trauma, hypoxia-ischemia, multiple sclerosis, seizure, infection, and poisoning directly or indirectly involve a disruption of blood supply to the CNS. These injuries share the same common pathologic process of rapid cerebral edema leading to irreversible brain damage and eventually to brain cell death.

One common injury to the CNS is stroke which is the destruction of brain tissue as a result of intracerebral hemorrhage or ischemia. Stroke may be caused by reduced blood flow or ischemia that results in deficient blood supply and death of tissues in one area of the brain (infarction). The causes of ischemic stroke include blood clots that form in the blood vessels in the brain (thrombus) and blood clots or pieces of atherosclerotic plaque or other material that travel to the brain from another location (emboli). Bleeding (hemorrhage) within the brain may also cause symptoms that mimic stroke.

The CNS tissue is highly dependent on blood supply and is very vulnerable to interruption of blood supply. Without neuroprotection, even a brief interruption of the blood flow to the CNS can cause neurological deficit. The brain is believed to tolerate complete interruption of blood flow for a maximum of about 5 to 10 minutes. It has been observed that after blood flow is restored to areas of the brain that have suffered an ischemic injury, secondary hemodynamic disturbances have long lasting effects that interfere with the ability of the blood to supply oxygen to CNS tissues. Similarly, interruption of the blood flow to the spinal cord, for even short periods of time, can result in paralysis.

Recognition of the "ischemic penumbra," a region of reduced cerebral blood flow in which cell death might be prevented, has focused attention on treatments that might minimize or reverse brain damage when the treatments are administered soon after stroke onset. To date, several classes of neuroprotective compounds have been investigated for acute stroke. They have included calcium channel antagonists, N-methyl-D-aspartate (NMDA) receptor antagonists, free radical scavengers, anti-intercellular adhesion molecule 1 antibody, GM-1 ganglioside, γ-aminobutyric acid agonists, and sodium channel antagonists, among others. Results from various trials have yielded disappointing efficacy results and some evidence of safety problems, including increased mortality or psychotic effects which resulted in their early termination.

Multiple sclerosis (MS) is another disease of the CNS. MS is an inflammatory demyelinating disease, which typically displays a relapsing-remitting course characterized by episodes of neurological disability followed by periods of partial or complete clinical remission (Lucchinetti et al., 2000, *Ann. Neurol.* 47:707-717; Hemmer et al., 2002, *Nat. Rev. Neurosci.* 3:291-301). Most patients later enter a progressive phase of steady decline of neurological function. Severe axonal loss and neuronal death are frequent in MS (Ferguson et al., 1997, *Brain* 120 (Pt. 3):393-399; Trapp et al., 1998, *N. Engl. J. Med.* 338:278-285; Peterson et al., 2001, *Ann. Neurol.* 50:389-400; Bjartmar et al., 2003, *Neurotox. Res.* 5:157-164). Axonal loss is a major cause of permanent neurological deficit in MS (Wujek et al., 2002, *J. Neuropathol. Exp. Neurol.* 61:23-32; Bjartmar et al., 2003, *J. Neurol. Sci.* 206:165-171; Medana et al., 2003, *Brain* 126:515-530). Chronically demyelinated axons may degenerate due to a lack of myelin-derived trophic support (Bjartmar et al., 2003, *J. Neurol. Sci.* 206:165-171); however, no current therapies for MS are known provide at axonal protection (Bectold, et al., 2004, *Ann. Neurol.* 55:607-616).

Cellular therapy serves as an alternative to drug therapy. It has been demonstrated that intracerebral transplantation of donor cells from embryonic tissue may promote neurogenesis (Snyder et al., 1997 Adv Neurol. 72:121-32). Intrastriatal fetal graft has been used to reconstruct damaged basal ganglia circuits and to ameliorate behavioral deficits in a mammalian model of ischemia (Goto et al., 1997 Exp Neurol. 147:503-9). Fetal hematopoietic stem cells (HSCs) transplanted into the adult organism or adult HSCs transplanted into an embryo results in a chimera that reflects the endogenous cells within the microenvironment into which the cells were seeded (Geiger et al., 1998, Immunol Today 19:236-41). Pluripotent stem cells are harbored in the adult CNS and the adult brain can form new neurons (Gage, 1998 Curr. Opin. Neurobiol. 8:671-6; Kempermann and Gage, 1998 Nat Med. 4:555-7).

Bone marrow contains at least two types of stem cells, hematopoietic stem cells and stem cells of non-hematopoietic tissues variously referred to as mesenchymal stem cells or marrow stromal cells (MSCs) or bone marrow stromal cells (BMSCs). These terms are used synonymously throughout herein. MSCs are of interest because they are easily isolated from a small aspirate of bone marrow and they readily generate single-cell derived colonies. The single-cell derived colonies can be expanded through as many as 50 population doublings in about 10 weeks, and can differentiate into osteoblasts, adipocytes, chondrocytes (Friedenstein et al., 1970 Cell Tissue Kinet. 3:393-403; Castro-Malaspina et al., 1980 Blood 56:289-301; Beresford et al., 1992 J. Cell Sci. 102: 341-351; Prockop, 1997 Science 276:71-74), myocytes (Wakitani et al., 1995 Muscle Nerve 18:1417-1426), astrocytes, oligodendrocytes, and neurons (Azizi et al., 1998 Proc. Natl. Acad. Sci. USA 95:3908-3913); Kopen et al., 1999 Proc. Natl. Acad. Sci. USA 96:10711-10716; Chopp et al., 2000 Neuroreport II 3001-3005; Woodbury et al., 2000 Neuroscience Res. 61:364-370). For these reasons, MSCs are currently being tested for their potential use in cell and gene therapy of a number of human diseases (Horwitz et al., 1999 Nat. Med. 5:309-313; Caplan, et al. 2000 Clin. Orthoped. 379:567-570).

MSCs constitute an alternative source of pluripotent stem cells. Under physiological conditions they maintain the architecture of bone marrow and regulate hematopoiesis with the help of different cell adhesion molecules and the secretion of cytokines, respectively (Clark and Keating, 1995 Ann NY Acad Sci 770:70-78). MSCs grown out of bone marrow by their selective attachment to tissue culture plastic can be efficiently expanded (Azizi et al., 1998 Proc Natl Acad Sci USA 95:3908-3913; Colter et al., 2000 Proc Natl Acad Sci USA 97:3213-218) and genetically manipulated (Schwarz et al. 1999 Hum Gene Ther 10:2539-2549).

MSC are also referred to as mesenchymal stem cells because they are capable of differentiating into multiple mesodermal tissues, including bone (Beresford et al., 1992 J Cell Sci 102:341-351), cartilage (Lennon et al., 1995 Exp Cell Res 219:211-222), fat (Beresford et al., 1992 J. Cell. Sci. 102:341-351) and muscle (Wakitani et al., 1995 Muscle Nerve 18:1417-1426). In addition, differentiation into neuron-like cells expressing neuronal markers has been reported (Woodbury et al., 2000 J Neurosci Res 61:364-370; Sanchez-Ramos et al., 2000 Exp Neurol 164:247-256; Deng et al., 2001 Biochem Biophys Res Commun 282:148-152), suggesting that MSC may be capable of overcoming germ layer commitment.

The concept of transplantation of bone marrow has been studied by others. For example, in the Azizi et al. reference, the investigators transplanted human bone marrow stromal cells (hBMSCs) into the brains of albino rats (Azizi et al., 1998 Proc Natl Acad Sci USA 95:3908-3913). Their primary observations were that hBMSCs can engraft, migrate and survive in a manner similar to rat astrocytes. Further, it has been demonstrated that the bone marrow cells when implanted into the brain of adult mice can differentiate into microglia and macroglia (Eglitis et al., Proc Natl Acad Sci USA 1997 94:4080-5). Again, this occurred when the bone marrow cells were transplanted into the brain of normal mice. There have been many attempts made to use bone marrow stromal cells in cell therapy in an animal model. However, there has been little evidence of using bone marrow stromal cells in a diseased animal model or otherwise an animal that is suffering from a disease. Thus, there is a long felt need in the art for efficient and directed means of treating a neurodegenerative disease such as MS in a mammal. The present invention satisfies this need.

BRIEF SUMMARY OF THE INVENTION

According to the present invention, there is provided a method of treating a mammal suffering from a central nervous system (CNS) injury and/or a neurodegenerative disease. The method includes the steps of culturing bone marrow stromal cells and transplanting or otherwise administering the bone marrow stromal cells into the brain of a mammal in need thereof. In addition, the present invention encompasses a composition comprising bone marrow cells and embryonic brain tissue for the use in the treatment of CNS injury and/or neurodegeneration.

Also provided is a method of activating the differentiation of neural cells in an injured brain comprising the steps of transplanting bone marrow stromal cells adjacent to the injured brain cells by way of intravascular (intraarterial, intravenous) administration of the bone marrow stromal cells to the mammal and having the bone marrow stromal cells activate the endogenous central nervous system stem cells to differentiate into neurons.

In another aspect, the invention includes a method of stimulating brain parenchymal cells to express an array of trophic factors including but not limited to NGF, BDNF, VEGF, and bFGF. The method comprises the steps of transplanting bone marrow stromal cells adjacent to the injured brain cells by way of intravascular (intraarterial or intravenous) administration of the bone marrow stromal cells to the mammal. The expression of neurothrophic factors by parenchymal cells stimulated by MSCs provides a therapeutic benefit.

A method of treating injured and degenerative brain using the cells of the present invention is also provided. The method comprises the steps of preparing bone marrow stromal cells and transplanting bone marrow stromal cells near the injured brain cells by way of intravascular administration of the cells.

In addition to using bone marrow stromal cells, whole bone marrow and cellular components of bone marrow have been employed (i.e. mesenchymal stem cells (MSCs); hematopoietic stem cells (HSCs) to treat stroke and traumatic brain injury. Cellular components of bone marrow were cultured in a special medium and in medium comprising neurotrophins (i.e. Nerve Growth Factor (NGF), Brain-derived neurotrophic factor (BDNF)). Cells were injected either directly into the brain, into the internal carotid artery or into a femoral vein. The outcome of having the cells administered into the brain were measured using double staining immunohistochemistry techniques to morphologically identify phenotypic transformation of bone marrow cells, and behavioral and functional tests to identify neurological deficits of the mammal. The data presented herein demonstrate that treatment of among others, stroke, spinal cord injury, or traumatic brain injury with whole bone marrow or cellular components significantly reduces functional deficits. Bone marrow cells also express phenotypes of parenchymal cells.

In addition, mice treated with the neurotoxin 1-methyl-4-phenyl-1,2,3,6-tetrahydropyridine (MPTP) to induce symptoms of Parkinson's disease, were treated with bone marrow cells or bone marrow stromal cells by delivering the cells by the route, including but not limited to, intracerebral and intravascular delivery of the cells to the mammal. Parkinson's symptoms were significantly reduced in mice treated with either bone marrow cells or bone marrow stromal cells. These data demonstrate that these cells can be employed to treat neural injury and neurodegenerative disease.

Furthermore, a mouse experimental autoimmune encephalomyelitis (EAE) model which mimics multiple sclerosis (MS) was employed to demonstrate that administration of bone marrow stromal cell to a mammal in need thereof can treat a neurodegenerative disease associated with demyelination. Accordingly, the invention includes a method of treating a neurodegenerative disease associated with inflammatory demyelination using bone marrow stromal cells. Preferably, the neurodegenerative disease is MS.

Also encompassed in the present invention is a composition comprising an aggregate, composed of neural stem cells from the fetal neurosphere, MSCs from adult bone marrow and cerebro-spinal fluid from adult Wistar rats (called NMC-spheres). These NMCspheres have been successfully used to treat stroke and brain trauma, and can be employed to treat neurodegenerative disease.

Accordingly, the present invention encompasses methods and compositions for the culturing of bone marrow stromal cells in neurotrophins, and the intraparenchymal and intravascular administration of these cells (cultured in the presence or absence of a growth factor), for therapy and the treatment of stroke, trauma and Parkinson's disease using bone marrow. In addition, the cells can be used to treat a neurodegenerative disease associated with demyelination.

The invention relates to a method of treating a mammal having a disease, disorder or condition of the CNS. The method comprises obtaining a bone marrow sample from donor, isolating a stromal cell from the bone marrow sample, and administering the isolated stromal cell to the CNS of the mammal, wherein the presence of the isolated stromal cell in the CNS effects treatment of the disease, disorder or condition.

In one aspect, the presence of the isolated stromal cell in the CNS of the mammal induces angiogenesis. In another aspect, the presence of the isolated stromal cell in the CNS of the mammal induces neurogenesis. In yet another aspect, the presence of the isolated stromal cell in the CNS of the mammal induces synaptogenesis.

In one aspect, the presence of the isolated stromal cell in the CNS of the mammal does not induce an immune response against the stromal cell.

In another aspect, the mammal is a human.

In another aspect, the donor is a human who is not suffering from a disease, disorder or condition of the central nervous system.

In yet another aspect, the human donor is allogeneic, syngeneic or xenogeneic with the human patient.

In a further aspect, the human donor is the human patient.

In one aspect, the disease, disorder or condition of the CNS is selected from the group consisting of a genetic disease, an ischemic induced injury, a spinal cord injury, stroke and Parkinson's disease.

In yet another aspect, the disease, disorder or condition of the CNS is an inflammatory demyelinating disease. More preferably, the disease, disorder or condition of the CNS is MS.

In another aspect, the disease, disorder or condition is injury to the tissues or cells of the CNS. In yet another aspect, the disease, disorder or condition is within the brain of the patient.

In a further aspect, the isolated stromal cell administered to the CNS remains present in the CNS. In another aspect, the isolated stromal cell administered to the CNS replicates in the CNS.

In yet another aspect, the stromal cell administered to the CNS does not result in a cell replacement therapy. Preferably, the stromal cell induces endogenous neighboring cells to express a growth factor. More preferably, the endogenous neighboring cell is a parenchymal or vascular cell.

In yet another aspect, prior to administering the isolated stromal cell, the cell is cultured in vitro.

In one aspect, the isolated stromal cell is administered to the mammal by a route selected from the group consisting of intravascular, intracerebral, parenteral, intraperitoneal, intravenous, epidural, intraspinal, intrasternal, intra-articular, intra-synovial, intrathecal, intra-arterial, intracardiac, and intramuscular.

In another aspect, the isolated stromal cell in the CNS of the mammal secretes a factor selected from the group consisting of a growth factor, a trophic factor and a cytokine. In a further aspect, the secreted factor is selected from the group consisting of leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IGFBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β), vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta (TGFβ-1) and TGFβ-3.

In yet a further aspect, prior to administering the isolated stromal cell, the isolated stromal cell is transfected with an isolated nucleic acid encoding a therapeutic protein, wherein when the protein is secreted by the stromal cell and the secreted protein serves to effect treatment of said disease, disorder or condition.

The invention includes administering an isolated stromal cell to the mammal at the site of injury.

In another aspect, the stromal cell is administered to the mammal at an adjacent site to the site of injury. In one aspect, following administering the stromal cell into the mammal, the stromal cell migrates to the site of injury.

In a further aspect, the stromal cell present in the CNS activates the proliferation of an endogenous neighboring cell. In a further aspect, the endogenous neighboring cell is an astrocyte.

In one aspect, the stromal cell activates the MEK/Akt pathway in neighboring cells. In another aspect, the stromal cell activates the PI3K/Erk pathway in neighboring cells. In a further aspect, the stromal cell activates the differentiation of neighboring cells.

In yet another aspect, the stromal cell exhibits at least one marker characteristic of a cell of the CNS. In further aspect, the marker is selected from the group consisting of class III β-tubulin, the M subunit of neurofilaments, tyrosine hydroxylase, glutamate receptor subunits of the GluR1-4 and GluR6 classes, glial fibrillary acidic protein, myelin basic protein, brain factor 1, NeuN, NF-M, NSE, nestin, and trkA.

The invention includes administering an isolated stromal cell concomitantly with a growth factor to the mammal.

In one aspect, the stromal cell administered to the patient prevents axonal fiber loss in the cells of the mammal.

In another aspect, the stromal cell administered to the patient prevents or reduces demyelination in the cells from the mammal.

The invention includes administering an isolated stromal cell to the mammal in the absence of immunosupppressive agents.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising

FIG. 3, comprising

FIG. 3, comprising

FIG. 4, comprising FIG. 4A through FIG. 4C, depicts data from the adhesive-removal test, the rotarod-motor test and the Neurological Severity Score (NSS), respectively.

FIG. 5, comprising

FIG. 6, comprising

FIG. 12, comprising FIG. 12A demonstrates that the survival rates for hMSCs treated mice at weeks 10, 20, 35, and 45 were significantly higher than those in the PBS group ($p<0.01$). FIG. 12B demonstrates that functional scores were significantly lower among mice treated with hMSCs compared with PBS treated mice as early as 1 week up to 45 weeks ($p<0.05$).

FIGS. 13A through 13D, is a series of images demonstrating that hMSC treatment increases axonal density in the white matter of EAE brain. FIGS. 13A-13B and FIGS. 13C-13D depict reduced area of axonal loss in the striatum and corpus callosum, respectively, between the hMSC treatment group compared with the PBS treatment group.

FIG. 14, comprising FIG. 14A is an image depicting NGF cell expression in the EAE brain treated with hMSCs or PBS. FIG. 14B is a graph depicting increased numbers of NGF reactive cells in the brain at 1, 10, 20, 35 and 45 weeks compared with the PBS treatment. FIG. 14C is an image depicting that about 50-70% of NGF$^+$ cells co-localizes with NeuN$^+$ cells.

FIGS. 16A-16I, is a series of images depicting the phenotype of the transplanted hMSC. FIGS. 16D-16F demonstrates that less than about 5% of MAB1281$^+$ cells co-localized with NG2$^+$ cells. FIGS. 16A-16C and 16C-16I demonstrate that about 10% of MAB1281$^+$ cells co-localized with GFAP$^+$ cells and MAP-2$^+$ cells, respectively.

DETAILED DESCRIPTION OF THE INVENTION

Figure 1A:
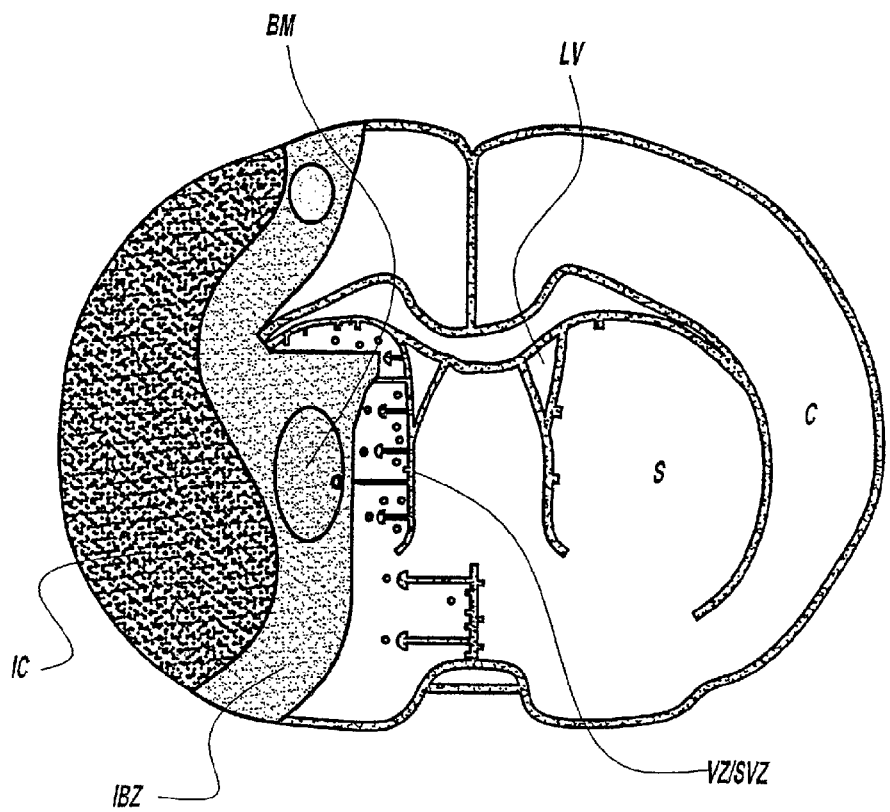
FIG. 1A through FIG. 1B, is a diagram of the three regions of the rat brain after two hours of middle cerebral artery occlusion (MCAo) with bone marrow transplantation.

The present invention provides a method of treating neural injury and neurodegeneration using transplantation of bone marrow stromal cells. It has been determined that bone marrow stromal cells present within injured brain and/or spinal cord produce an array of factors including, but not limited to, cytokines and growth factors. The bone marrow stromal cells activate among others, endogenous stem cells and ependymal cells in the brain, to proliferate and differentiate into parenchymal cells including, but not limited to, neurons. These new neurons can be present at sites adjacent to the sites of injury. Thus, the bone marrow stromal cells activate endogenous CNS stem cells to differentiate into among others, neurons. The bone marrow stromal cells also produce factors including, but not limited to cytokines and growth factors, that promote repair and plasticity of the brain. In addition, the bone marrow stromal cells can induce angiogenesis.

In addition, the invention includes a method of transplanting bone marrow stromal cells to a mammal in need thereof, such as a mammal having MS, where the bone marrow stromal cells induce expression of growth factors within CNS cells. In one aspect, the bone marrow stromal cells stimulate brain parenchymal cells to express NGF. The expression of NGF by the parenchymal cells provides an elevated level of NGF present in the CNS that otherwise would be at a lower level in the absence of bone marrow stromal cells. The elevated level of NGF present in the CNS provides a therapeutic benefit, including but not limited to stimulating axonal repair, prevent demyelination, reducing axonal loss, stimulating oligodendrocyte growth, stimulated oligodendrocyte differentiation, enhancing survival of differentiated oligodendrocytes, and exhibiting immunomodulatory effects. Therefore, in some instances, the therapeutic effect from transplantation of bone marrow stromal cell is not due to cell replacement therapy where the transplanted bone marrow stromal cells differentiate into neuronal cells for replacement of damaged endogenous neuronal cells, but rather the interaction with endogenous cells to induce endogenous cells to secrete growth factors such as NGF.

The present invention encompasses methods of culturing bone marrow stromal cells, and methods for administering the cells of the present invention to a mammal. The cells can be transplanted into the penumbral tissue, which is a tissue adjacent to a lesion. The tissue adjacent to the lesion provides a receptive environment, similar to that of a developmental brain, for the survival and differentiation of the bone marrow stromal cells. It is based on this activity that the bone marrow stromal cells are useful in treating neural injury and neurodegeneration wherein brain and/or spinal cord damage has occurred.

In addition, bone marrow stromal cells are effective in treating neural injury and degeneration when these cells are administered intravascularly, i.e. intraarterially or intravenously. Therefore, after such brain injury, when the brain tissue is damaged, in an effort to compensate for the lost tissue, the administration of bone marrow stromal cells can provide a sufficient source of cells to promote compensatory responses of the brain to such damage.

The cells of the present invention can be administered into including, but not limited to ischemic brain, injured brain, injured spinal cord and into brain that exhibits symptoms of Parkinson's disease. In some instances, the cells are administered to a brain of a mammal that exhibits symptoms of MS. In any event, transplantation of the cells into the brain can also be performed with co-transplantation of growth factors including, but not limited to brain derived neurotrophic factor (BDNF) and nerve growth factor (NGF). The cells of the invention are cultured with NGF prior to transplantation into a recipient.

Transplantation can be performed at various time points (i.e., from four hours to two days after stroke, from one to seven days after trauma, seven days after spinal cord injury and fourteen days after initiation of Parkinson's disease) after experimental stroke in both the rat and the mouse. The data presented herein indicate that the transplantation of bone marrow or components into ischemic brain results in differentiation of the bone marrow cells into the brain parenchymal cells, including but not limited to neurons. In addition, endogenous brain stem cells are activated to proliferate and differentiate into parenchymal cells. The cells of the invention migrate to different regions within the brain including, but not limited to, the hippocampus, the olfactory bulb and the cortex. There is also improved functional outcome in rats treated with bone marrow transplantation cultured with or in combination with growth factors. The disclosure herein demonstrates that the cells of the invention can also be used to provide improved functional outcomes in higher mammals, including but not limited to humans.

The disclosure presented herein also indicates that the transplantation of bone marrow stromal cells into a brain of a mammal that exhibits characteristics of MS or otherwise a mammal suffering from immune-mediated demyelination, reduces axonal loss in the brain. In addition, the transplantation of bone marrow stromal cells contributes to expression of NGF from endogenous parenchymal cells. The secretion of NGF by endogenous parenchymal provides both neurotrophic and immunomodulatory effects.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the term "autologous" is meant to refer to any material derived from the same individual to which it is later to be re-introduced into the individual.

As used herein, the term "allogeneic" is meant to refer to any material derived from a different mammal of the same species.

"Xenogeneic" refers to any material derived from a mammal of a different species.

As used herein, the term "bone marrow stromal cells (BM-SCs)," "stromal cells," "mesenchymal stem cells" or "MSCs" are used interchangeably and refer to the small fraction of cells in bone marrow which can serve as stem cell-like precursors to osteocytes, chondrocytes, and adipocytes. Bone marrow stromal cells have been studied extensively (Castro-Malaspina et al., 1980, Blood 56:289-30125; Piersma et al., 1985, Exp. Hematol 13:237-243; Simmons et al., 1991, Blood 78:55-62; Beresford et al., 1992, J. Cell. Sci. 102: 341-3 51; Liesveld et al., 1989, Blood 73:1794-1800; Liesveld et al., Exp. Hematol 19:63-70; Bennett et al., 1991, J. Cell. Sci. 99:131-139). Bone marrow stromal cells may be derived from any animal. In some embodiments, stromal cells are derived from humans.

"Differentiation medium" is used herein to refer to a cell growth medium comprising an additive or a lack of an additive such that a stem cell, embryonic stem cell, ES-like cell, MSCs, neurosphere, NSC or other such progenitor cell, that is not fully differentiated when incubated in the medium, develops into a cell with some or all of the characteristics of a differentiated cell.

As used herein, the term "disease, disorder or condition of the central nervous system" is meant to refer to a disease, disorder or a condition which is caused by a genetic mutation in a gene that is expressed by cells of the central nervous system such that one of the effects of such a mutation is manifested by abnormal structure and/or function of the central nervous system, such as, for example, neurodegenerative disease or primary tumor formation. Such genetic defects may be the result of a mutated, non-functional or under-expressed gene in a cell of the central nervous system. The term should also be construed to encompass other pathologies in the central nervous system which are not the result of a genetic defect per se in cells of the central nervous system, but rather are the result of infiltration of the central nervous system by cells which do not originate in the central nervous system, for example, metastatic tumor formation in the central nervous system. The term should also be construed to include trauma to the central nervous system induced by direct injury to the tissues of the central nervous system. The term should also include a neurodegenerative disease associated with demyelination of cells of the CNS. An example of such a disease is multiple sclerosis (MS).

"Neural stem cell" or "NSC" is used herein to refer to undifferentiated, multipotent, self-renewing neural cell. A neural stem cell is a clonogenic multipotent stem cell which is able to divide and, under appropriate conditions, has self-renewal capability and can terminally differentiate into among others, neurons, astrocytes, and oligodendrocytes. Hence, the neural stem cell is "multipotent" because stem cell progeny have multiple differentiation pathways. A neural stem cell is capable of self maintenance, meaning that with each cell division, one daughter cell will also be, on average, a stem cell.

"Neurosphere" is used herein to refer to a neural stem cell/progenitor cell wherein Nestin expression can be detected, including, inter alia, by immunostaining to detect Nestin protein in the cell. Neurospheres are aggregates of proliferating neural stem and progenitor cells and the formation of neurosphere is a characteristic feature of neural stem cells in in vitro culture.

As used herein, "central nervous system" should be construed to include brain and/or the spinal cord of a mammal. The term may also include the eye and optic nerve in some instances.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

The phrase "substantially homogeneous population of cells" as used herein should be construed to mean a population of cells wherein at least 75% of the cells exhibit the same phenotype.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered. Also, as used herein, a "therapeutically effective amount" is the amount of cells which is sufficient to provide a beneficial effect to the subject to which the cells are administered.

Description

The present invention is based on the discovery that MSCs can differentiate into neurons and other parenchmal cells. In addition, the present invention is based on the discovery that MSCs can secrete a factor including, but not limited to NGF, BDNF, VEGF, and bFGF, that is beneficial to neighboring and/or distal cells. The disclosure herein demonstrates that when MSCs are introduced into a mammal, the MSCs activate endogenous cells to proliferate and differentiate. In some instances, the MSCs induce endogenous cells to express NGF. Preferably, the endogenous cells express and secrete NGF.

The present disclosure also demonstrates that MSCs when introduced to a site, or near a site of brain injury and/or spinal cord injury, produce and secrete an array of factors including, but not limited to trophic factors, cytokines and growth factors. The factors secreted by the MSCs serve to activate, among others, endogenous stem cells and subepedymal/epedymal cells in the brain and/or spinal cord to proliferate and differentiate into parenchymal cells, including, but not limited to neurons. Thus, the present invention includes a method of using MSCs to promote repair and plasticity of a CNS tissue in a mammal including, but not limited to brain and spinal cord that has undergone disease, disorder or condition associated with a defect in the CNS. Preferably, the disease is MS.

The cells of the present invention can also be used to secrete an angiogenic factor including, but not limited to vascular growth factor, endothelial cell growth factor, and the like. MSCs can be used to induce angiogenesis within the tissue in which the MSCs are present. Thus, the invention provides a method of promoting neovascularization within a tissue using such cells. In accordance with this method, the cells are introduced to the desired tissue under conditions sufficient for the cell to produce the angiogenic factor. The presence of the factor within the tissue promotes neovascularization within the tissue.

The mode of administration of the cells of the invention to the CNS of the mammal may vary depending on several factors including the type of disease being treated, the age of the mammal, whether the cells are differentiated or not, whether the cells have heterologous DNA introduced therein, and the like. An example of administration of the cells into a brain tissue is provided herein in the experimental Examples section. In that example, cells are introduced into the brain of a mammal by intracerebral or intravascular transplantation. Cells may be introduced to the desired site by direct injection, or by any other means used in the art for the introduction of compounds into the CNS.

The cells can be administered into a host in a wide variety of ways. Preferred modes of administration are intravascular, intracerebral, parenteral, intraperitoneal, intravenous, epidural, intraspinal, intrasternal, intra-articular, intra-synovial, intrathecal, intra-arterial, intracardiac, or intramuscular. In some embodiments, MSCs are administered to the brain by direct transplantation as described herein in the experimental Examples section. In other embodiments, MSCs are administered to the central nervous system, i.e., the spinal cord, by simple injection.

Transplantation of the cells of the present invention can be accomplished using techniques well known in the art as well as those described herein or as developed in the future. The present invention comprises a method for transplanting, grafting, infusing, or otherwise introducing the cells into a mammal, preferably, a human. Exemplified herein are methods for transplanting the cells into brains of various mammals, but the present invention is not limited to such anatomical sites or to those mammals. Also, methods for bone transplants are well known in the art and are described in, for example, U.S. Pat. No. 4,678,470, pancreas cell transplants are described in U.S. Pat. Nos. 6,342,479, and 5,571,083, teaches methods for transplanting cells to any anatomical location in the body.

In order to transplant the cells of the present invention into a mammal, for example a rat, the rat is anesthetized, preferably with approximately 3.5% halothane, and anesthesia is maintained with 1.0% halothane in 70% $N_2O$ and 30% $O_2$ or any cocktail well known in the art. The rat is then positioned on a stereotaxic instrument. A midline incision is made in the scalp and a is hole drilled for the injection of the cells. Rats receive implants of the cells into the right striatum using a glass capillary attached to a 10 μl Hamilton syringe. Each rat receives a total of about $1\times10^5$ cells. Following implantation, the skin was sutured closed with either thread or staples. After recovery, the rats are behaviorally tested and sacrificed for histological and immunological analysis to determine the rate of differentiation of both the implanted cell and the endogenous cells of the CNS in vivo.

The cells of the present invention can be transplanted into a human. Preferably, the cells are from the patient for which the cells are being transplanted into (autologous transplantation). One preferable mode of administration is as follows. In the case where cells are not from the patient (allogeneic transplantation), at a minimum, blood type or haplotype compatibility should be determined between the donor cell and the patient. Surgery is performed using a Brown-Roberts-Wells computed tomographic (CT) stereotaxic guide. The patient is given local anesthesia in the scalp area and intravenously administered midazolam. The patient undergoes CT scanning to establish the coordinates of the region to receive the transplant. The injection cannula usually consists of a 17-gauge stainless steel outer cannula with a 19-gauge inner stylet. This is inserted into the brain to the correct coordinates, then removed and replaced with a 19-gauge infusion cannula that has been preloaded with about 30 μl of tissue suspension. The cells are slowly infused at a rate of about 3 μl/min as the cannula is withdrawn. Multiple stereotactic needle passes are made throughout the area of interest, approximately 4 mm apart. The patient is examined by CT scan postoperatively for hemorrhage or edema. Neurological evaluations are performed at various post-operative intervals, as well as PET scans to determine metabolic activity of the implanted cells.

Between about $10^5$ and about $10^{13}$ cells per 100 kg person are administered to a human per infusion. In some embodiments, between about $1.5\times10^6$ and about $1.5\times10^{12}$ cells are infused per 100 kg person. In some embodiments, between about $1\times10^9$ and about $5\times10^{11}$ cells are infused per 100 kg person. In some embodiments, between about $4\times10^9$ and about $2\times10^{11}$ cells are infused per 100 kg person. In some embodiments, between about $5\times10^8$ cells and about $1\times10^{10}$ cells are infused per 100 kg person.

In some embodiments, a single administration of cells is provided. In some embodiments, multiple administrations are provided. In some embodiments, multiple administrations are provided over the course of 3-7 consecutive days. In some embodiments, 3-7 administrations are provided over the course of 3-7 consecutive days. In some embodiments, 5 administrations are provided over the course of 5 consecutive days.

In some embodiments, a single administration of between about $10^5$ and about $10^{13}$ cells per 100 kg person is provided. In some embodiments, a single administration of between about $1.5\times10^8$ and about $1.5\times10^{12}$ cells per 100 kg person is provided. In some embodiments, a single administration of between about $1\times10^9$ and about $5\times10^{11}$ cells per 100 kg person is provided. In some embodiments, a single administration of about $5\times10^{10}$ cells per 100 kg person is provided. In some embodiments, a single administration of $1\times10^{10}$ cells per 100 kg person is provided.

In some embodiments, multiple administrations of between about $10^5$ and about $10^{13}$ cells per 100 kg person are provided. In some embodiments, multiple administrations of between about $1.5\times10^8$ and about $1.5\times10^{12}$ cells per 100 kg person are provided. In some embodiments, multiple administrations of between about $1\times10^9$ and about $5\times10^{11}$ cells per 100 kg person are provided over the course of 3-7 consecutive days. In some embodiments, multiple administrations of about $4\times10^9$ cells per 100 kg person are provided over the course of 3-7 consecutive days. In some embodiments, multiple administrations of about $2\times10^{11}$ cells per 100 kg person are provided over the course of 3-7 consecutive days. In some embodiments, 5 administrations of about $3.5\times10^9$ cells are provided over the course of 5 consecutive days. In some embodiments, 5 administrations of about $4\times10^9$ cells are provided over the course of 5 consecutive days. In some embodiments, 5 administrations of about $1.3\times10^{11}$ cells are provided over the course of 5 consecutive days. In some embodiments, 5 administrations of about $2\times10^{11}$ cells are provided over the course of 5 consecutive days.

In a one embodiment of the invention, the cells of the present invention are administered to a mammal suffering from a disease, disorder or condition involving the CNS, in order to augment or replace the diseased and damaged cells of the CNS. MSCs are preferably administered to a human suffering from a disease, disorder or condition involving the CNS. The MSCs are further preferably administered to the brain or spinal cord of the human. In some instances, the cells are administered to the adjacent site of injury in the human brain. The precise site of administration of the cells depend on any number of factors, including but not limited to, the site of the lesion to be treated, the type of disease being treated, the age of the human and the severity of the disease, and the like. Determination of the site of administration is well within the skill of the artisan versed in the administration of such cells. Based on the present disclosure, the cells can be administered to the patient via intracarotid or intravenous routes.

In another embodiment, the therapeutic benefit of administering bone marrow stromal cells to a mammal in need thereof is not the result of a cell replacement therapy. That is, the administered bone marrow stromal cells provide a therapeutic benefit by inducing endogenous CNS cells to express and secrete a growth factor. In one aspect, the bone marrow stromal cells stimulate brain parenchymal cells to express and secrete a factor including, but not limited to NGF, BDNF, VEGF, and bFGF. By way of example, the expression and secretion of NGF by the parenchymal cells provides an elevated level of NGF compared to the level of NGF present in an otherwise identical CNS not treated with bone marrow stromal cells. In any event, the elevated level of NGF present in the CNS provides a therapeutic benefit, including but not limited to stimulating axonal repair, prevent demyelination, reducing axonal loss, stimulating oligodendrocyte growth, stimulated oligodendrocyte differentiation, enhancing survival of differentiated oligodendrocytes, and exhibiting immunomodulatory effects.

There are several ways in which MSCs can be used in a mammal, preferably, a human, to treat diseases of the central nervous system. For example, the cells can be used as precursor cells that differentiate following introduction into the CNS or as cells which have been differentiated into neural cells prior to introduction into the CNS. In either situation, the cells can be differentiated to express at least one characteristic of a cell of the CNS including, but not limited to class III β-tubulin, the M subunit of neurofilaments, tyrosine hydroxylase, glutamate receptor subunits of the GluR1-4 and GluR6 classes, glial fibrillary acidic protein, myelin basic protein, brain factor 1, NeuN, NF-M, NSE, nestin, and trkA.

The data presented herein establish that MSCs, when transplanted into a mammal, express proteins characteristic of astrocytes (positive for glial fibrillary acidic protein, GFAP, a marker for early astrocytes) and neurons (positive for microtubule associate protein-2, MAP-2, a marker for neurons). It is anticipated that MSCs which are introduced into the CNS can differentiate into other cell types including, but not limited to oligodendrocytes, Schwann cells and parenchymal cells.

Further, the disclosure herein demonstrates that following introduction of MSCs into a mammal, the cells can secrete various factors. Such factors include, but are not limited to, growth factors, trophic factors and cytokines. In some instances, the secreted factors can have a therapeutic effect in the mammal. The secreted factors can activate the cell from which the factor was secreted from. In addition, the secreted factor can activate neighboring and/or distal endogenous cells to proliferate and/or differentiate. Preferably an MSC secretes a cytokine or growth factor such as human growth factor, fibroblast growth factor, nerve growth factor, insulin-like growth factors, hemopoietic stem cell growth factors, members of the fibroblast growth factor family, members of the platelet-derived growth factor family, vascular and endothelial cell growth factors, members of the TGFβ family (including bone morphogenic factor), or enzymes specific for congenital disorders.

MSCs can also secrete factors, trophic factors, and cytokines including, but not limited to, leukemia inhibitory factor (LIF), brain-derived neurotrophic factor (BDNF), epidermal growth factor receptor (EGF), basic fibroblast growth factor (bFGF), FGF-6, glial-derived neurotrophic factor (GDNF), granulocyte colony-stimulating factor (GCSF), hepatocyte growth factor (HGF), IFN-γ, insulin-like growth factor binding protein (IGFBP-2), IGFBP-6, IL-1ra, IL-6, IL-8, monocyte chemotactic protein (MCP-1), mononuclear phagocyte colony-stimulating factor (M-CSF), neurotrophic factors (NT3), tissue inhibitor of metalloproteinases (TIMP-1), TIMP-2, tumor necrosis factor (TNF-β) vascular endothelial growth factor (VEGF), VEGF-D, urokinase plasminogen activator receptor (uPAR), bone morphogenetic protein 4 (BMP4), IL1-a, IL-3, leptin, stem cell factor (SCF), stromal cell-derived factor-1 (SDF-1), platelet derived growth factor-BB (PDGFBB), transforming growth factors beta TGFβ-1 and TGFβ-3.

The data presented herein establishes that the cells can successfully graft to the CNS tissue. Further, the cells can migrate to different regions within the brain including, but not limited to hippocampus, olfactory bulb and cortex. These cells may therefore replace cells in the CNS which have been lost as a result of a genetic disease, trauma, or other injury. Further, these cells can activate endogenous cells to proliferate and/or differentiate.

In addition, prior to the introduction of the cells into the CNS, the cells may be genetically engineered to produce molecules such as trophic factors, growth factors, cytokines, neurotrophins, and the likes, which are beneficial to cells which are already present in the CNS. For example, MSCs can be cultured and genetically engineered cells prior to their introduction into a recipient, and following the introduction of the engineered cell into the recipient, the cells are able to repair the defected CNS tissue.

Based on these considerations, the types of diseases which are treatable using the cells of the present are limitless. For example, among neonates and children, the cells may be used for treatment of a number of genetic diseases of the CNS, including, but not limited to, Tay-Sachs disease and the related Sandhoffs disease, Hurler's syndrome and related mucopolysaccharidoses and Krabbe's disease. To varying extents, these diseases also produce lesions in the spinal cord and peripheral nerves. In addition, in neonates and children, treatment of head trauma during birth or following birth is treatable by introducing the cells into the CNS of the individual. CNS tumor formation in children is also treatable using the methods of the present invention.

With respect to adult diseases of the CNS, the cells of the present invention are useful for treatment of Parkinson's disease, Alzheimer's disease, spinal cord injury, stroke, trauma, tumors, degenerative diseases of the spinal cord such as amyotropic lateral sclerosis, Huntington's disease, epilepsy and the like. Treatment of multiple sclerosis may also be possible.

Other neurodegenerative diseases include but are not limited to, AIDS dementia complex; demyelinating diseases, such as multiple sclerosis and acute transferase myelitis; extrapyramidal and cerebellar disorders, such as lesions of the ecorticospinal system; disorders of the basal ganglia or cerebellar disorders; hyperkinetic movement disorders, such as Huntington's Chorea and senile chorea; drug-induced movement disorders, such as those induced by drugs that block CNS dopamine receptors; hypokinetic movement disorders, such as Parkinson's disease; progressive supra-nucleopalsy; structural lesions of the cerebellum; spinocerebellar degenerations, such as spinal ataxia, Friedreich's ataxia, cerebellar cortical degenerations, multiple systems degenerations (Mencel, Dejerine Thomas, Shi-Drager, and Machado-Joseph), systermioc disorders, such as Rufsum's disease, abetalipoprotemia, ataxia, telangiectasia; and mitochondrial multi-system disorder; demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Demetia of Lewy body type; Wernicke-Korsakoff syndrome; chronic alcoholism; Creutzfeldt-Jakob disease; Subacute sclerosing panencephalitis hallerrorden-Spatz disease; and Dementia pugilistica. See, e.g., Berkow et. al., (eds.) (1987), The Merck Manual, (15$^{th}$ edition), Merck and Co., Rahway, N.J., which reference, and references cited therein, are entirely incorporated herein by reference.

In some aspects of the invention, an individual suffering from a disease, disorder, or a condition that affects the CNS that is characterized by a genetic defect may be treated by supplementing, augmenting and/or replacing defective or deficient neurological cells with cells that correctly express a normal neurological cell gene. The cells which are to be introduced into the individual may be derived from a different donor (allogeneic) or they may be cells obtained from the individual to be treated (autologous). In addition, the cells to be introduced into the individual can by obtained from an entirely different species (xenogeneic). The cells may also be genetically modified to correct the defect. But this is not the only instance where the cells can be genetically modified.

In another aspect of the invention, an individual suffering from a disease, disorder or a condition of the central nervous system can be treated as follows. Isolated MSCs are obtained and expanded in culture. The cells are then administered to the individual in need thereof. It is envisioned that some of the isolated/expanded cells that are administered to the individual develops into normal cells of the central nervous system. Thus, repopulation of the central nervous system tissue with an expanded population of MSCs serves to provide a population of normal central nervous system cells which facilitate correction of the defect in the central nervous system tissue. In addition, the cells that are introduced into the individual can secrete agents including, but not limited to growth factors, trophic factors, cytokines and the like to activate endogenous cells of the individual to proliferate and differentiate.

Based upon the disclosure herein, it is envisioned that the MSCs of the present invention can be administered to the individual in need thereof without the requirement of using immunosuppressive drug therapy. It is recognized that cells from disparate individuals invariably results in the risk of graft rejection. However, it was observed that MSCs did not induce an immune response when the cells were administered to an allogeneic recipient. Further, it was observed that the presence of an immunosuppressive drug, for example cyclosporine A (CsA) during transplantation of MSCs to an allogeneic mammal, did not contribute anymore significant effects on neurological functional recovery compared to when MSCs were administered to an otherwise identical mammal without receiving an immunosuppressive drug. Therefore, as more fully discussed elsewhere herein, an aspect of the invention includes using allogeneic MSCs for transplantation.

The invention also includes methods of using MSCs of the present invention in conjunction with current mode, for example the use of immunosuppressive drug therapy, for the treatment of host rejection to the donor tissue or graft versus host disease. An advantage of using MSCs in conjunction with immunosuppressive drugs in transplantation is that by using the methods of the present invention to ameliorate the severity of the immune response following transplantation, the amount of immunosuppressive drug therapy used and/or the frequency of administration of immunosuppressive drug therapy can be reduced. A benefit of reducing the use of immunosuppressive drug therapy is the alleviation of general immune suppression and unwanted side effects associated with immunosuppressive drug therapy.

In another aspect of the invention, the cells are pre-differentiated into, for example, neurons prior to administration of the cells into the individual in need thereof. MSCs can be differentiated in vitro by treating the cells with differentiation factors including, but are not limited to antioxidants, epidermal growth factor (EGF), and brain derived neurotrophic factor (BDNF). It has been demonstrated that treatment of the cells with these factors induced the cells to undergo morphologic changes consistent with neuronal differentiation, i.e., the extension of long cell processes terminating in growth cones and filopodia. In addition, it was observed that these agents induced the expression of neuronal specific proteins including, but are not limited to nestin, neuron-specific enolase (NSE), neurofilament M (NF-M), neuron-specific nuclear protein (NeuN), and the nerve growth factor receptor trkA.

Treating CNS Disorders

Treating a human patient having a disease, disorder, or a condition that affects the CNS, encompasses among others, intracerebral grafting of MSCs or MSC-differentiated cells to the CNS, including the region of the CNS having the injury or a region adjacent to the site of injury. MSC-differentiated cells include, for example, oligodendrocyte precursors that have been differentiated by culturing MSCs in a differentiation medium. The cells of the invention can be injected into a number of sites, including the intraventricular region, the parenchyma (either as a blind injection or to a specific site by stereotaxic injections), and the subarachnoid or subpial spaces. Specific sites of injection can be portions of the cortical gray matter, white matter, basal ganglia, and spinal cord. Without wishing to be bound to any particular theory, any mammal affected by a CNS disorder, as described elsewhere herein, can be so treated by one or more of the methodologies described herein.

Conventional techniques for grafting are described, for example, in Bjorklund and Stenevi (1985, Neural Grafting in the Mammalian CNS, eds. Elsevier, pp 169-178), the contents of which are incorporated by reference. Procedures include intraparenchymal transplantation, achieved by injecting the cells of the invention into the host brain tissue. However, transplantation of the cells of the invention can be effected in a number of CNS regions.

According to the present invention, administration of cells into selected regions of a patient's brain may be made by drilling a hole and piercing the dura to permit the needle of a microsyringe to be inserted. Alternatively, the cells can be injected intrathecally into a spinal cord region. The cell preparation of the invention permits grafting of the cells to any predetermined site in the brain or spinal cord. It also is possible to effect multiple grafting concurrently, at several sites, using the same cell suspension, as well as mixtures of cells.

The data disclosed herein demonstrate the effects of administering the cells of the present invention to a mammal that has undergone a disease, disorder, or a condition that affects the CNS, otherwise a CNS injury, for example stroke using intraarterial (IA) or intravenous (IV) delivery systems. The effects of MSCs injected via IA or IV in an injured mammal was assessed by analyzing neurological function, neurogenesis, and angiogenesis in mammals that were subjected to ischemic conditions. Quantitative analysis using immunohistochemistry techniques indicated that angiogenesis was significantly enhanced by the administration of the cells of the present invention. The data disclosed herein demonstrated that no significant differences were observed with respect to neurological function, neurogenesis, and angiogenesis in mammals that received either IA or IV administration of the cells. Based on the present disclosure, MSCs delivered to the ischemic brain through both intracarotid and intravenous routes provide therapeutic benefits to a mammal that has undergone stroke. However, the invention should in no way be construed to be limited to any one method of administering MSCs. Rather, any method of administration of the cells should be construed to be included in the present invention. Further, the invention should in no way be limited to stroke, rather, any disease, disorder or condition of the CNS can be treated using compositions and methods of the present invention.

Treatment of a patient, according to the invention, can take advantage of the migratory ability of MSCs, and using them to provide a peptide, protein or other substance to a region of the CNS affected by a dysfunction or deficiency relating to that substance. As such, the cells of the invention may contain exogenous DNA encoding a product that is missing in an individual suffering from a CNS disorder. For example, the DNA can code for a transmitter, such as acetylcholine or GABA, or a receptor for such a transmitter. If an individual is suffering from a glutamate-induced injury, it may be desirable to introduce into the patient a gene coding for a glutamate transporting protein, which can reduce glutamate-induced cytotoxicity.

In a further approach, DNA that encodes a growth factor or a cytokine can be transfected to MSCs, which then are administered to a patient suffering from a CNS disorder, the etiology or elaboration of which is associated with a deficit or dysfunction in the gene expression product. To this end, the invention includes, for example, the use of a gene that, upon expression, produces factors including, but are not limited to NGF, brain-derived neurotrophic factor (BDNF), glial cell line-derived neurotrophic factor (GDNF), insulin-like growth factor (IGF-1) and ciliary neurotrophic factor (CNTF). In addition, the selected gene can encode leukemia inhibitory factor (LIF) or any other of the other cytokines, disclosed, for example, by Reichardt et al. (1997, Molecular and Cellular Approaches to Neural Development, Oxford University Press: 220-263), supra, that promotes cell survival or differentiation.

A therapeutic procedure according to the present invention can be effected by injecting cells, preferably stereotaxically, into the cortex or the basal ganglia. Thereafter, the diffusion and uptake of a ligand secreted by an MSC is beneficial in alleviating the symptoms of a disorder where the subject's neural cells are defective in the production of such a gene product. Thus, an MSC genetically modified to secrete a neurotrophic factor, such as nerve growth factor (NGF), is used to prevent degeneration of cholinergic neurons that might otherwise die without treatment. Alternatively, MSCs to be grafted into a subject with a disorder characterized by a loss of dopamine neurons, such as Parkinson's disease, can be modified to contain exogenous DNA encoding L-DOPA, the precursor to dopamine.

According to the present invention, other CNS disorders likewise can be treated, including Alzheimer's disease, ganglioside storage diseases, CNS damage due to stroke, and damage in the spinal cord. For example, Alzheimer's disease is characterized by degeneration of the cholinergic neurons of the basal forebrain. The neurotransmitter for these neurons is acetylcholine, which is necessary for their survival. Engraftment of an MSC containing an exogenous gene encoding for a factor that would promote survival of these neurons, can be accomplished by the method of the invention described herein.

The use of MSCs for the treatment of a disease, disorder, or a condition that affects the CNS provides an additional advantage in that the MSCs can be introduced into a recipient without the requirement of an immunosuppressive agent. Successful transplantation of a cell is believed to require the permanent engraftment of the donor cell without inducing a graft rejection immune response generated by the recipient. Typically, in order to prevent a host rejection response, non-specific immunosuppressive agents such as cyclosporine, methotrexate, steroids and FK506 are used. These agents are administered on a daily basis and if administration is stopped, graft rejection usually results. However, an undesirable consequence in using nonspecific immunosuppressive agents is that they function by suppressing all aspects of the immune response (general immune suppression), thereby greatly increasing a recipient's susceptibility to infection and other diseases.

The present invention provides a method of treating a disease, disorder, or a condition that affects the CNS by introducing MSCs into the recipient without the requirement of immunosuppressive agents. The present invention relates to the discovery that administration of an allogeneic or a xenogeneic MSC, or otherwise an MSC that is genetically disparate from the recipient, into a recipient provides a benefit to the recipient. The present disclosure demonstrates that administration of such an MSC into a mammal that was subjected to MCAo (to induce stroke conditions) did not exhibit host rejection to the MSC. The disclosure presented herein demonstrates that administration of MSCs into the diseased mammal exhibit significant neurological recovery as measured by Adhesive-Removal and mNSS tests without the observation of the MSCs inducing a cytotoxic T lymphocyte response. Further, there was no significant difference in the neurological recovery between groups that received transplantation of MSCs in the presence or absence of an immunosuppressive agent such as cyclosporine. Thus, the present invention provides a method of administering MSCs to a recipient having a disease, disorder, or a condition that affects the CNS without inducing an immune response by the recipient against the MSCs. Therefore, the present invention provides a method of using MSCs to treat a disease, disorder or condition without the requirement of using immunosuppressive agents when administering MSCs to a recipient. There is, therefore, a reduced susceptibility for the recipient of the transplanted MSCs to incur infection and other diseases, including cancer relating conditions that is associated with immunosuppression therapy.

Genetic Modification

The cells of the present invention can also be used to express a foreign protein or molecule for a therapeutic purpose or for a method of tracking their integration and differentiation in a patient's tissue. Thus, the invention encompasses expression vectors and methods for the introduction of exogenous DNA into the cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The isolated nucleic acid can encode a molecule used to track the migration, integration, and survival of the cells once they are placed in the patient, or they can be used to express a protein that is mutated, deficient, or otherwise dysfunctional in the patient. Proteins for tracking can include, but are not limited to green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAF-tag, Myc, $His_6$, and the like) disclosed elsewhere herein. Alternatively, the isolated nucleic acid introduced into the cells can include, but are not limited to CFTR, hexosaminidase, and other gene-therapy strategies well known in the art or to be developed in the future.

Tracking the migration, differentiation and integration of the cells of the present invention is not limited to using detectable molecules expressed from a vector or virus. The migration, integration, and differentiation of a cell can be determined using a series of probes that would allow localization of transplanted MSCs. Such probes include those for human-specific Alu, which is an abundant transposable element present in about 1 in every 5000 base pairs, thus enabling the skilled artisan to track the progress of the transplanted cell. Tracking transplanted cell may further be accomplished by using antibodies or nucleic acid probes for cell-specific markers detailed elsewhere herein, such as, but not limited to, NeuN, MAP2, neurofilament proteins, and the like.

The invention also includes an MSC which, when an isolated nucleic acid is introduced therein, and the protein encoded by the desired nucleic acid is expressed therefrom, where it was not previously present or expressed in the cell or where it is now expressed at a level or under circumstances different than that before the transgene was introduced, a benefit is obtained. Such a benefit may include the fact that there has been provided a system wherein the expression of the desired nucleic acid can be studied in vitro in the laboratory or in a mammal in which the cell resides, a system wherein cells comprising the introduced nucleic acid can be used as research, diagnostic and therapeutic tools, and a system wherein mammal models are generated which are useful for the development of new diagnostic and therapeutic tools for selected disease states in a mammal.

A cell expressing a desired isolated nucleic acid can be used to provide the product of the isolated nucleic acid to another cell, tissue, or whole mammal where a higher level of the gene product can be useful to treat or alleviate a disease, disorder or condition associated with abnormal expression, and/or activity. Therefore, the invention includes an MSC expressing a desired isolated nucleic acid where increasing expression, protein level, and/or activity of the desired protein can be useful to treat or alleviate a disease, disorder or condition involving the CNS.

The MSC can be genetically engineered to express a growth factor, for example NGF, prior to the administration of the engineered MSC into the recipient. The engineered MSC expresses and secretes NGF at a larger amount compared with an MSC that has not been genetically modified to express such a factor. A benefit of using a genetically modified MSC in the treatment of a disease, disorder, or a condition that affects the CNS is to increase the therapeutic effects of having MSCs present in the recipient. The increased therapeutic effect is attributed to the increase secretion of NGF from the engineered MSC. With the increased secretion of NGF from the engineered MSC, a larger amount of NGF is present for neighboring cells or distal cells to benefit from the NGF. In addition, the increase amount of NGF present in the recipient allows a decrease in the time frame from which a patient can be treated.

Methods of Affecting/Modulating Cell Survival

The skilled artisan, when armed with the disclosure herein, can readily appreciate that the present invention encompasses novel methods and compositions for modulating/affecting cell survival, for example, increasing cellular survival through increased Akt and Erk1 at both the protein level and the RNA level. The present invention is based on the discovery that when MSCs were co-cultured with astrocytes that have been subjected to ischemic conditions, it has been observed that the presence of MSCs with the post-ischemic astrocyte in culture reduced the amount of cell death of the astrocytes. The present disclosure demonstrates that when astrocytes were incubated in ischemic conditions such as incubation of the astrocytes in an anaerobic chamber, and then co-cultured with MSCs, there was a significant reduction in the cell death and apoptotic phenotypes exhibited by the astrocytes compared with post-ischemic astrocytes cultured in the absence of MSCs.

The data herein demonstrates that co-culturing astrocytes with MSCs upregulated the phosphorylation of Erk1 and Akt in astrocytes. While not wishing to be bound to any particular theory, it is believed that MSCs contribute to the survival of neighboring astrocytes by activating cellular proliferation and survival signaling pathways post-translationally. It was demonstrated that astrocytes that were treated with MEK inhibitor (U0126), which inhibits Erk1 phoshporylation, or PI3K inhibitor (LY29004), which inhibits Akt phosphorylation, underwent significant apoptosis and cell death similar to the post-ischemic control group. As such, the inhibition of molecular pathways leading to the activation of Erk1 and/or Akt inhibits the ability of a cell to survive conditions that cause cell death and/or apoptosis that otherwise activation of such pathways would overcome the cell death and/or apoptosis conditions. Based on the present disclosure, the duration for which Erk1 and/or Akt are activated increases the ability of a cell that has been subjected to cell death/apoptotic conditions to survival from such conditions. In addition, the intensity for which Erk1 and/or Akt is activated in a cell increases the survival potential of a cell from cell death/apoptotic conditions. As such, the present invention comprises a method of using MSCs to activate survival signals, such as activation of Erk1 and/or Akt in a cell in order to confer protection to the cell from cell death/apoptotic conditions.

In addition to the ability of MSCs to activate cellular pathways in neighboring cells, the present disclosure also demonstrates that MSCs can induce neighboring post-ischemic astrocytes to increase the transcription of various growth factors including, but are not limited to bFGF, BDNF, and VEGF. Based upon the present disclosure, one skilled in the art would appreciate that MSCs can enhance the recovery of post-ischemia astrocytes by stimulating the activation of MEK/Akt and PI3K/Erk pathways in astrocytes, and increasing growth factor production by astrocytes.

Axonal and Myelination Remodeling

Axonal loss and demyelination are frequently observed to be associated with a disease, disorder, or a condition that affects the CNS. Axonal loss and demyelination is believed to contribute to neurological functional impairment in CNS conditions, for example, in ischemic cerebrovascular diseases and inflammatory demyelinating diseases, such as MS.

The disclosure presented herein demonstrates that administration of MSCs to a diseased mammal having a condition including, but not limited to an ischemic condition, an axonal degeneration, or demyelination, improves neurological functional recovery in the diseased mammal. The present disclosure also demonstrates that the administered cells play a role in the formation and/or maintenance of axonal fibers in an injured or otherwise diseased brain. In some instances, the administered cells prevent axonal fiber loss in the brain of the diseased mammal. Mammals that were subjected to ischemic conditions or conditions of inflammatory demyelination and subsequently treated with the administration of MSCs demonstrated significant reduced areas of demyelination and reduced areas of axon loss compared with an otherwise identical mammal not treated with MSCs. While not wishing to be bound to any particular theory, the improved neurological functions exhibited by the diseased mammal following treatment with MSCs is attributed to the reduced demyelination and axon loss.

In some instances, the therapeutic effects of administering MSCs to the mammal suffering from a neurodegenerative disease, such as MS, is not the result of cell replacement therapy. That is, the disclosure presented herein demonstrates that a therapeutic effect from the administered MSCs can be attributed to the fact that the MSCs stimulate endogenous brain parenchymal cells to express NGF. The expression of NGF by endogenous brain parenchymal cells stimulates axonal repair in both acute and chronic diseases. Thus, in some instances, a therapeutic outcome from transplantation of MSCs to a mammal in need thereof does not require differentiation of MSCs into cells of the CNS, such as neurons, to replace the damaged or injured cells.

Based on the present disclosure, one skilled in the art would appreciate that the loss of axonal fibers and demyelination of the axons contribute to neurological impairment. Axons play a major role in the neurological functions of a mammal. Axons are insulated by a myelin sheath, which greatly increases the rate at which an axon can transport a signal. Any loss in axonal fibers or conditions of demyelination retards neurons from properly functioning, for example, significant impairment in sensory, motor and other types of functioning when nerve signals reach their targets either too slowly, asynchronously (when some axons in a nerve conduct faster than others), intermittently (when conduction is impaired only at high frequencies), or not at all. As such, the present invention provides compositions and methods for treating a neurological impairment by preventing degradation of axonal fibers and preventing demyelination. In addition, the present invention encompasses compositions and methods for using MSCs to remodel axonal fibers and myelination.

The above discussion provides a factual basis for the use of bone marrow stromal cell transplantation for the treatment of neural injury and neurodegeneration. The methods used with and the utility of the present invention can be shown by the following non-limiting examples and accompanying figures.

Standard molecular biology techniques known in the art and not specifically described were generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989) and in Perbal, A Practical Guide to Molecular Cloning, John Wiley & Sons, New York (1988), and in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,66,828; 4,683, 202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In-situ (in-cell) PCR in combination with Flow Cytometry can be used for detection of cells containing specific DNA and mRNA sequences (Testoni et al, 1996, Blood 87:3822).

Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

EXAMPLES

Example 1

Treatment of Stroke (Rat) with Intracerebral Transplantation of MSC

Description of Intracerebral Transplantation of Bone Marrow Derived MSCs after Cerebral Ischemic in the Rat Adult male Wistar rats were used in this study (n=28). Rats were subjected to middle cerebral artery occlusion (MCAo) for two hours using the intraluminal occlusion model. Following MCAo, the control group (rats subjected to MCAo without receiving transplantation of MSCs (n=8)), was compared with the experimental groups, which included injection into the ischemic boundary zone (IBZ) at 24 hours after MCAo: phosphate buffered saline (n=4); non NGF cultured bone marrow MSCs (n=8); and NGF cultured MSCs (n=8). Approximately $4 \times 10^4$ cells in 10 μl total fluid volume were injected into the rat following MCAo. The rats were sacrificed 14 days after MCAo.

Behavioral Outcome Measurements

Figure 1B:
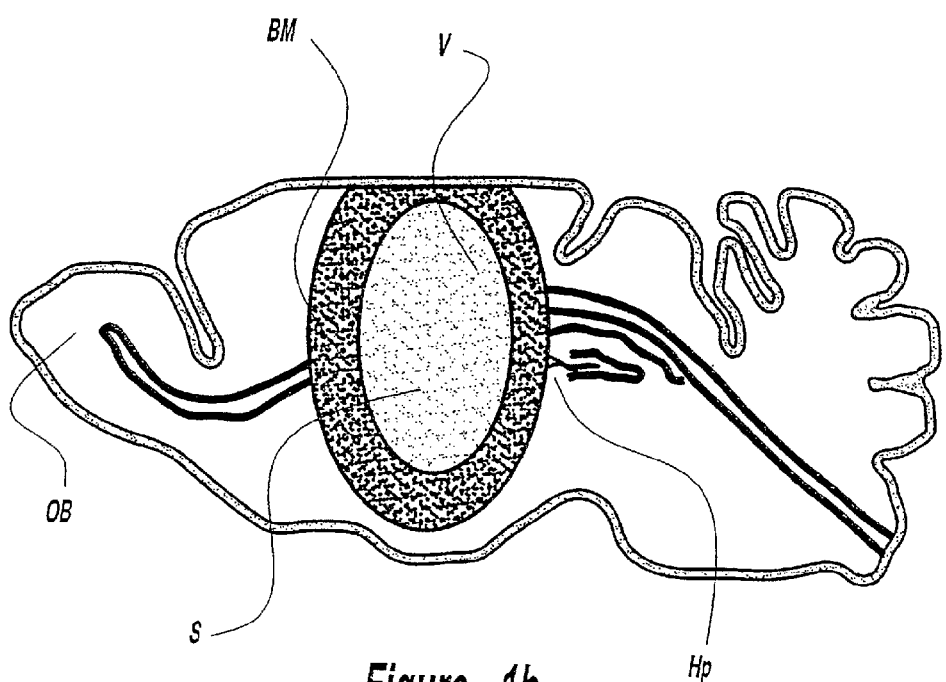

Behavioral data from the battery of functional tests (rotarod, adhesive-removal and Neurological Severity Score tests (NSS)) demonstrated that motor and somatosensory functions were impaired by the ischemic insult by way of subjecting the rats to MCAo. It was observed that no significant differences of the rotarod, adhesive-removal and NSS tests were detected among the groups prior to surgery and before transplantation. Significant recovery of somatosensory behavior ($p<0.05$) and NSS ($p<0.05$) were detected in mammals transplanted with MSCs following MCAo compared with mammals not receiving transplantation of MSCs following MCAo mammal (FIGS. 1A, 1C). Mammals that received transplantation of MSCs that were cultured with NGF displayed significant recovery in motor ($p<0.05$), somatosensory ($p<0.05$) and NSS ($p<0.05$) behavioral tests at two weeks post-transplantation with NGF, compared with transplantation of MSCs alone. FIGS. 1A, 1B, 1C show data from the adhesive-removal test, the rotarod-motor test and the NSS, respectively. These data clearly demonstrate that treatment of stroke with intracranial transplantation of MSCs provides significant therapeutic benefit and that MSCs when cultured in NGF provides superior therapeutic benefit compared with MSCs cultured without NGF, as indicated in the motor test data (FIG. 1B).

Example 2

Treatment of Stroke (Mouse) with Intracerebral Transplantation of MSC

Intrastriatal Transplantation of MSCs into Mice after Stroke: Embolic MCAo and Transplantation Experimental adult mice (C57BL/6, weighing about 27-35 g) were subjected to MCAo and following MCAo, the mice received transplantation of MSCs (n=5). Control mice were subjected to MCAo alone (n=8). Experimental groups received either injection of PBS into the ischemic striatum (n=5); or transplantation of MSCs into the normal striatum (n=5). MCAo was induced using an embolic model developed in our laboratory (Zhang et al., 1997). Briefly, using a facemask, mice were anesthetized with 3.5% halothane and anesthesia was maintained with 1.0% halothane in 70% $N_2O$ and 30% $O_2$. A single intact fibrin-rich in 24 hour old homologous clot (8 mm×0.000625 $mm^2$, 0.18:1) was placed at the origin of the MCAo via a modified PE-50 catheter. Surgical and physiological monitoring procedures were identical to those previously published (Zhang et al., 1997). Four days after MCAo (n=18), the mice were mounted on a stereotaxic frame (Stoelting Co. Wood Dale, Ill.). Using aseptic technique, a burr hole (1 mm) was made on the right side of the skull to expose the dura overlying the right cortex. Semisuspended MSCs ($1 \times 10^5$ in 3:1 PBS) were slowly injected over a 10-minute period into the right striatum (AP=0 mm, ML=2.0 mm, and DV=3.5 mm from the bregma). Without wishing to be bound to any particular theory, this position approximates the ischemic boundary zone in the striatum.

The needle was retained in the striatum for an additional 5 minutes interval to avoid donor reflux. Mice were sacrificed at 28 days after stroke.

Behavioral Testing

Each mouse was subjected to a series of behavioral tests (rotarod-motor test, Neurological Severity Score) to evaluate various aspects of neurological function by an investigator who was blinded to the experimental groups. Measurements were performed prior to stroke and at 28 days after stroke.

Results

BrdU reactive MSCs survived and migrated a distance of approximately 2.2 mm from the grafting areas toward the ischemic areas. BrdU reactive cells expressed neuronal (~1% NeuN) and astrocytic proteins (~8% glial fibrillary acidic protein, GFAP). Functional recovery from a rotarod test ($p<0.05$) and modified Neurological Severity Score tests (NSS, including motor, sensory and reflex, $p<0.05$) were significantly improved in the mice receiving MSCs following MCAo treatment compared with mice not receiving MSCs following MCAo treatment (FIG. 2). FIG. 2 shows that mice treated with transplanted MSCs exhibited a significant improvement in the duration on the rotarod (FIG. 2) and an improved neurological function (FIG. 2) compared to vehicle treated mammals. The findings suggest that the intrastriatal transplanted MSCs survive in the ischemic brain and improve functional recovery of adult mice.

Example 3

Treatment of Stroke (Mouse) with Intravascular Administration of MSC

Description of Experiments

Experiments were performed on adult male Wistar rats (n=30) weighing about 270 to 290 g. In all surgical procedures, anesthesia was induced in rats with 3.5% halothane, and maintained with 1.0% halothane in 70% $N_2O$ and 30% $O_2$ using a face mask. The rectal temperature was controlled at 37° C. with a feedback regulated water heating system. Transient MCAo was induced using a method of intraluminal vascular occlusion, as described above. Two hours after MCAo, reperfusion was performed by withdrawal of the suture until the tip cleared the internal carotid artery.

(Intracarotid Administration of MSCs)

Intra-carotid transplantation of MSCs was carried out at 24 hours after MCAo (n=23). A modified PE-50 catheter was advanced from the same site of this external carotid artery into the lumen of the internal carotid artery until it rested 2 mm proximal to the origin of the MCA (FIG. 1). Approximately $2\times10^6$ MSCs in 200 µl PBS (n=6) or control fluid (200 µl PBS, n=8) were injected over a 10-minute period into each experimental rat. Immunosuppressants were not used in any mammal. All rats were sacrificed at 14 days after MCAo.

(Intravenous Administration of MSCs)

For intravenous administration of MSCs, a femoral vein was cannulated and either $1.5\times10^6$ MSCs or $3\times10^6$ MSCs were injected.

Behavioral Tests and Immunohistochemistry

Each rat was subjected to a series of behavioral tests (NSS and adhesive removal test) to evaluate neurological function before MCAo, and at 1, 4, 7 and 14 days after MCAo. Single and double immunohistochemistry were employed to identify cell specific proteins of BrdU reactive MSCs.

Results

For intra-arterial administration, BrdU reactive cells (~21% of $2\times10^6$ transplanted MSCs) distributed throughout the territory of the MCAo by 14 days after ischemia. Some BrdU reactive cells expressed proteins characteristic of astrocytes (glial fibrillary acidic protein, GFAP) and neurons (microtubule associated protein-2, MAP-2). Rats with MSC intra-arterial transplantation exhibited significant improvement on the adhesive-removal test ($p<0.05$) (FIG. 3) and the modified Neurological Severity Scores ($p<0.05$) (FIG. 3) at 14 days, compared with controls. The data for intravenous administration of MSCs were very similar, in that significant functional improvement was present with rats treated with MSCs compared to placebo treated rats. FIG. 4 shows functional data from rats receiving administration of MSCs intravenously compared to control-ischemia rats not receiving MSCs. A significant improvement is noted in the speed in which the rats removed the sticky tabs from their paws at seven and 14 days after stroke, compared to control mammals (FIG. 4). The overall neurological function of rats receiving MSCs administered intraarterially was significantly improved compared to control-ischemia rats at 14 days after stroke. The findings suggest that MSCs injected intra-arterially are localized and directed to the territory of MCAo and these cells foster functional improvement after cerebral ischemia. In addition, intravenous administration of MSCs also provides a significant improvement in functional outcome. Thus, the data presented demonstrated that vascular administration is a feasible and effective route of administration of therapeutically beneficial MSCs.

Example 4

Treatment of Traumatic Brain Injury (Rat) with Intracerebral Transplantation of MSC Description Experiments were performed on 66 male Wistar rats weighing about 250-350 grams. A controlled cortical impact device was used to induce injury to the rats (Dixon et al. 1991 J. Neuroscience Methods 39:253-262). Injury was induced by impacting the left cortex with a pneumatic piston containing a 6 mm diameter moving at a rate of 4 min/second and producing 2.5 mm compression. BrdU labeled MSCs were harvested from donor mammals and implanted into the ipsilateral hemisphere, as in the stroke experiments. MSCs were transplanted into brain 24 hours after injury. Rats receiving transplantation of MSCs were sacrificed at 4 days (n=4), 1 week (n=15), 2 weeks (n=4) and 4 weeks (n=4) after transplantation. Control mammals were divided into 3 groups: 1) rats subjected to injury without transplantation and sacrificed at 8 days (n=4) and 29 days (n=4) after injury; 2) mammals injected with PBS one day after injury and sacrificed at 4 days (n=4), 7 days (n=4), 14 days (n=4) and 28 days after PBS injection; 3) sham control rats with craniotomy but no injury or transplantation were sacrificed 8 days (n=4) and 29 days (n=4) after craniotomy.

Outcome Measures (Behavior, Histology):

An accelerating rotarod test was employed to measure motor function. Measurements were performed at 2, 5, 15, and 29 days after injury. After sacrifice, brain sections were stained with hematoxylin and eosin and double-labeled immunohistochemistry was performed to identify MSC cell type.

Results

Histological examination revealed that after transplantation MSCs survived, proliferated and migrated towards the injury site. BrdU labeled MSCs expressed markers for astrocytes and neurons. Rats transplanted with MSCs exhibited a significant improvement in motor function compared with control mammals which did not received transplantation of MSCs. The data indicate that intracerebral transplantation of MSCs significantly improves neurological function after traumatic brain injury. In a complementary set of experiments, treated rats were also subjected to traumatic brain injury and received transplantation of MSCs; however, in this experiment MSCs were delivered to the brain by means of intraarterial (intracarotid artery) administration. The data were observed to be similar to intracranial transplantation. MSCs migrated readily into the injured region of brain and these cells expressed protein markers of brain cells (astrocytes, neurons). Thus, the present disclosure indicate that traumatic brain injury can be treated with MSC administered intracerebrally or via a vascular route.

Example 5

Treatment of Parkinson's (Mouse) with Intracranial Transplantation of MSCs

Description of MPTP Method and Results

Adult male C57BL/6 mice, 8 week-old, weighing about 20-35 g, were employed in this study. In order to obtain severe and long lasting lesions, mice were treated with intraperitoneal injections of 1-methyl-4-phenyl-1,2,3,6-tetrahydropyridine (MPTP) hydrochloride (30 mg/kg, Sigma) in saline once a day for seven consecutive days (210 mg/kg total dose). Mice were transplanted with BrdU labeled MSCs ($3 \times 10^5/3$ µl) directly into the right striatum, stereotaxically.

Behavioral Tests

Mice subjected to each MPTP injection, presented and retained behavioral abnormalities (akinesia, postural instability, tremor and rigidity) for several hours, as reported in literature (Heikkila et al., 1989).

Figure 5A:
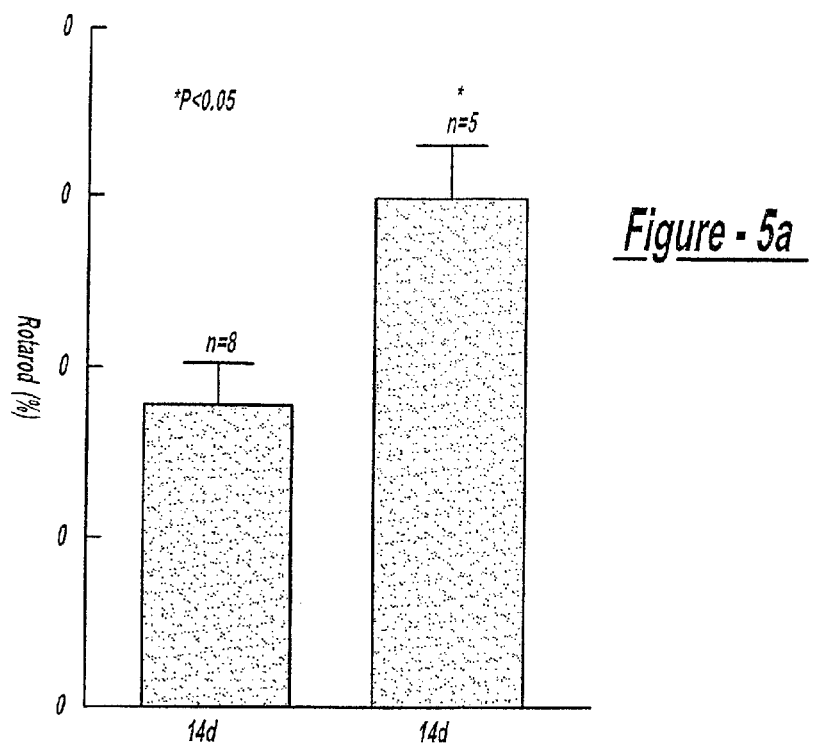
FIG. 5A through FIG. 5B, depicts grafts demonstrating that mice treated with transplanted MSCs exhibited a significant improvement in the duration on the rotarod and an improved neurological function compared to vehicle treated mammals.
Figure 5B:
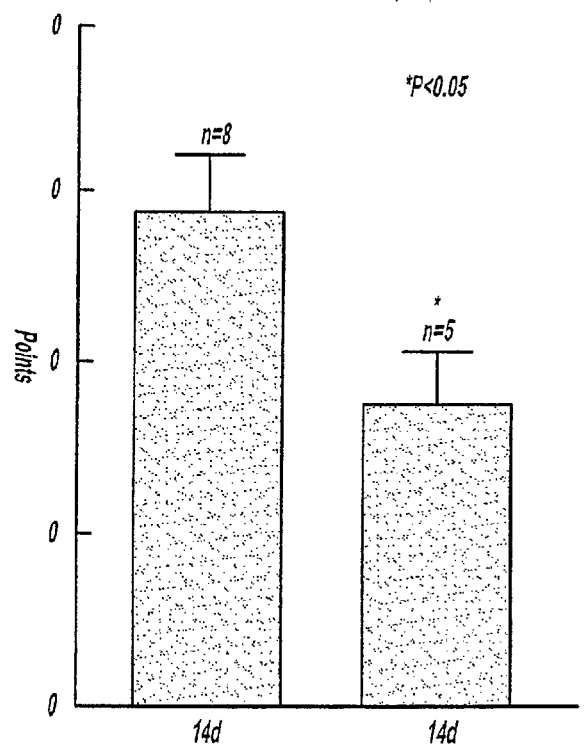
Figure 6A:
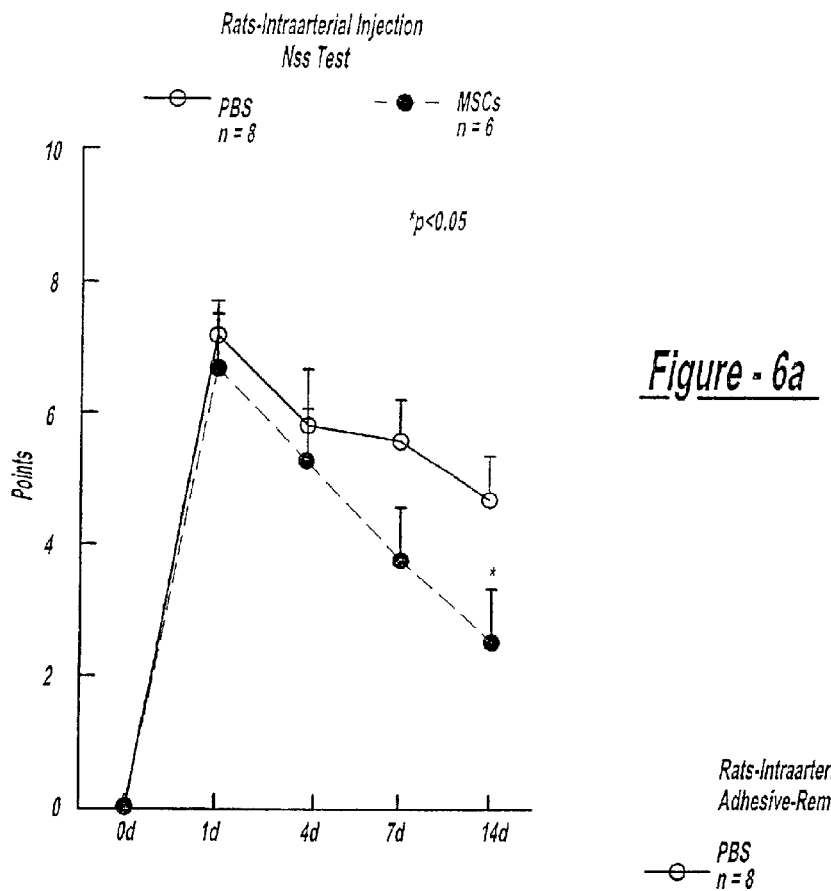
FIG. 6A through FIG. 6B, depicts that rats that received MSC intraarterial transplantation exhibited significant improvement on the adhesive-removal test and the modified Neurological Severity Scores (mNSS) at 14 days following transplantation compared with control mammals.
Figure 6B:
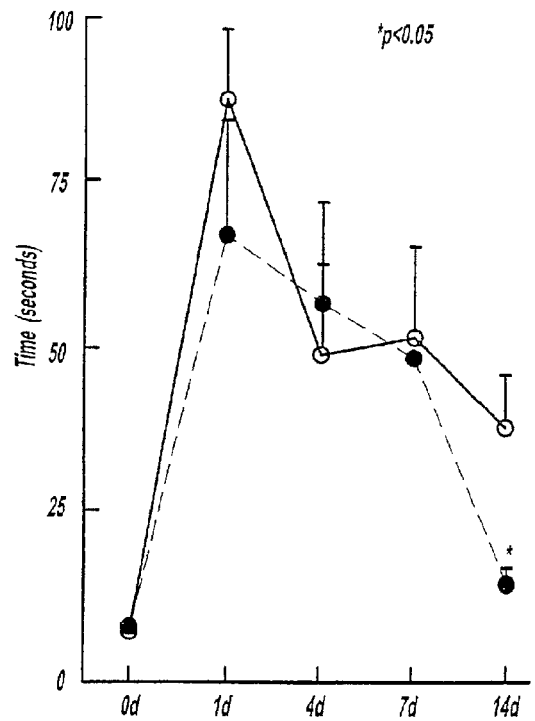

Drug-free evaluation of Parkinson's disease (PD) using rotarod test was described by Rozas et al. (1997, 1998). MPTP-PD mice with or without MSC transplantation were tested on a rotarod at an increasing speed (16 rev/minute and 20 rev/minute) after the last MPTP injections (five trials per day to obtain stable values) without any additional enhanced drug injection. A trial was terminated when the mice fell from the rotarod. Significant improvement in motor function (p<0.05) was observed at 35 days after MPTP injection in Parkinson's disease mice treated with MSC transplantation compared with control MPTP-injected mice alone. FIG. 5 shows rotarod data from mice subjected to MPTP neurotoxicity. Two experiments were performed; the mice were placed on the rotarod rotating at 16 rpm or at 20 rpm. The data demonstrated that mice treated with MSCs showed a significant increase in duration on the rotarod at both angular velocities compared to MPTP mice given PBS intracerebrally. Mice treated with MSCs cultured with NGF appeared to have incremental benefit compared to MSC treatment, although the differences were not observably significant.

Morphological Changes

Viable BrdU immunoreactive cells were identified in the injected area and migrated to variable distances into the host striatum (FIG. 1B) at 35 days. Double staining shows that scattered BrdU reactive cells (FIG. 1C) express tyrosine hydroxyls (a dopamine marker) immunoreactivity (FIG. 1D) within the grafts.

Conclusions

These data demonstrate that intracerebral transplantation of MSCs reduces Parkinson's disease symptoms in mice.

Example 6

Treatment of Spinal Cork Injury (Rat) with Intralesional Transplantation of MSCs Description of Spinal Cord Injury (SPI)

Impact injury was induced using the weight-drop 10 g from a height of 25 mm, 'NYU impact' model) to produce a spinal cord injury of moderate severity. Adult male Wistar rats (300±5 g) were anesthetized with pentobarbital (50 mg/kg, intraperitoneally), and a laminectomy was performed at the T9 level.

Transplantation and Behavioral Testing

Figure 7A:
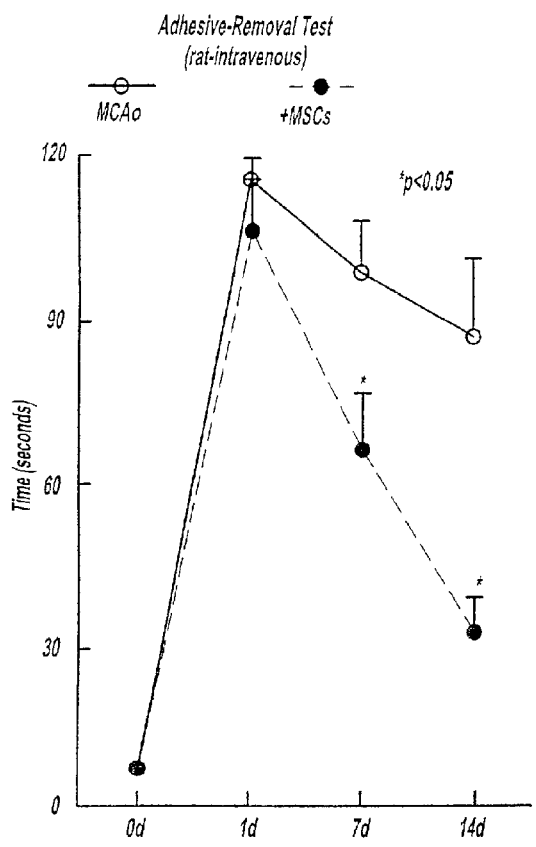
FIG. 7, comprising FIG. 7A through FIG. 7B depicts functional data from rats receiving administration of MSCs intravenously compared with control-ischemia rats not receiving MSCs.
Figure 7B:
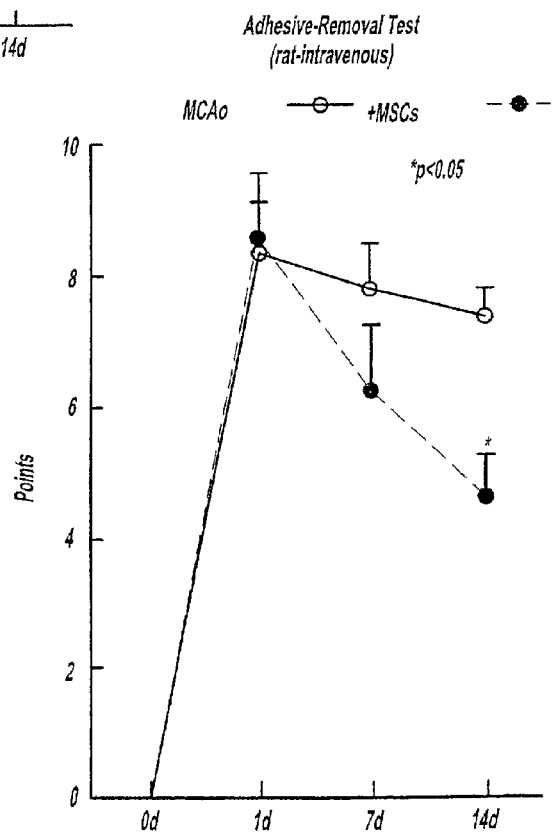

MSCs $2.5 \times 10^5/4:1$ were injected into the epicenter of injury at 7 days after SPI. The Basso-Beatie-Bresnahan (BBB) Locomotor Rating scores were obtained before and after transplantation (Basso et al., 1995). FIG. 7 shows data from the BBB test from mammals subjected to spinal cord injury, and receiving MSC transplantation or simply given the same volume of vehicle. All rats had a score of 21 (normal score) before spinal cord injury and a score of zero at 6 hours after contusion. In the rats subjected to contusion with PBS injection, scores improved from 6.7 (1 week) to 11.5 (5 weeks). The control group had an early improvement in neurologic function, which plateaued by the third week. The rats subjected to contusion with MSC transplantation had a significantly improved score of 7.0 (1 week) and 15.3 (5 weeks). The MSC treated group exhibited a steady recovery that had not plateaued by the fifth weeks, which was the end point of the experiment. The MSC treated rats had significant improvement on BBB scores with the p-value, 0.01 for overall and each individual time point for treatment effect. In functional terms, the contused rats in the MSC treated group could walk with consistent weight supported plantar steps with forelimb and hindlimb coordination. In contrast, the contused rats in the PBS control group exhibited obvious motor function deficits.

Histological Analysis

Figure 2A:
FIG. 2, comprising FIG. 2A through FIG. 2L is an image depicting bone marrow cells in an H&E prepared section in the immunoreactivity of representative proteins in the (ischemic boundary zone) IBZ of a series of adjacent sections from rats sacrificed four days after bone marrow transplantation (FIG. 2A through FIG. 2H).
FIG. 2I depicts the neuronal specific nuclear protein, NeuN.
FIG. 2J demonstrates that the bone marrow transplantation of the cells adjacent to the ependymal cells exhibited reactivity for the neuronal marker, MAP-2.
FIG. 2K-FIG. 2L depict that the cells of the (subventricular zone) SVZ express Neuro D and glial fibrillary acidic protein (GFAP) protein markers.
Figure 2B:
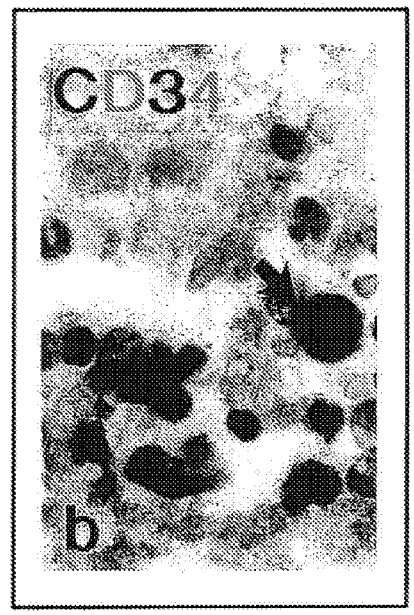
Figure 2C:
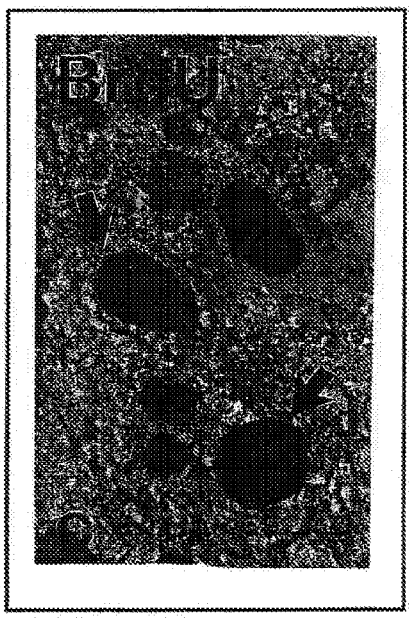
Figure 2D:
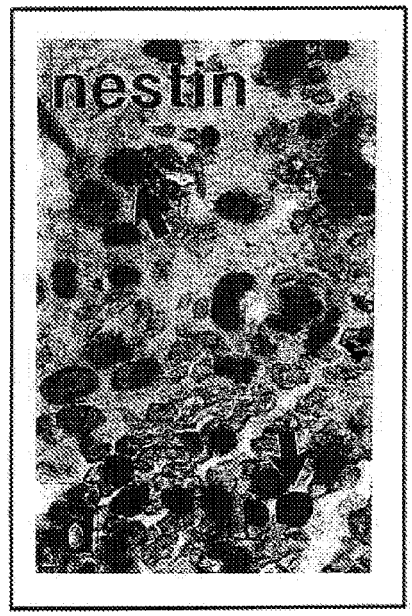
Figure 2E:
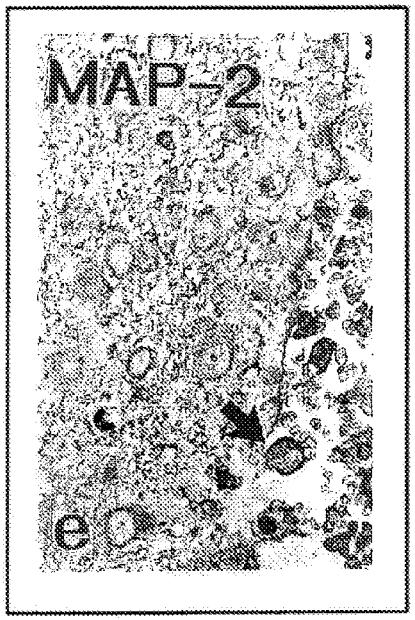
Figure 2F:
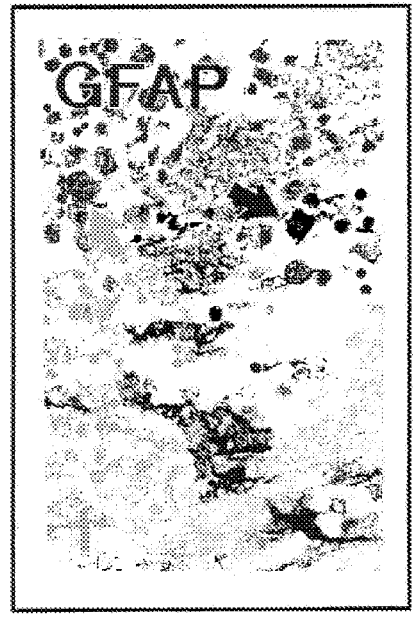
Figure 2G:
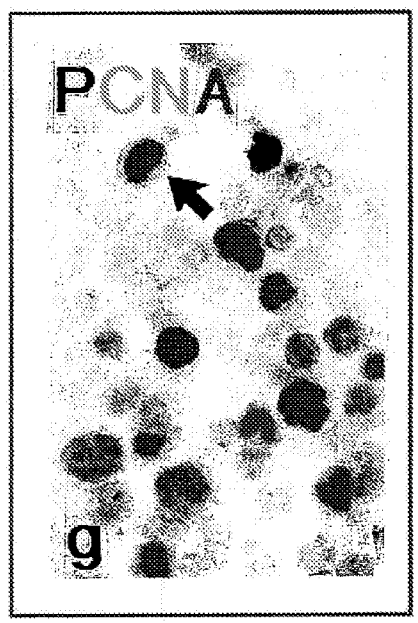
Figure 2H:
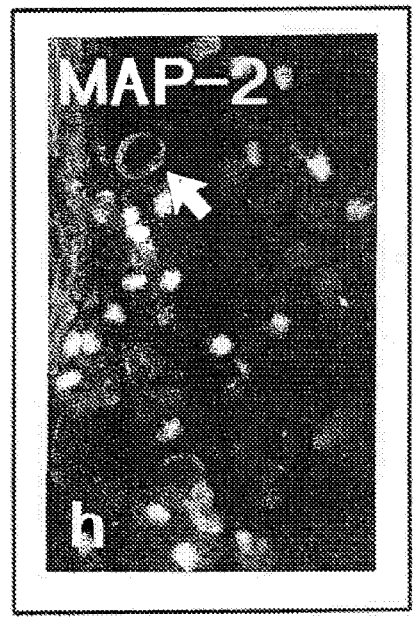
Figure 2I:
Figure 2J:
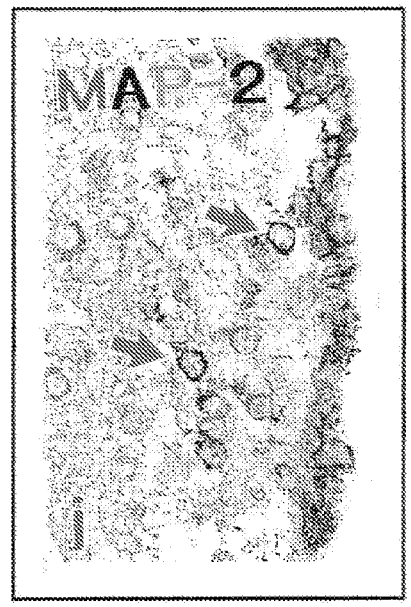
Figure 2K:
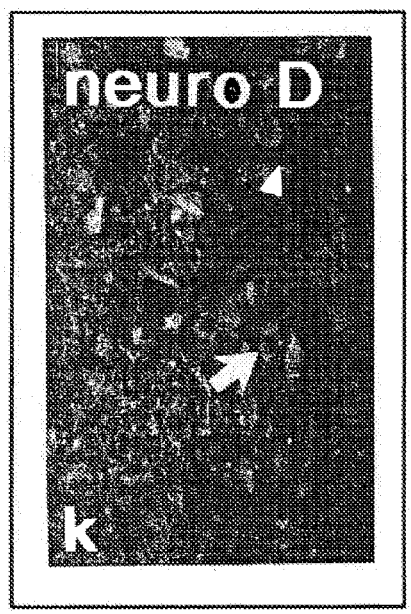
Figure 2L:
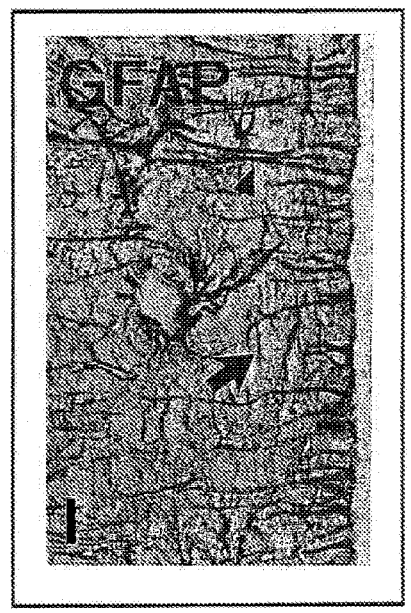
Figure 3A:
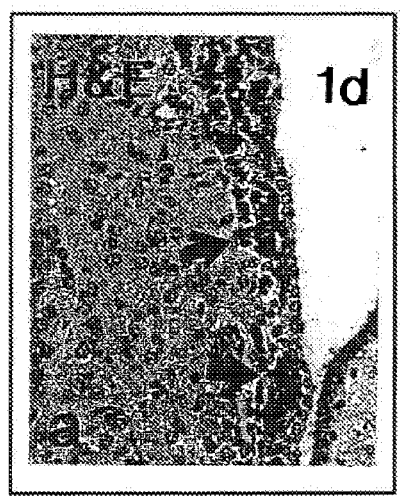
FIG. 3A through FIG. 3H, is a series of images depicting H&E prepared sections of cerebral tissue after MCAo and having bone marrow cells transplanted into the mammal after MCAo.
Figure 3B:
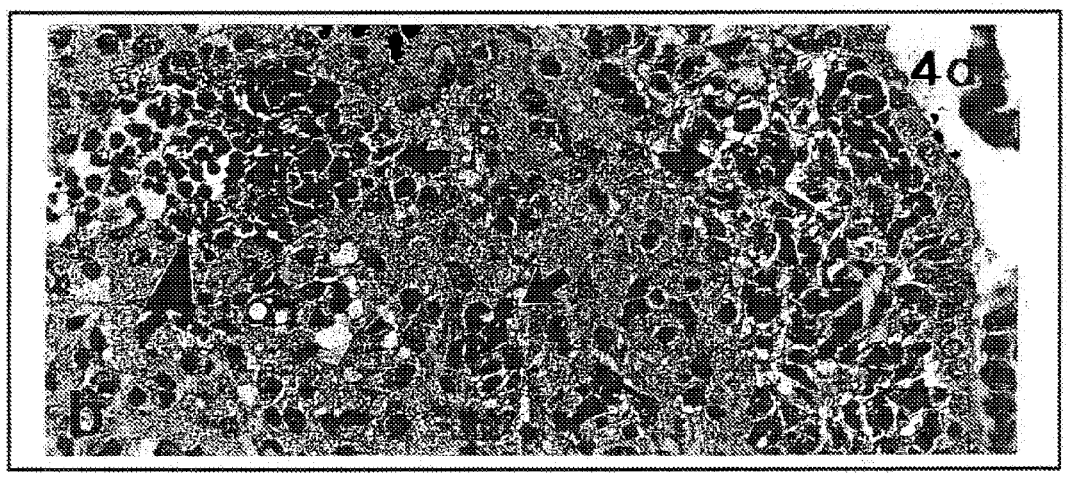
Figure 3C:
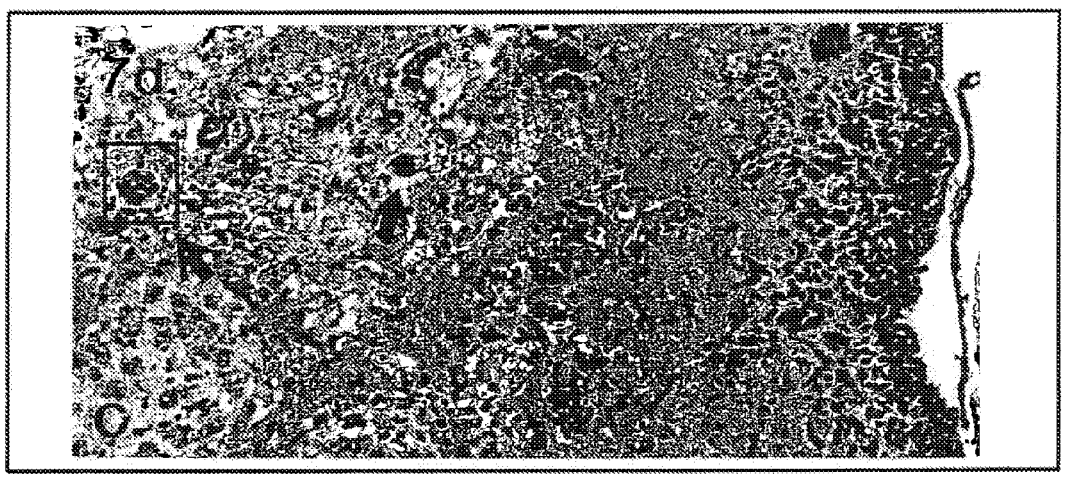
Figure 3D:
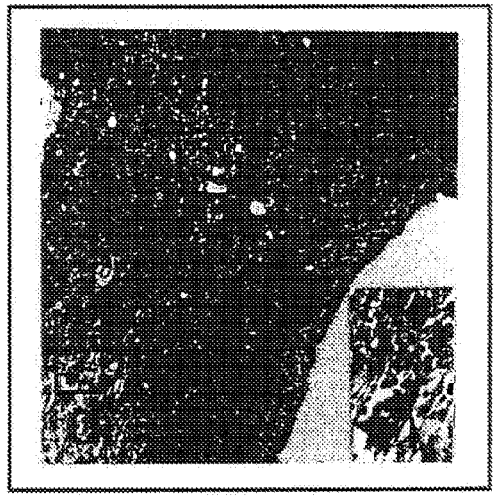
Figure 3E:
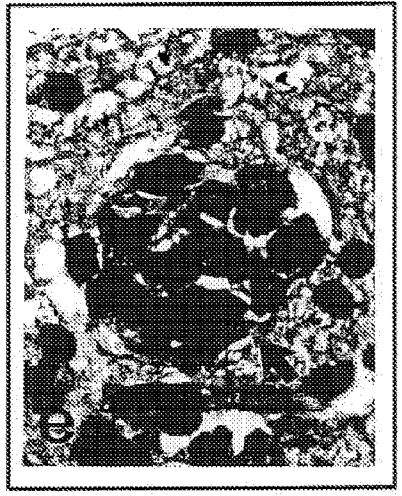
Figure 3F:
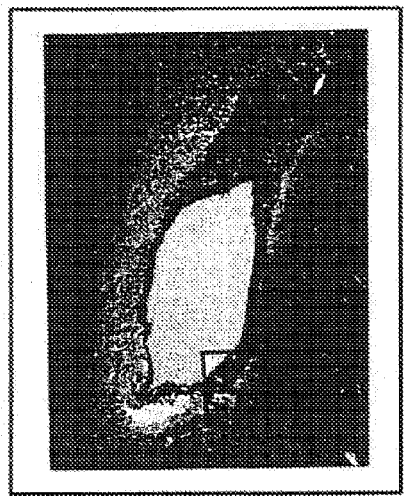
Figure 3G:
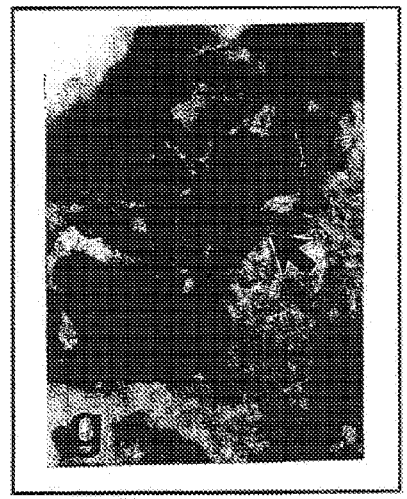
Figure 3H:
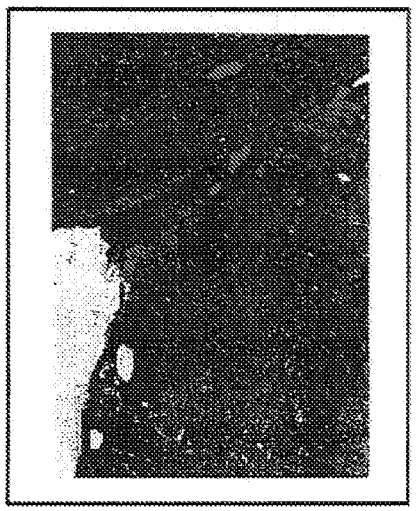
Figure 3I:
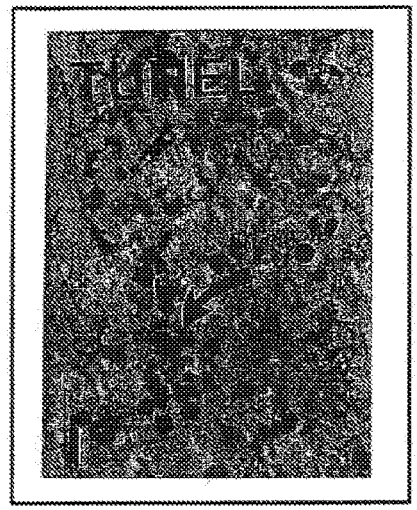
FIG. 3I through FIG. 3L, is an image depicting the TUNEL staining exhibiting apoptotic-like cells within the bone marrow grafting at four days following transplantation.
Figure 3J:
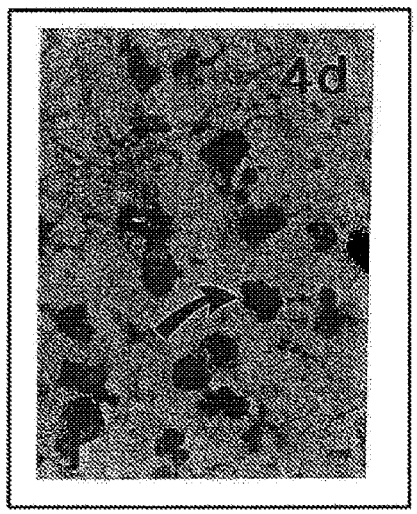
Figure 3K:
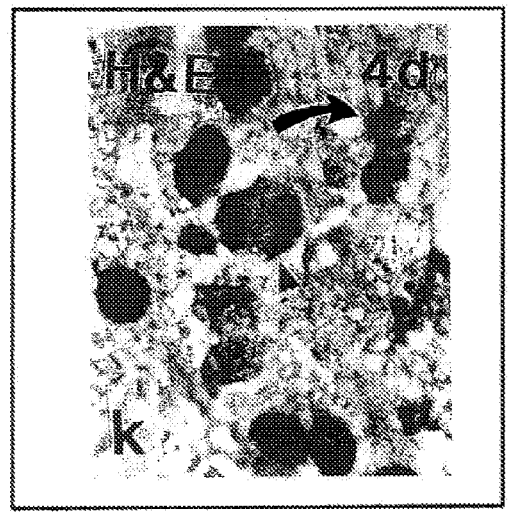
Figure 3L:
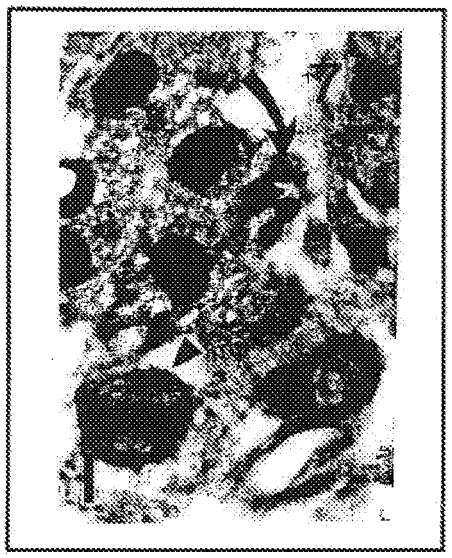

Cells derived from MSCs, identified by BrdU immunoreactivity, survived and were distributed throughout the damaged tissue (T9, FIG. 1A) from 1 week to 4 weeks after MSC transplantation. BrdU reactive cells migrated 5 mm both caudal and rostral from the epicenter of transplanted cells (FIG. 1B). FIG. 2A shows that the antibody against Rip did not react with damaged oligodendrocytes in contused rats with non treated PBS injection. In contrast, after spinal cord injury and receiving MSC transplantation (FIG. 2B), intense Rip immunoreactivity clearly demarcated myelinated small and large diameter fibers. Double immunostaining (FIGS. 2C-D) demonstrates that scattered BrdU reactive cells express the neuronal marker, NeuN.

Conclusions:

Treatment of moderate to severe spinal cord injury in a mammal by administering MSCs into the site of injury provides significant improvement of motor function. The MSCs express protein markers of neurons and oligodendrocytes, indicating that these cells when placed within the spinal cord acquire characteristics of parenchymal cells.

Example 6

Figure 8:
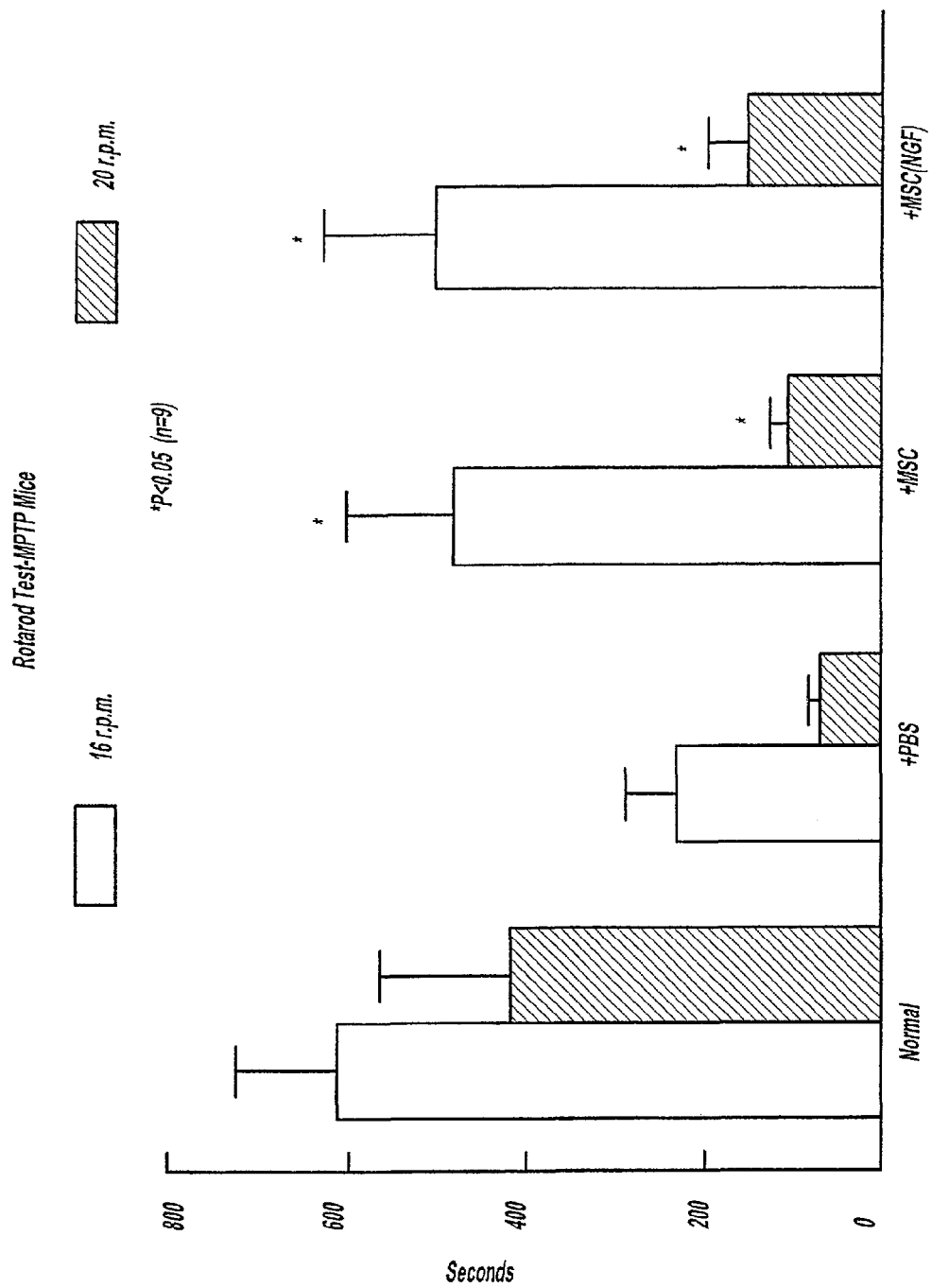
FIG. 8 depicts rotarod data from mice subjected to 1-methyl-4-phenyl-1,2,3,6-tetrahydropyridine (MPTP) neurotoxicity.
Figure 9A:
FIG. 9, comprising FIG. 9A through FIG. 9D depicts the morphological changes, i.e. most shrunk pigmented neurons disappeared and only few of them were observed in the substantia nigra at 45 days after MSC transplantation in MPTP induced Parkinson's diseased (MPTP-PD) mice; viable 5-bromo-2-deoxyuridine (BrdU) immunoreactive cells identified in the injected area and migrated to variable distances into the host striatum at 45 days after transplantation of the MSCs; double staining shows that scattered BrdU reactive cells express tyrosine hydroxylase (TH) immunoreactivity within the grafts.
Figure 9B:
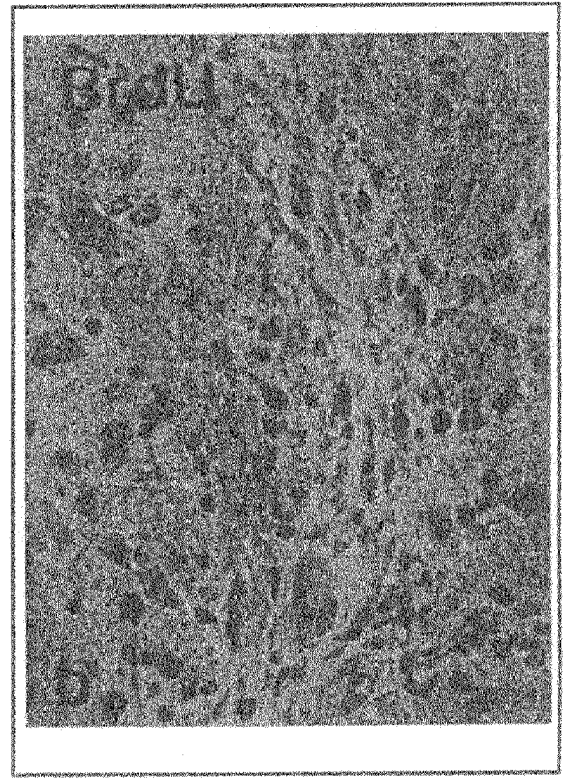
Figure 9C:
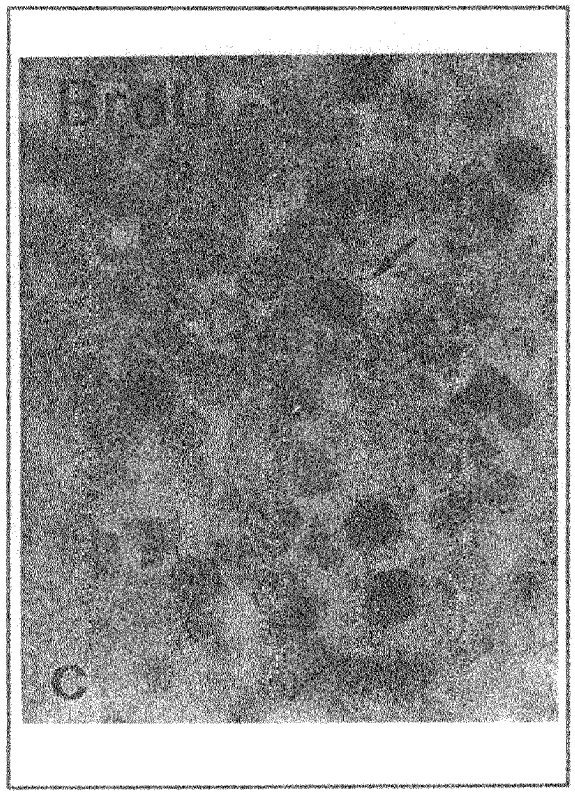
Figure 9D:
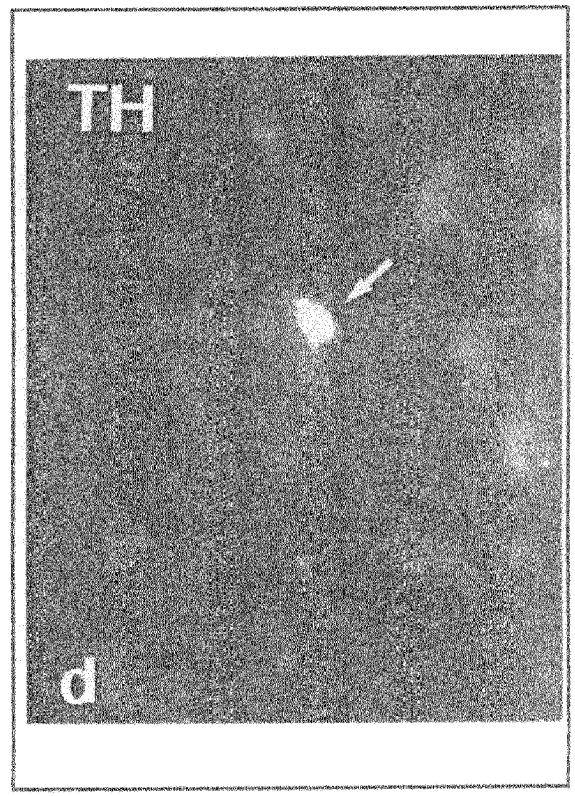
Figure 10:
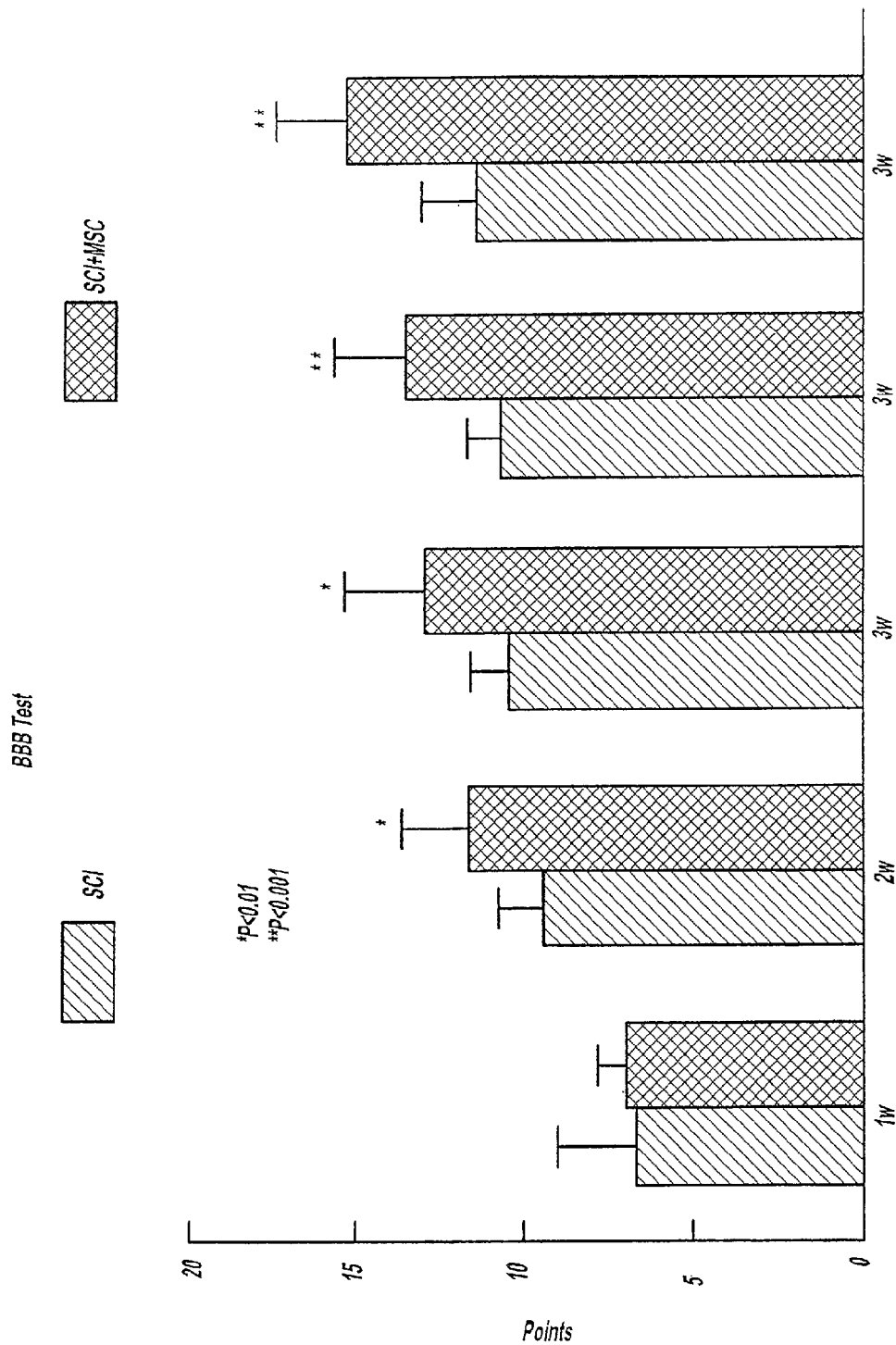
FIG. 10 depicts data from the Basso-Beaftie-Bresnahan (BBB) test from mammals subjected to spinal cord injury.
Figure 11:
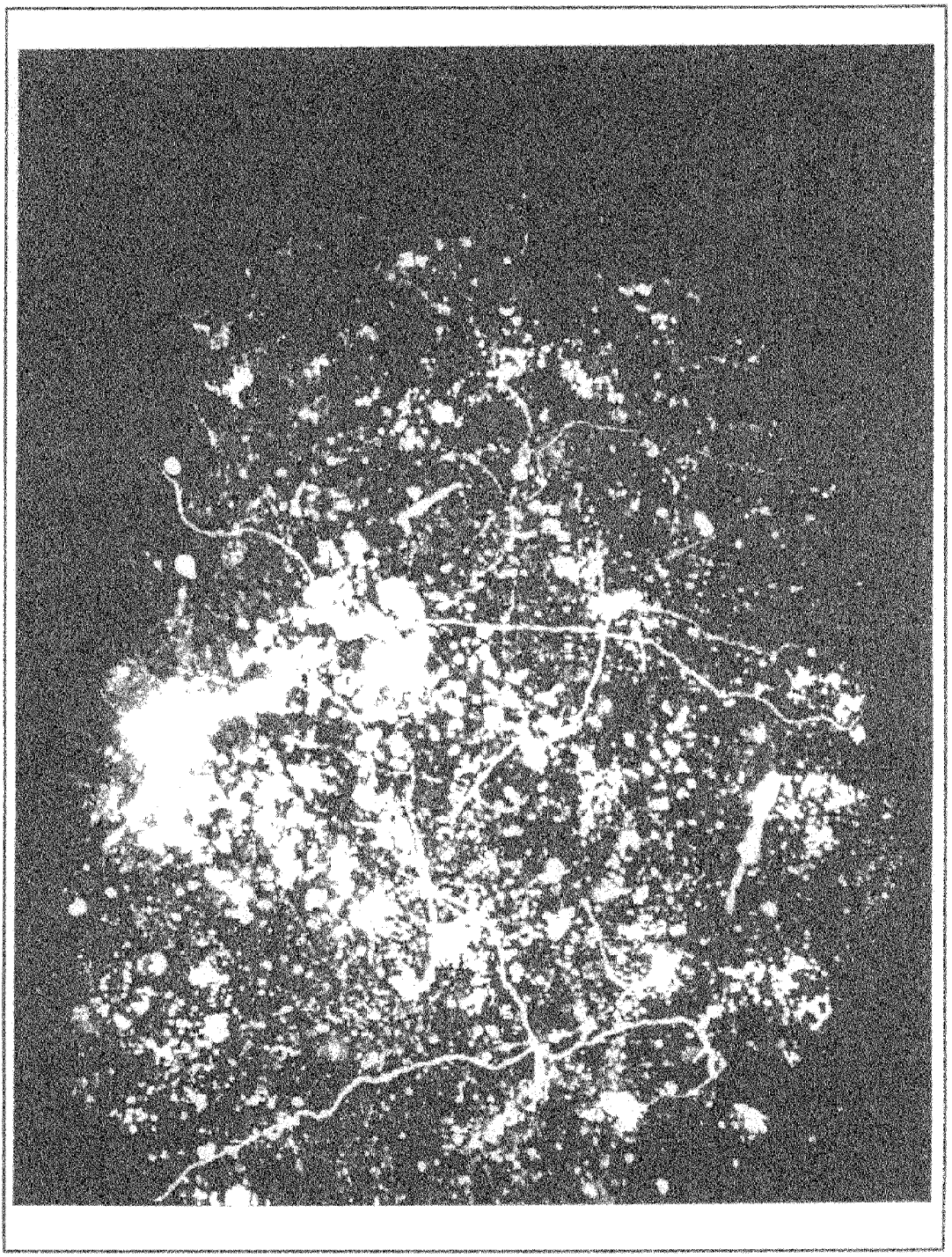
FIG. 11 is an image depicting the composite MSC neurosphere nine days after cell-neurosphere integration.

Neurosphere (NMCsphere)—a New Composite for the Treatment of CNS Injury and Disease Description of Neurosphere Experiment Aggregates, composed of neural stem cells from fetal neurosphere, mesenchymal stem cells from adult bone marrow and cerebro-spinal fluid from adult Wistar rats (called NMCspheres) were used in the following experiments. Fetal brain cells were pre-labeled with 1,1'-dioctadecy-6,6'-di(4-sulfophenyl)-3,3,3',3'-tetramethylindocarbocyanine (Dil) and bone marrow mesenchymal cells from adult rats were pre-labeled with 3,3'-dioctadecyloxacarbocyanine perchlorate (DiO) and/or bromodeoxyuridine (BrdU). Using laser scanning confocal microscopy (three-dimensional) and immunohistochemical analysis on paraffin and frozen sections, it was identified that:

1. Cell-cell interaction: Within the NMCsphere, cells derived from bone marrow mesenchymal stem cells, rapidly form a scaffold (1 day) and a network (9 days, FIG. 8) overtime, in vitro. FIG. 8 depicts the composite MSC neurosphere nine days after cell-neurosphere integration. The MSC, identified by DO and BrdU form an axonal-dendritic like network (yellow-green).
2. Cell-cell interaction: Within the NMCsphere, cells derived from neural stem cells have a longer life span than within neurosphere alone. The NMCspheres express proteins, i.e., nestin that is normally found in immature neural cells; glial fibrillary acidic protein (GFAP) that is a specific marker for differentiated astrocytes; myelin basic protein (MBP) that is a marker of oligodendrocytes; and neuron-specific class III β-tubulin (TuJ1) that is a marker for immature neurons and microtubule associated protein 2 (MAP-2) that is a marker for neuronal cell bodies and dendrites.
3. NMCsphere-microenvironment: The size and structure of the NMCspheres are influenced by the microenvironment of the medium, i.e., they grow better in the IMDM with stem cell factor than with standard DMEM.
4. Secretion of NMCspheres: Adding the supernatant from the cultured NMCsphere into the medium DMEM and IMDM for neurospheres and MSCs, respectively, stimulated the growth of both neurospheres and MSCs. Obvious cell-cell connection and proliferation was induced with this supernatant. This suggests the NMCspheres secrete supporting substances for stem cells. These substances can be used to enhance neurogenesis.
5. Cerebro-spinal fluid (CSF) provides an optimal microenvironment to form NMCspheres that is superior to conventional medium.

Example 7

Treatment of Stroke and Brain Trauma with NMCsphere

Protocol for MSC & neurosphere transplantation in rats after MCAo and traumatic brain injury (TBI).
MCAo BrdU prelabeled MSCs and neurospheres were mixed and cultured in flasks for 7 days. At 24 hours after MCAo, rats were anesthetized with halothane and the composite NMSsphere was injected into the brain of MCAo rats (n=4). The mammals were mounted on a stereotaxic apparatus (Model 51603, Stoelting Co., Wood Dale, Ill.). Twenty spheres (diameter less than 0.2 mm) in 5 ml PBS were injected vertically by a Hamilton syringe into the right striatum at the coordinates LM=2.5 mm, VD=4.5 mm and AP=O to the bregma, and into the right cortex at LM=2.5 mm, VD=2 mm and AP=O mm. Without wishing to be bound to any particular theory, this position approximates the ischemic boundary zone. Three microliters of spheres were initially injected into the striatum and 2 ml into the cortex over a 10-minute period in each spot. The needle was retained in the cortex for an additional 5 minute interval to avoid bone marrow reflux from the injected areas to the brain surface. After injection, bone wax (W810, Ethicon) was placed on the skull to prevent the leakage of the solution. Rats were sacrificed at 14 days after MCAo.
Traumatic Brain Injury (TBI)

BrdU prelabeled MSCs and neurospheres were mixed and cultured in flasks for 7 days. At 4 days after TBI rats (n=4) were anesthetized with chloride hydrate and placed onto the stereotactic frame, and then exposed to the previous injured area. A pipette with a glass tip (0.5 mm of diameter) containing 15 prepared mixed NMCspheres (diameter of 0.25 mm) in 20 UL PBS was fixed onto the stereotactic frame. The tip of the needle was inserted at the central site of the injured area, 2.5 mm away from brain surface. Spheres were injected into the brain over 5 minutes, and then kept for an additional 5 minute interval to avoid reflux. In both sets of experiments (stroke and TBI) functional outcome measurements were measured using the rotarod and adhesive removal tests.
Results Functional benefit in both stroke and TBI was evident in rats treated with NMCspheres. These data indicate that NMCspheres can be employed for the treatment of stroke and brain injury. This composite, is a new material with potential for the treatment of CNS injury and neurodegeneration.

Example 8

Description of Novel Medium (with and without Growth Factors) Employed for the Culturing of MSCs for the Treatment of Neural Injury and Neurodegeneration Primary bone marrow cells were obtained at 48 hours after treating adult Wistar rats with 5-fluorouracil (5-FU, 150 mg/kg) and cultured in the Iscove's Modified Dulbecco's Medium (IMDM) supplemented with 10% fetal bovine serum (FBS) and stem cell factor (100 ng/ml). Adherent MSCs were resuspended in fresh IMDM with nerve growth factor (NGF, 200 ng/ml), brain derived neurotrophic factor (BDNF, 100 ng/ml) and epidermal growth factor (EGF, 20 ng/ml) up to one month. Control MSCs were cultured in the IMDM without neural growth factors. Antibodies against neuronal nuclei (NeuN), microtubule associated protein-2 (MAP-2) and glial fibrillary acidic protein (GFAP) were used for immunocytochemical identification of cultured cells.

The data indicates that cells derived from adult bone marrow stem and progenitor cells can grow in large quantities in culture and express proteins characteristic of neurons and astrocytes. Neurotrophic growth factors enhance the neural expression of cells derived from bone marrow cells in vitro. Immunocytochemical staining shows that control MSCs cultured without neurotrophic growth factors expressed the neuronal marker, NeuN (~1%, FIG. 1A) and the astrocytic marker, GFAP (~3%, FIG. 1B) at a baseline level. However, MSCs treated with neurotrophic growth factors (i.e., NGF) express NeuN (~3%, FIG. 1C) and GFAP (~30%, FIG. 1D) at an elevated level.

Bromodeoxyuridine, which is incorporated into dividing cells, and identifies newly formed DNA, was added to the medium at 72 hours before transplantation. Using immunoperoxidase with 3,3'-diaminobenzidine (DAB, brown) and counter staining by hematoxylin, bone marrow cells are identified by the antibody against BrdU. The number of MSCs labeled with BrdU was observed to be ~90% in vitro.
Discussion The data demonstrate that cultured adult bone marrow cells, particularly marrow stromal cells (MSCs), survive and differentiate into parenchymal like cells in the adult rodent brains after ischemia, brain and spinal cord trauma, and Parkinson's disease, and that bone marrow promotes prominent proliferation, differentiation and migration of ventricular zone/subventricular zone (VZ/SVZ) NSCs.

Pluripotent bone marrow cells become glia in normal rat brain (Azizi et al., 1998), and facilitate cell proliferation and cell-specific differentiation after MCAo. The bone marrow transplantation experiment requires a sensitive means of monitoring the fate of the bone marrow cells. Help came from the bone marrow cells carrying tracers and markers, such as BrdU, CD34, nestin, PCNA. Pluripotent hematopoietic stem cells and mesenchymal stem cells from the adult bone marrow exposed to the new ischemic microenvironment after MCAo are triggered to proliferate and differentiate into neuronal (MAP-2, NeuN) and glial cell (GFAP) phenotypes. Fresh bone marrow or stroma humoral factors are also a source of differentiating factors and provides the chemotatic microenvironment to enhance the proliferation, migration and differentiation of neural stem cells from VZ/SVZ.

The VZ/SVZ of the mammalian forebrain is a region of germinal matrices that develops late in gestation, enlarges, and then diminishes in size, but persists in a vestigial form throughout life (Gage 1998). In the normal adult brain, the absence of forebrain neuronal production reflects not a lack of appropriate neural stem cells, but rather a tonic inhibition and/or a lack of postmitotic trophic and migratory support. Although the signals that trigger the quiescent central nervous system (CNS) stem cells within the normal VZ/SVZ to enter the cell cycle have yet to be resolved, the data show that a lesioned CNS is a different environment than an intact CNS and markedly alters the terminal differentiated phenotype of the neural stem cells. Importantly, the VZ/SVZ in the adult forebrain is not a passive ischemia-threatened zone, located far from the ischemic areas (FIGS. 3F-H), but is an active tissue providing cells to reconstruct brain. VZ/SVZ cells proliferate and differentiate into neuronal and glial phenotypes after MCAo. The survival of neurons arising from adult NSCs is dictated by both the availability of a permissive pathway for migration and the environment into which migration occurs. New neurons depart the VZ/SVZ to enter the brain parenchyma via radial guide fibers, which emanate from cell bodies in the ventricular ependyma in adult rat (FIGS. 2K-L), and provide a permissive pathway for migration as found during development (Rakic 1972). Mitosis within the graft and VZ/SVZ shows that ischemic injured brain together with the transplanted cells reverts to an early stage of development to promote repair. The data are consistent with the observation that adult brain can form new neurons (Gage 1998).

Example 9

Effects of Bone Marrow Stromal Cells Injected Via Different Routes (Intraarterial Versus Intravenous) after Stroke in Rats The data disclosed herein demonstrate the beneficial effects of administering rat bone marrow stromal cell (rBMSC) to rats that have undergone stroke using intraarterial (IA) or intravenous (IV) delivery systems. In the present experiments, comparative effects of rBMSCs injected via IA or IV on neurological function, neurogenesis, and angiogenesis in ischemic rats were analyzed. Young adult rats were subjected into middle cerebral artery occlusion (MCAo) for two hours. After 24 hours, $2 \times 10^6$ rBMSCs or phosphate buffered saline (PBS) were infused into the carotid artery or the tail vein of the rat. The rats were sacrificed at day one (n=6), day seven (n=6), day fourteen (n=6) and day twenty eight (n=12) after cell injection, (half mammals for IA and half for IV at every time point); whereas the control mammals (n=6 for IA and n=6 for IV) were sacrificed at day twenty eight after PBS injection. Behavioral tests (an adhesive-removal test and a modified Neurological Severity Score, mNSS) were performed at 1, 7, 14, 21 and 28 day after MCAo. BrdU immunohistochemistry was used to evaluate endogenous neurogenesis in both the subventricular zone (SVZ) and the subgranular zone (SGZ). Immunohistochemistry was employed to measure angiogenesis in the ischemic boundary zone (IBZ). Significant ($P<0.05$) recovery of the adhesive-removal test and mNSS were found in both IA and IV groups as early as day seven and persisted to at least day twenty eight after cell injections compared with control mammals that did not receive injection of rBMSCs. Immunohistochemistry results showed that the number of BrdU positive cells in the SVZ and SGZ significantly increased ($P<0.05$) during 7-14 day after stroke and returned to baseline at day twenty eight. Quantitative analysis using immunohistochemistry techniques indicated that angiogenesis was significantly enhanced ($P<0.05$) by the rBMSC administration and persisted for at least day twenty eight in the IBZ after the onset of stroke. It was observed that no significant difference between IA and IV groups in all the above examinations was detected at this cell dose. Based on the present disclosure, rBMSCs delivered to the ischemic brain through both intracarotid and intravenous routes provide therapeutic benefits after stroke.

Example 10

Correlated Expression of MT1-MMP and IGF-1 Genes with Neurological Recovery in Ischemic Rats Treated with Human Marrow Stromal Cells The data disclosed herein demonstrate that human bone marrow stromal cells (hMSCs) can enhance neurogenesis and promote neural stem cell proliferation and migration following administering into an ischemic rat. Without wishing to be bound to any particular theory, it is believed that the neurological recovery in an ischemic rats using hMSC is determined by enhanced gene expression in the ischemic area induced by hMSCs. To elucidate the molecular mechanisms underlying the hMSC effect on stroke, differently expressed genes in the treated and untreated ischemic brain tissue were identified. Rats were subjected to permanent occlusion of the right middle cerebral artery (MCAo) alone (n=18) and were injected intravenously with $3 \times 10^6$ hMSCs (n=18) at day one after MCAo. Functional outcome was measured at 0, 1 and 7 day after MCAo by a modified Neurological Severity Score, mNSS. A number of genes including, but not limited to, Membrane-Type 1 matrix metalloproteinase (MT1-MMP), insulin-like growth factor (IGF-1) and its receptor IGF-1R in the ischemic boundary zone (IBZ) were tested using RT-PCR at day 0, 2 and 7 after MCAo in rats treated with hMSC, compared with control rats not receiving injection of hMSCs. RT-PCR analysis demonstrated a significant increase of IGF-1 and MT1-MMP mRNA at day two after MCAo which was observed to persist for at least day seven. IGF-1 mRNA levels in the IBZ of rats receiving injection of hMSC at day two and day seven after MCAo were significantly increased compared with that of non hMSC treated mammals. MT1-MMP mRNA levels in hMSC treated rats exhibited no distinct difference from that of the non treated mammal at day two, but there was a significant increase in MT1-MMP mRNA at day seven in hMSC treated rates as compared with non treated mammals. It was also observed that there was no significant difference in IGF1-R mRNA expression among the normal, ischemic and hMSC treated rats at any time points tested. These data indicate that hMSC treatment can achieve a neurorestorative effect through multiple mechanisms in the IBZ. Elevated IGF-1, in the presence of abundant IGF-1 receptor, can promote neuron survival and regeneration during the hMSC treatment of these ischemic rats. MT-1 MMP, an important membrane-bound MMP, has been suggested to play a central role in mediating cell surface focal proteolysis pathways. IGF-1 has been demonstrated to up-regulate MT1-MMP expression. The present disclosure demonstrates that MT1-MMP may be functionally linked to neuronal survival and regeneration mediated by IGF-1 in the IBZ.

Example 11

Treatment of Stroke in Rats with Human Bone Marrow Stromal Cells

The data disclosed herein addresses whether treatment of stroke in rats using xenogeneic human bone marrow stromal cells (hMSCs) necessitates the use of an immunosuppressive agent, for example, cyclosporin A (CsA), and whether CsA affects the neurological response to stroke and treatment with hMSCs in rats. hMSCs were obtained from three healthy human donors. Adult Wistar rats were subjected to 2 hours of middle cerebral artery occlusion (MCAo). Four groups of ischemic rats (n=6, per group) were subjected to: 1) MCAo alone without treatment; 2) 15 mg/kg CsA by gastric feeding daily beginning at one day after MCAo for 27 days; 3) tail intravenous injection of $3 \times 10^6$ hMSCs at one day after MCAo; and 4) co-treatment with hMSCs and CsA after MCAo. Functional outcome was measured by using an adhesive-removal patch test and a modified Neurological Severity Score (mNSS) before stroke and at 1, 7, 14, 21 and 28 day after stroke. A human-specific antibody (Mab1281) against cellular nuclei was used to identify hMSCs within the brain tissue. Since unwanted activation of T-lymphocytes promotes graft rejection, human graft-versus-rat host cytotoxic T lymphocyte (CTL) response was measured using a $^{51}Cr$ assay to determine the lytic effect. It was observed that no stroke rats died after hMSC injection into the rats. Significant functional recovery of adhesive-removal ($p<0.05$) at 14, 21 and 28 day, and mNSS ($p<0.05$) at 21 and 28 day was found in rats treated with hMSCs (Group 3 and 4), compared to control ischemia rats, which did not receive hMSC injection (Group 1 and 2). Few mAb1281 positive cells (approximately 500-3,000 positive cells per brain) were detected in recipient rats in Group 3 (1,283±592) and Group 4 (1,431±727); however, no significant difference was observed between these groups. It was also observed that CsA did not have an apparent effect on neurological functional recovery after stroke with or without hMSC treatment. There was no evidence of hMSC induction of CTL response both in vitro and in vivo. The data indicate that there is no apparent complicating immune response that obscures the therapeutic benefit of hMSC treatment in stroke tats. Thus, CsA immunosuppression is not needed as an adjunctive therapy when administering hMSCs to a rat.

Example 12

Allogeneic Rat Marrow Stromal Cells Promote Brain Remodeling without Immunologic Sensitization in Stroked Rats The present disclosure addresses the effects of allogeneic (allo-) and syngeneic (syn-) rat bone marrow stromal cell (rBMSC) for the treatment of stroke with respect to functional outcome based on immune reaction, glial scar formation and glial-axonal architecture. Female Wistar rats (n=25) were subjected to middle cerebral artery occlusion (MCAo) for two hours. At 24 hour after MCAo, rats were injected intravenously with phosphate buffered saline (PBS, n=8), syn-Wistar strain rBMSCs ($3 \times 10^6$/rat, n=8), or allo-ACI strain rBMSCs ($3 \times 10^6$/rat, n=9). Neurological functional recovery was performed using the Neurological Severity Score, adhesive-removal patch and Corner tests. Rats were sacrificed at day twenty eight after treatment, and were bled to determine antibody titers to rBMSCs. Lymphocytes collected from mesenteric and cervical lymph nodes were cultured with irradiated syn- or allo-spleen cells to determine T cell proliferative responses against donor alloantigens using the Mixed Lymphocyte Reaction assay. Antibody titers to rBMSCs were determined by a flow cytometry method. In situ hybridization and double immunostaining techniques were employed for male Y-chromosome bearing rBMSC and brain cell type identification. Significant functional recovery ($p<0.05$) was found in both groups treated with rBMSCs (syn- or allo-) compared to PBS controls, but no difference was detected between syn- and allo-rBMSC treated rats. Similar numbers of Y-chromosome$^+$ cells were detected in the syn- and allo-rat brains at twenty eight days after treatment. Astrocyte proliferation was prominent (BrdU+-GFAP+, hyperplasia) in the ischemic brain and exceeded cell proliferations in other cells. It was observed that the thickness of the scar wall decreased ($p<0.05$), and the axonal density as measured by Bielshowsky silver staining increased ($p<0.05$) in areas where reactive astrocytes were present (GFAP+ hypertrophy) in the scar boundary zone (SBZ) and in the subventricular zone (SVZ) of the rBMSC treated rats, compared with the non-treated rats. Moreover, axonal projections exhibited an overall orientation parallel to elongated processes of reactive astrocytes and toward lesion areas in the SBZ and SVZ of the rBMSC treated rats, suggesting that rBMSCs may enhance reactive astrocyte-related axonal repair in adult brain. No evidence of T cell priming or humoral antibody production rBMSC was observed in recipient mammals after treatment with allogeneic ACI-rBMSCs. Based on the present disclosure, both syn- and allo-rBMSC treatment of stroke in rats improved neurological recovery and enhanced brain remodeling with no indication of immunologic sensitization.

Example 13

BMSC Confer Post-Ischemic Protection Via Increased Akt and Erk and Growth Factor Production within Neighboring Astrocytes It has been demonstrated that treatment of stroke using bone marrow stromal cells (BMSCs) significantly improves functional outcome, and reduces apoptosis in the brain. Astrocytes have been shown to be the first cells to suffer ischemic insult among all types of neural cells. The present disclosure provides insight on the interaction between BMSCs and astrocytes after ischemic insult. The data disclosed here addressed the effect of rat BMSCs (rBMSCs) on post-ischemia induced apoptosis and cell death of astrocytes, as well as the mechanisms of these effects using an in vitro ischemic model. After a four hour ischemic incubation in an anaerobic chamber, astrocytes were co-cultured with rBMSCs in non-ischemic conditions (as post-ischemic incubation) for an additional four hours. Astrocytes cultured without the presence of rBMSCs (control group) depicted evident morphological and biochemical apoptotic features. A large number of condensed nuclei were observed, and many cells appeared as dark detached spheres or oval-shaped bodies. A cell viability assay demonstrated that about 35% of the astrocytes were not viable. However the introduction of rBMSCs remarkably reduced the apoptosis and cell death (to about 1.5%, P<0.01) in astrocytes, and most of the astrocytes appeared as a confluent cobblestone layer. BrdU-immunostaining revealed a higher proliferation rate in the co-cultured astrocyte group compared to the control group. Western blot analysis and real-time quantitative PCR demonstrated that rBMSCs drastically increased Erk1 and Akt at both protein and RNA level in post-ischemic astrocytes. Additionally, Western blot analysis also revealed that co-culturing astrocytes with rBMSCs upregulated the phosphorylation of Erk1 and Akt in astrocytes. Astrocytes treated with MEK inhibitor (U0126) or PI3K inhibitor (LY29004) underwent significant apoptosis and cell death similar to the post-ischemic control group. Co-culturing astrocytes with rBMSCs significantly (P<0.01) attenuated this U0126 and LY29004 mediated insult. Furthermore, real-time PCR demonstrated that rBMSC co-culture increased RNA levels of bFGF, BDNF, and VEGF in astrocytes that had suffered ischemia. These results indicate that rBMSCs enhance the recovery of post-ischemia astrocytes by stimulating the activation of MEK/Akt and PI3K/Erk pathways in astrocytes, and increasing growth factor production by astrocytes.

Example 14

Treatment of Stroke in Rats with Human Marrow Stromal Cells Decreases Axonal Loss and Demyelination Axonal loss and demyelination are frequently observed in ischemic cerebrovascular diseases and contribute to neurological functional impairment. It has been demonstrated that human marrow stromal cells (hBMSCs) improved neurological functional recovery in ischemic rats. The present disclosure, addresses the effect of hBMSCs on axonal fibers in ischemic brain. Rats were subjected to permanent middle cerebral artery occlusion (MCAo) and injected intravenously with $3 \times 10^6$ hBMSCs or phosphate buffered saline (PBS) (n=6 per group) at one day after MCAo, and sacrificed at fourteen days after MCAo. Axon and myelin damage was examined using Bielshowsky and Luxol fast blue double staining, respectively, in the MCAo rats receiving hBMSC or PBS treatment. Nerve fiber damage was found in the white matter (WM) of the striatum (ST) and corpus callosum (CC) of the ipsilateral hemisphere after MCAo with PBS treatment, and involved both axonal and myelinated components. Demyelination was more severe than axon loss (10.4±2.3% vs 3.7±0.7%), indicating that the myelin is more susceptible to ischemia than the axon. The surviving WM area within the ipsilateral CC significantly increased compared to the corresponding area of the contralateral CC. Enhanced density of axons was observed in the WM bundles in the ST and WM in the CC of the ischemic boundary zone, indicating that a self-neurorestorative mechanism was initiated. It was observed that no significant change in the contralateral CC area among normal, PBS and hBMSC treatment groups. hBMSC treated MCAo mammals demonstrated significantly reduced areas of demyelination (3.7±0.2% vs 10.4±2.3%) and axon loss (1.8±0.4% vs 3.7±0.7%), in the ipsilateral ST when compared to PBS treated controls. It was observed that the morphologically intact areas of the ipsilateral CC were significantly increased (19.8±4.5% vs 11±6.7%); and the density of axons were enhanced (27.5±6.3% vs 19.8±5.6%) in the ST and CC of the ischemic boundary zone in the hBMSC treated rats compared with the PBS controls. The present disclosure suggests that axonal and myelination remodeling may contribute to improved functional recovery after treatment of stroke with hBMSCs.

In summary, the data indicate that intracerebral and intravascular bone marrow transplantation after stroke neural injury and Parkinson's disease significantly improves functional recovery. Transplantation also enhances the proliferation and differentiation of exogenous bone marrow stem cells and endogenous NSCs. Bone marrow aspirations and biopsies have been employed in the diagnosis and treatment of clinical diseases. Bone marrow transplantation provides a new avenue to induce plasticity of the injured brain and spinal cord and provides a therapeutic strategy for treatment of neural injury and neurodegeneration.

In addition, a new substance is identified herein, a composite of MSCs and neurospheres, which when transplanted into brain after stroke or trauma, improves functional recovery.

Example 15

Bone Marrow Stromal Cells Reduce Axonal Loss in the Experimental Autoimmune Encephalomyelitis (EAE) Mice The following experiments were designed to investigate the effects of transplanting human bone marrow stromal cells (hBMSCs) or otherwise hMSCs in an experimental model of multiple sclerosis (MS). Such an experimental model involves assessing remitting-relapsing and axonal loss in experimental autoimmune encephalomyelitis (EAE) mice.

The present disclosure demonstrates that hBMSCs were able to reduce axonal loss in an MS model. Briefly, EAE was induced in SJL/J mice (n=63) by injection with proteolipid protein (PLP). Mice were injected intravenously with hBMSCs (n=26) or PBS (n=37) on the day of clinical onset and neurological function was measured daily (score 0-5) until 45 weeks after onset. Mice were sacrificed at week 1, 10, 20, 35 and 45. Double staining for Luxol fast blue and Bielshowsky was used to identify myelin and axons, respectively. Immunohistochemistry was performed to measure the expression of nerve growth factor (NGF) and MAB1281, a marker of hBMSCs. hBMSC treatment significantly reduced the mortality of EAE mice, and significantly improved functional recovery in EAE mice compared to PBS treatment. Axonal density in the EAE striatum and corpus callosum was significantly increased in the hBMSC treatment group compared with that of the PBS treatment group. NGF$^+$ cells significantly increased in the hBMSC treated mice compared to PBS controls at 1, 10, 20, and 45 weeks. Most of the NGF$^+$ cells were identified as brain parenchymal cells. Less than 5% of MAB1281$^+$ cells co-localized with NG2$^+$, a marker of oligodendrocyte progenitor cells. About 10% of MAB1281$^+$ cells co-localized with GFAP and MAP-2, a marker of astrocytes and of neurons, respectively. It was observed that hBMSCs improved functional recovery and therefore provides a therapy aimed at axonal protection in EAE mice, in which NGF plays an important role.

The Materials and Methods used in the experiments presented in this Example are now described.

Cell Culture hBMSCs were isolated, grown and tested, using methods adopted from Zhang et al. (2005, Exp. Neurol. 195:16-26). Briefly, bone marrow was obtained from adult human donors and the nucleated cell fraction was cultured with Dulbecco's Modified Eagle Medium-low glucose media and 10% fetal bovine serum. The adherent cells were harvested, passaged and cryopreserved in appropriate dose related aliquots in Plasma-Lyte containing human serum albumin and dimethyl sulfoxide. The cells are tested for purity at the end of each passage by flow cytometry. The BMSCs were positive for MHC class I, CD29, CD90, CD105, CD13, CD44, CD63, CD73 and CD166. The cells were negative for MHC class II, CD45, CD14 and CD34.

EAE Induction and Animal Groups

Myelin proteolipid protein (PLP) (p139-151; HSLGK-WLGHPDKF, SEQ ID NO:1; SynPep Corporation, Dublin, Calif.) was used for immunization. The purity of the peptide was greater than 95% as measured by High Performance Liquid Chromatography. EAE was induced in female SJL/J mice (8-10 week old, Jackson Laboratory, Bar Harbor, Me.) by subcutaneous injection with 25 ug PLP dissolved in 50 ul complete Freund's adjuvant (CFA) (Difco Laboratories, Livonia, Mich.). On the day of immunization and 48 hours post immunization, 200 ng pertussis toxin (PT) (List Biological laboratories, Inc. Campbell, Calif.) in 0.2 ml phosphate buffered saline (PBS) was injected into the mouse tail vein (Youssef et al., 2002, *Nature* 420:78-84; Zhang et al., 2005, *Exp. Neurol.* 195:16-26). Mice were randomly divided into: 1) hBMSC treatment group (n=26): hBMSCs ($2\times10^6$ per mouse) were administered intravenously in 1 (one) ml total fluid volume PBS on the day of clinical symptom onset (score≥1); and 2) PBS treatment group (n=37): PBS (1 ml) was injected into the tail vein of the EAE mice on the day of clinical symptom onset as EAE controls. An additional control normal group (n=6) consisted of mice without immunization.

Neurological Functional Measurement

Mice in the hBMSC treatment group and PBS treatment group were scored daily for clinical symptoms of EAE, as follows: 0, healthy; 1, loss of tail tone; 2, ataxia and/or paresis of hindlimbs; 3, paralysis of hindlimbs and/or paresis of forelimbs; 4, tetraparalysis; 5, moribund or dead (Pluchino et al., 2003, *Nature* 422:688-694). Neurological functions of EAE were tested in mice treated with hBMSCs or PBS daily until 45 weeks after clinical symptom onset.

Histopathology and Immunohistochemistry

EAE mice treated with PBS or hBMSCs were euthanized at 1, 10, 20, 35 and 45 weeks after clinical symptom onset. Brain tissue (ranging from bregma +1.18 mm to bregma −1.82 mm) were fixed in 4% of paraformaldehyde and divided into 4 serial sections per mouse. These tissue blocks were embedded in paraffin and cut into 6 μm thick coronal slides.

Double staining for Luxol fast blue and Bielshowsky was used to demonstrate myelin and axons, respectively (Karnezis et al., 2004, *Nat. Neurosci.* 7:736-744; Pluchino et al., 2003, *Nature* 422:688-694; Furlan et al., 2001, *J. Immunol.* 167:1821-1829). After staining, nuclei appeared colorless; myelin turquoise and axons appeared black on a pale grey/blue background.

To identify the expression of NGF, a rabbit polyclonal antibody against NGF (1:300, Santa Cruz Biotechnology Inc., Santa Cruz, Calif.) was used. To identify the fate of injected hBMSCs in the CNS of EAE mice, slides were treated with a monoclonal antibody specific to human nuclei (MAB1281; 1:500, Chemicon, Temecula, Calif.). Double immunofluorescence labeling was performed to identify the relationship of NGF with neural cells and hBMSC with neural cells. Antibodies against MAP-2 or NeuN (markers of neurons), glial fibrillary acidic protein (GFAP, a marker for astrocytes) and NG2 (a marker for progenitor oligodendrocyte cell) were used to identify parenchymal cells. Negative control slides for each animal received identical preparations for immunostaining, except for the fact that primary antibodies were omitted.

Quantification and Statistical Analysis

Neurological functional tests and tissue slides were evaluated by a blinded examiner to the treatment status of each animal. Mice were monitored for mortality up to 45 weeks (i.e., if the mice were not sacrificed earlier than 45 weeks). Mortality rates were compared between the hBMSC treated and PBS treated groups using the log-rank survival analysis with Kaplan-Meier curves plotted for survival rates over time.

The functional score, ranging from 1 to 5, was measured on the day before the treatment and daily during and after the treatment up to 45 weeks after EAE. Subgroups of mice were sacrificed at week 1 (n=7 in each group), week 10 (n=7 in the PBS group; n=4 in the hBMSC group), week 20 (n=4 in each group), week 35 (n=6 in the PBS group, n=4 in the hBMSC group) and week 45 (n=4 in each group) for measurement of morphological changes. In the case where a mouse died prior to an upcoming sacrificed time, the functional score 5 was given for that sacrifice time.

Normality of the functional recovery score was evaluated using Generalized Estimating Equations (GEE) on the ranked data. Without wishing to be bound by any particular theory, GEE was chosen because it has fewer restrictions on the data distribution. Analysis of variance for repeated measures including the independent factor of the treatment and dependent factor of the time was also employed. Analyses were performed on scores measured from week 1 to week 45. The analysis began testing for the treatment by time interaction, followed by testing the main effect of hBMSC or time, if no interaction was observed at the 0.05 level. A subgroup analysis of hBMSC effect at each time point was conducted, if an interaction or time effect was detected. The hBMSC by time interaction indicated that the effect of hBMSC on the functional recovery depended on the time after EAE. Functional outcome was reported as mean SD per time point for data illustration.

Axonal loss in the white matter of the corpus callosum and striatum in the EAE brain was assessed. The axonal density was counted on an average of four brain sections (ranging from bregma +1.18 mm to bregma −1.82 mm) per mouse (at 40× magnification). Data were obtained using a 3-CCD color video camera (Sony DXC-970 MD) and interfaced with ImageJ image processing program (National Institute of Mental Health, Bethesda, Md.). The axonal density was presented as a proportional area. To measure immunoreactive cells, numbers of NGF[+] and MAB1281[+] cells were counted on an average of 4 brain sections (ranging from bregma +1.18 mm to bregma −1.82 mm) per mouse (at 40× magnification), using a 3-CCD color video camera (Sony DXC-970 MD) interfaced with the Micro Computer Imaging Device (MCID) analysis system (Imaging Research Inc. St. Catharines, Ontario, Canada). The density of immunoreactive cells was calculated by dividing the number of counted cells by the scan area, presented as numbers per $mm^2$. Data was presented as mean±SD. Significance between the two groups was examined using a t-test. A value of p<0.05 was considered significant.

Figure 12B:
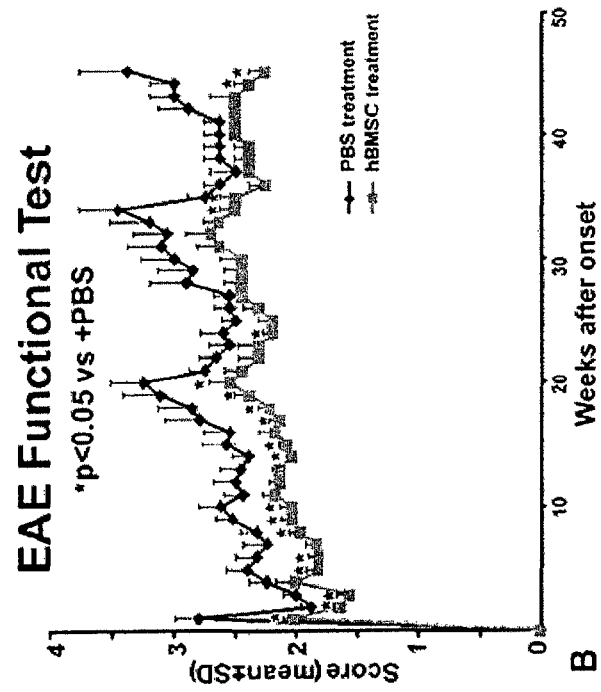
FIGS. 12A and 12B, is a series of images demonstrating that treatment with hMSCs improves survival rate and neurological functional recovery in experimental autoimmune encephalomyelitis (EAE) mice.
Figure 12A:
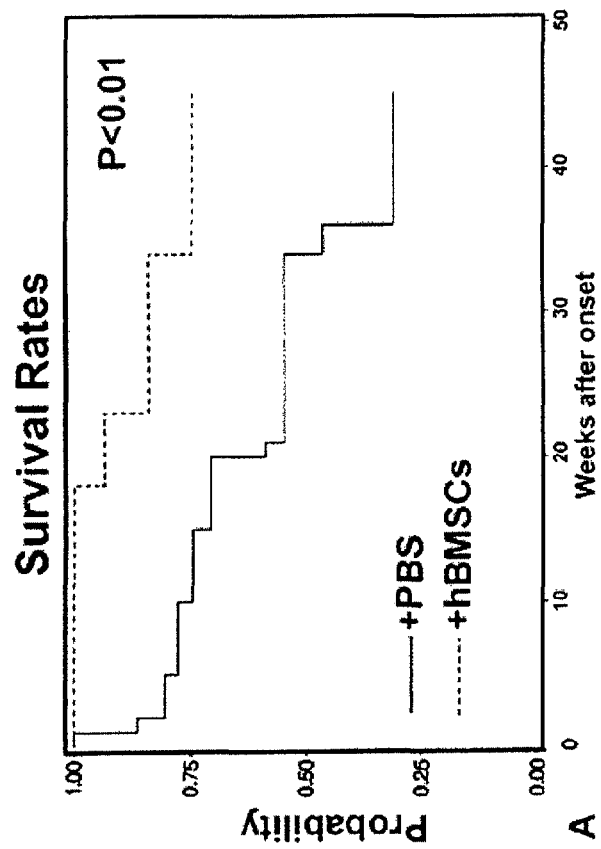

The results of the experiments presented in this Example are now described.

hBMSC Treatment Improves Survival Rate And Neurological Functional Recovery in EAE Mice Without wishing to be bound by any particular theory, since MS is a chronic disease course, the mortality and function of the mice were measured up to 45 weeks after clinical onset. It was observed that mice in the hBMSC treated group had significantly higher survival rates as compared to the PBS treated group. A total of 63 EAE mice were employed in the study. Survival rates for hBMSC treated mice at weeks 10, 20, 35, and 45 were significantly higher than those in the PBS group (p<0.01) (FIG. 12A).

Experiments were designed to evaluate whether the administration of BMSCs on the day of clinical onset was an effective treatment. It was observed that there were several remitting-relapsing courses of disease within 45 weeks after clinical symptom onset (FIG. 12B). The relationship between hBMSC treatment and time was significant (p<0.05) and therefore, pair-wise comparisons at each time point were conducted with the mean and SD of the functional scores. Functional scores were significantly lower among mice treated with hBMSCs compared with PBS treated mice as early as 1 week up to 45 weeks. Before week 20, functional scores were significantly lower in the hBMSC group compared with the PBS group at 70% time points, after week 20, there were significant difference between 2 groups at 20% time points. The significance of hBMSCs effects were sustained to 45 weeks (p<0.05) (FIG. 12B).

hBMSC Treatment Increases Axonal Density in The White Matter of The EAE Brain

Figure 13:
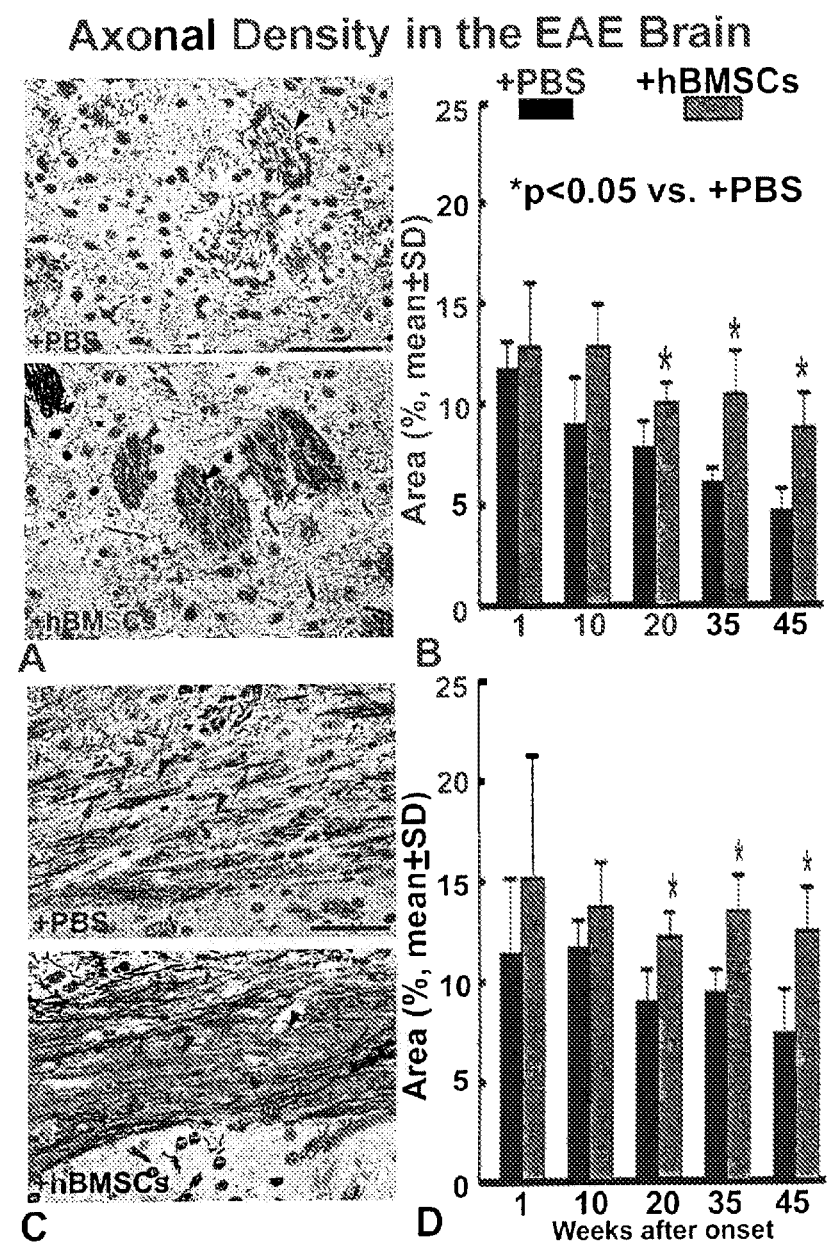
FIG. 13, comprising

Due to the effective neurological functional benefit of hBMSC treatment, experiments were designed to address whether BMSC treatment affects axonal loss. The proportional area of axonal loss was significantly reduced in the striatum (FIGS. 13A and 13B) and corpus callosum (FIGS. 13C and 13D) of the hBMSC treatment group compared with that of the PBS treatment group at 20, 35 and 45 weeks after clinical onset. These data demonstrate that the long term functional effect of BMSCs is associated with the reduction of axonal loss in the EAE brain.

Administration of hBMSCs Increases NGF Expression in the CNS of EAE Mice

Figure 14C:
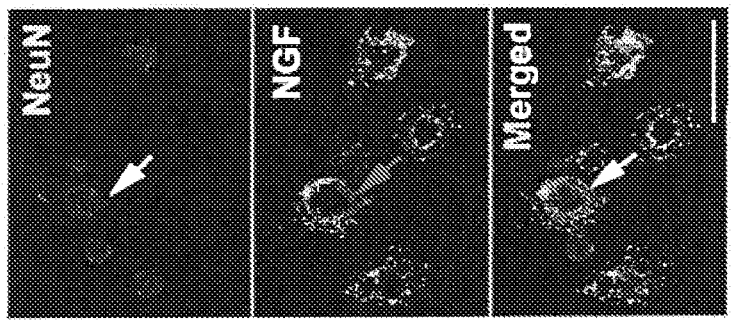
FIGS. 14A through 14C, is a series of images demonstrating that administration of hMSCs increases NGF expression in the CNS of EAE mice.
Figure 14B:
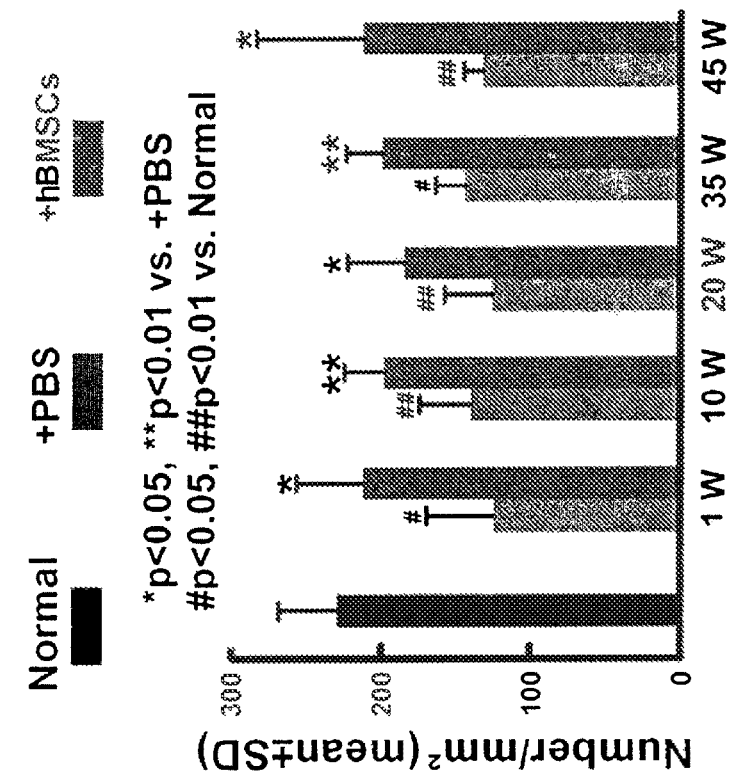
Figure 14A:
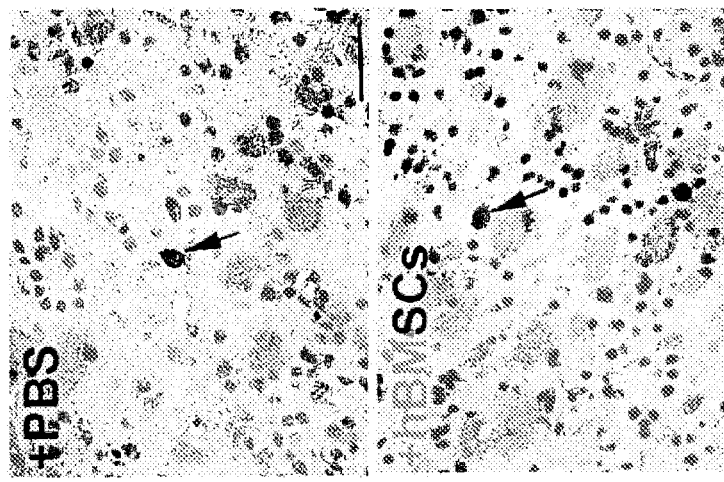

Without wishing to be bound by any particular theory, it is believed that BMSC treatment reduces axonal loss and improves neurological outcome by augmenting expression of NGF in parenchymal cells. The following experiments were designed to measure NGF cell expression in the white matter of the striatum and corpus callosum. It was observed that NGF was present in the normal brain tissue of mice. After onset of EAE, cellular expression of NGF significantly decreased in the brain during the acute and chronic phase of EAE. hBMSC treatment significantly increased the number of NGF reactive cells in the brain at 1, 10, 20, 35 and 45 weeks compared with the PBS treatment (FIGS. 14A and 14B). Furthermore, double staining shows that hBMSCs stimulated the brain parenchymal cells to express NGF. Approximately, 50-70% of NGF$^+$ cells co-localized with NeuN$^+$ cells (FIG. 14C).

hBMSCs are Present in the EAE Brain

Figure 15:
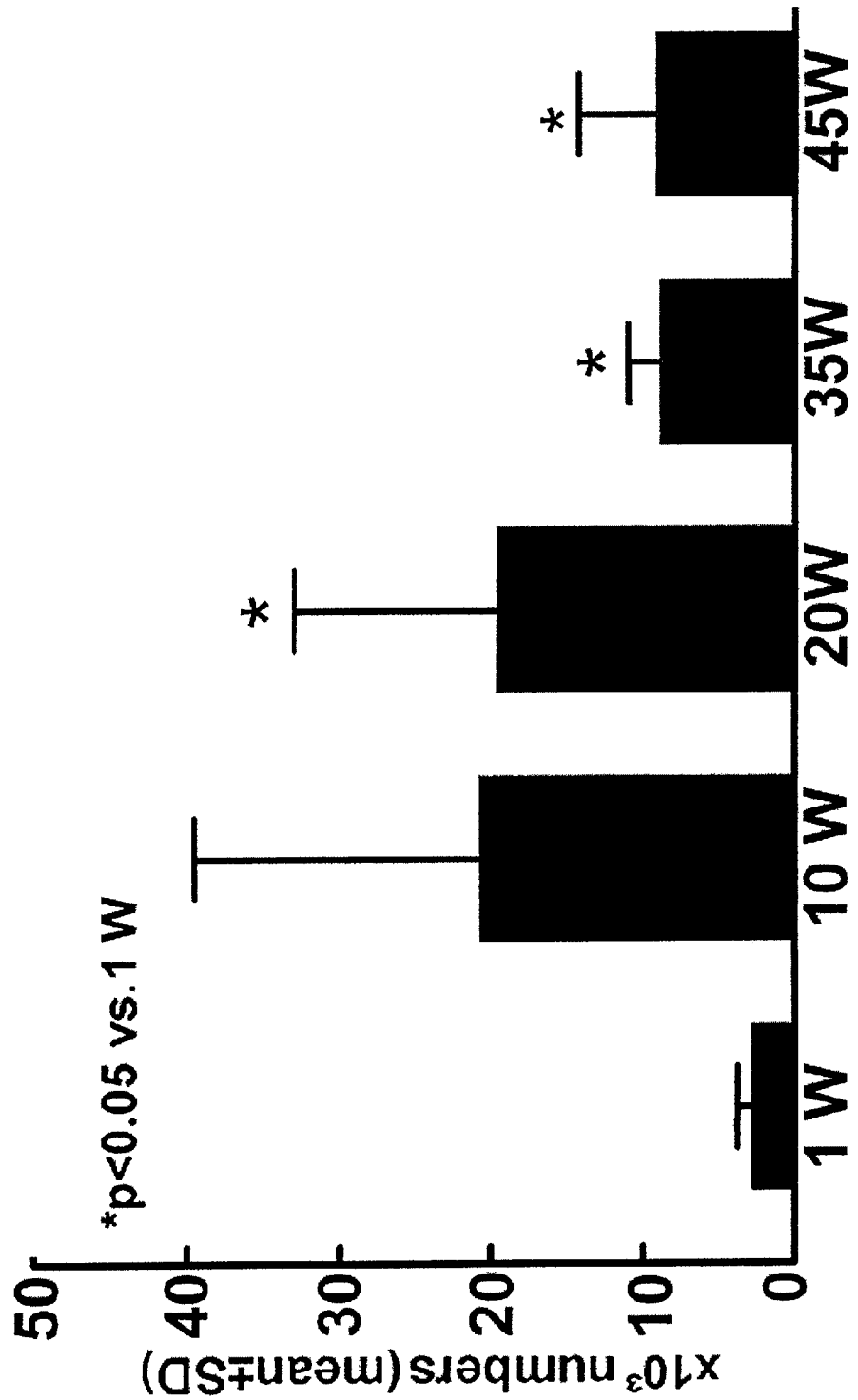
FIG. 15 is a graph demonstrating that hMSCs are present in EAE brain following transplantation as measured by the presence of MAB1281 cells.
Figure 16:
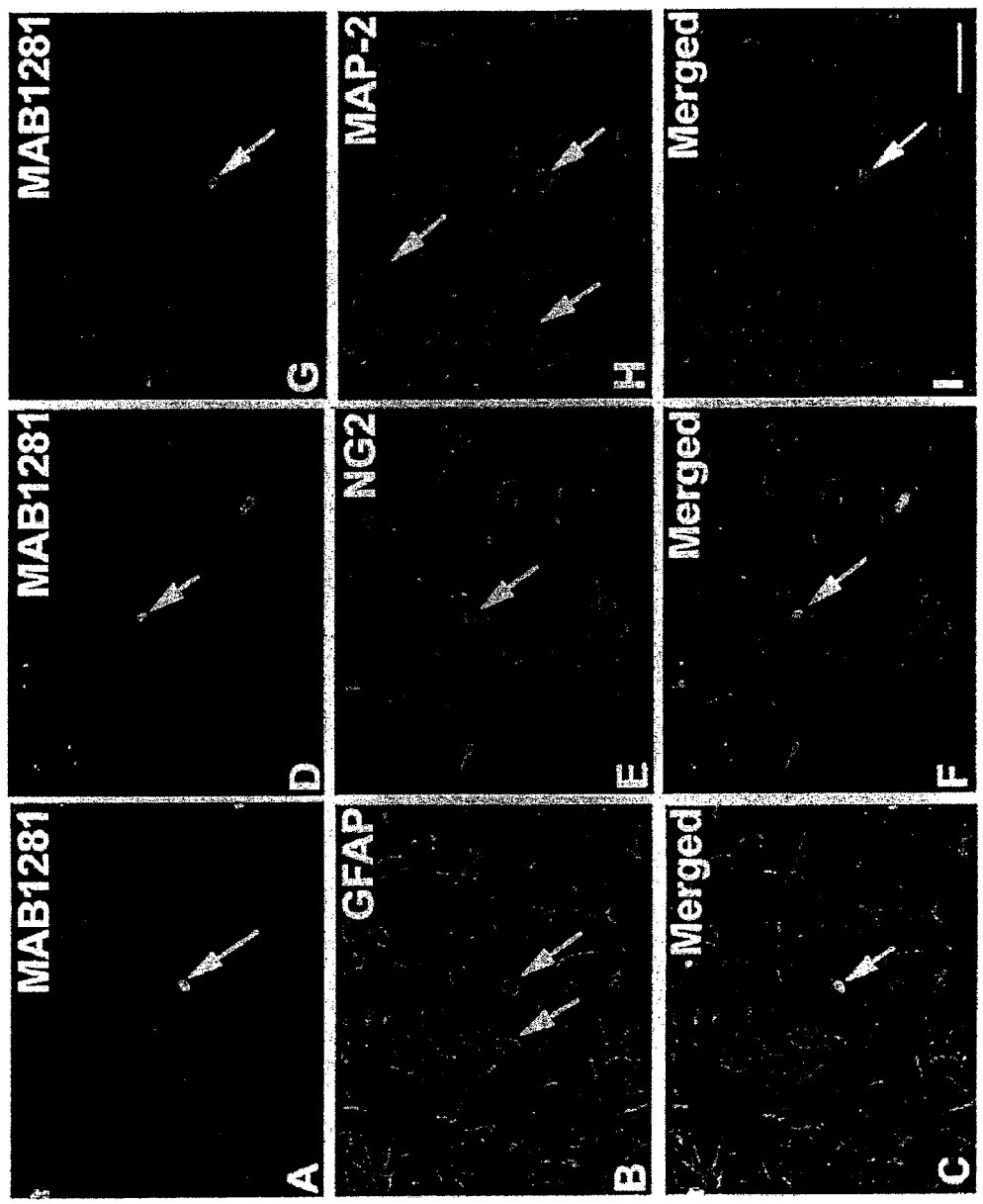
FIG. 16, comprising

MAB1281$^+$ cells were present in the CNS from as early as 1 week up to 45 weeks following hBMSC transplantation. Most of the cells were located in the striatum and the corpus callosum. The number of MAB1281$^+$ cells significantly increased at 10, 20, 35 and 45 weeks compared to the MAB1281$^+$ cells at 1 week (FIG. 15). Double staining revealed that less than about 5% of MAB1281$^+$ cells co-localized with NG2$^+$ cells and about 10% of MAB1281$^+$ cells co-localized with MAP-2$^+$ cells and GFAP$^+$ cells, respectively, (FIG. 16). These data demonstrated that the therapeutic effect of BMSCs on EAE was not a result of cell replacement.

BMSCs for the Treatment of Degenerative Diseases of the CNS

The results presented herein demonstrate that transplantation of hBMSCs at the day of clinical EAE symptom onset improved survival rates and reduced disease severity, having a statistical significance from 1 week up to 45 weeks after disease compared with PBS treatment.

Since MS is an immune-mediated demyelinating and degenerative disease of the CNS, with lesions predominantly occurring in the CNS white matter, it is believed that the first step in combating MS is to suppress the immune onslaught. However, these strategies alone are insufficient for treating the chronic progressive disability that is the ultimate outcome of the disease (Chitnis et al., 2005, *Curr. Drug Targets Immune Endocr. Metabol. Disord.* 5:11-26).

The data presented herein revealed that few MAB1281$^+$ cells co-localized with neural cell markers. Although the injected hBMSCs express brain cell phenotypic proteins, the data does not indicate true differentiation and neuronal or glial cell function. Thus, it is believed that the beneficial outcome from hBMSC treatment is not a result of a cell replacement therapy. Rather, it is believed that BMSCs secrete a series of growth factors and induce expression of growth factors within the parenchymal cells.

In the present study, it was observed that NGF expression increased after hBMSC treatment. NGF stimulates axonal repair (Walsh et al., 1999, *J. Neuroscience* 19:4155-4168; Jones et al., 2003, *J. Neurosci.* 23:9276-9288) and induces axon growth (Zhou et al., 2004, *Neuron* 42:897-912). Moreover, axon repair is present not only in acute, but also in chronic CNS injury (Grill et al., 1997, *Exp. Neurol.* 148:444-452). NGF also enhances the survival of differentiated oligodendrocytes (Cohen et al., 1996, *J. Neurosci.* 16:6433-6442), and stimulates oligodendrocyte growth and/or differentiation (Aloe et al., 1998, *Arch. Ital. Biol.* 136:247-256). In addition to its neurotrophic effect, NGF exhibits immunomodulatory effects (Aloe et al., 1997, *Allergy* 52:883-894; Flugel et al., 2001, *Eur. J. Immunol.* 31:11-22; Fainzilber et al., 2002, *J. Neurosci.* 3:1029-1034; Aloe et al., 2004, *Ann. Ist Super Sanita.* 40:89-99), such as suppression of MHC II inducibility in microglia and stimulation of memory B cells and Th2 responses (Bracci-Laudiero et al., 2002, *J. Neuroimmunol.* 123:58-65; Bonini et al., 2003, *Int. Arch. Allergy Immunol.* 131:80-84; Bracci-Laudiero et al., 2005, *Blood* 106:3507-3514; Stampachiacchiere et al., 2005, *J. Neuroimmunol.* 169:20-30). It has also been found that administration of NGF dramatically reduced the number and size of lesions produced in EAE, upregulated the anti-inflammatory cytokine IL-10 in glial cells and suppressed interferon-γ expression by infiltrating T-cells (Villoslada et al., 2002, *J. Exp. Med.* 191:1799-1806). Anti-NGF treatment of rats resulted in more severe EAE pathology (Micera et al., 2000, *J. Neuroimmunol.* 104:116-123). Without wishing to be bound by any particular theory, it is believed that stimulation of NGF in the parenchymal cells by hBMSCs contributes to the reduction of axonal injury and improvement of neurological outcome.

The results presented herein demonstrate that MAB1281+ cells significantly increased at 10, 20, 35 and 45 weeks compared to the MAB1281+ cells at 1 week after hBMSC transplantation. It is believed that the increased number of hBMSCs present after transplantation facilitates functional recovery. It was observed that hBMSCs entered the CNS of EAE mice and contributed to the decreased mortality and improved neurological functional recovery from as early as 1 week up to 45 weeks in the mice. The transplanted cells contributed to the reduced axonal loss in the EAE brain, and stimulated brain parenchymal cells to express NGF, which is believed to provide both neurotrophic and immunomodulatory effects. The results presented herein demonstrate that BMSC treatment is useful for therapy of autoimmune demyelinating disorders.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a mammal having a disease, disorder or condition of the central nervous system, the method comprising isolating a stromal cell from a bone marrow sample, culturing the cells in the presence of a growth factor selected from the group consisting of NGF, BDNF and EGF, and administering by intravascular administration adjacent to the lesion said stromal cell to said mammal, wherein the cells are not fully differentiated prior to administration and wherein the presence of said stromal cells in the central nervous system of the mammal results in proliferation and differentiation of exogenous bone marrow stromal cells and endogenous neural stem cells, thereby effecting treatment of said disease, disorder or condition.

2. The method according to claim 1, wherein the presence of said stromal cell in the central nervous system of the mammal does not induce an immune response against said stromal cell.

3. The method according to claim 1, wherein the presence of said stromal cell in the central nervous system of the mammal reduces axonal loss.

4. The method of claim 1, wherein said stromal cell is selected from the group consisting of an autologous stromal cell, an allogeneic stromal cell, a syngeneic stromal cell, and a xenogeneic stromal cell, with respect to said mammal.

5. The method of claim 1, wherein said mammal is a human.

6. The method of claim 1, wherein said stromal cell is derived from a human donor.

7. The method of claim 1, wherein said disease, disorder or condition of the central nervous system is selected from the group consisting of a genetic disease, an ischemic induced injury, a spinal cord injury, stroke, Parkinson's disease, multiple sclerosis (MS), and a neurodegenerative disease.

8. The method of claim 7, wherein said disease/disorder is injury to a tissue or a cell of said central nervous system.

9. The method of claim 7, wherein said disease/disorder is within the brain of said mammal.

10. The method of claim 1, wherein said stromal cell administered to said central nervous system remains present or replicates in said central nervous system.

11. The method of claim 1, wherein prior to administering said stromal cell to said mammal, said cell is cultured in vitro for a period of time.

12. The method of claim 1, wherein prior to administering said stromal cell to said mammal, said stromal cell is transfected with an isolated nucleic acid encoding a therapeutic protein, wherein when such protein is secreted by said stromal cell, said protein serves to effect treatment of said disease/disorder.

13. The method of claim 1, wherein following administering said stromal cell to said mammal, said stromal cell migrates to the site of injury.

14. The method of claim 1, wherein said stromal cell present in the central nervous system activates the proliferation of neighboring cells.

15. The method of claim 1, wherein said stromal cell is administered concomitantly with a growth factor.

16. The method of claim 1, wherein said stromal cell administered to said mammal reduces axonal fiber loss in the cells of the mammal.

17. The method of claim 1, wherein said stromal cell administered to said mammal reduces demyelination in the cells of the mammal.

* * * * *